(12) United States Patent
Cardarelli et al.

(10) Patent No.: US 8,461,308 B2
(45) Date of Patent: *Jun. 11, 2013

(54) MONOCLONAL ANTIBODIES AGAINST PROSTATE SPECIFIC MEMBRANE ANTIGEN (PSMA) LACKING IN FUCOSYL RESIDUES

(75) Inventors: Josephine M. Cardarelli, San Carlos, CA (US); David B. Passmore, San Carlos, CA (US); Jenny Albanese, South Lake Tahoe, CA (US); Lei Zhu, Bellevue, WA (US)

(73) Assignee: Medarex, Inc., Princeton, NJ (US)

( * ) Notice: Subject to any disclaimer, the term of this patent is extended or adjusted under 35 U.S.C. 154(b) by 297 days.

This patent is subject to a terminal disclaimer.

(21) Appl. No.: 12/903,853

(22) Filed: Oct. 13, 2010

(65) Prior Publication Data

US 2011/0028696 A1 Feb. 3, 2011

Related U.S. Application Data

(63) Continuation of application No. 11/918,191, filed as application No. PCT/US2006/005853 on Feb. 17, 2006, now Pat. No. 7,875,278.

(60) Provisional application No. 60/654,266, filed on Feb. 18, 2005, provisional application No. 60/660,431, filed on Mar. 9, 2005.

(51) Int. Cl.
*C07K 16/30* (2006.01)

(52) U.S. Cl.
USPC ............... 530/387.7; 530/350; 530/387.1; 530/387.3; 530/388.26; 530/388.8; 530/391.3; 530/391.7

(58) Field of Classification Search
USPC ............ 530/350, 387.1, 387.3, 391.7, 387.7, 530/388.28, 388.8, 391.3
See application file for complete search history.

(56) References Cited

U.S. PATENT DOCUMENTS

| | | | |
|---|---|---|---|
| 5,036,003 | A | 7/1991 | Olander et al. |
| 5,153,118 | A | 10/1992 | Wright, Jr. et al. |
| 5,162,504 | A | 11/1992 | Horoszewicz |
| 5,227,471 | A | 7/1993 | Wright, Jr. |
| 5,453,359 | A | 9/1995 | Gargan et al. |
| 5,489,525 | A | 2/1996 | Pastan |
| 5,538,866 | A | 7/1996 | Israeli et al. |
| 5,643,786 | A | 7/1997 | Cohen et al. |
| 5,773,292 | A | 6/1998 | Bander |
| 5,855,866 | A | 1/1999 | Thorpe et al. |
| 6,051,230 | A | 4/2000 | Thorpe et al. |
| 6,107,090 | A | 8/2000 | Bander |
| 6,136,311 | A | 10/2000 | Bander |
| 6,150,508 | A | 11/2000 | Murphy et al. |
| 6,194,152 | B1 | 2/2001 | Laus et al. |
| 7,105,159 | B1 | 9/2006 | Israeli et al. |
| 2003/0003101 | A1 | 1/2003 | Bander |
| 2004/0033229 | A1 | 2/2004 | Maddon et al. |
| 2004/0110704 | A1 | 6/2004 | Yamane et al. |
| 2004/0132140 | A1 | 7/2004 | Satoh et al. |
| 2006/0024317 | A1 | 2/2006 | Boyd et al. |
| 2006/0275212 | A1 | 12/2006 | Bander |
| 2009/0060908 | A1 | 3/2009 | Cardarelli et al. |

FOREIGN PATENT DOCUMENTS

| | | |
|---|---|---|
| CA | 2250141 | 10/1997 |
| EP | 0228243 B1 | 7/1987 |
| EP | 1176195 A1 | 1/2002 |
| EP | 1498485 A1 | 1/2005 |
| WO | 94/02156 A1 | 2/1994 |
| WO | 94/09820 A1 | 5/1994 |
| WO | 96/08570 A1 | 3/1996 |
| WO | 96/26272 A1 | 8/1996 |
| WO | 96/39185 A1 | 12/1996 |
| WO | 97/35616 A1 | 10/1997 |
| WO | 98/03873 A1 | 1/1998 |
| WO | 99/47554 A1 | 9/1999 |
| WO | 01/09192 A1 | 2/2001 |
| WO | 02/069907 A2 | 9/2002 |
| WO | 03/034903 A2 | 5/2003 |
| WO | 03/035835 A2 | 5/2003 |
| WO | 03/064606 A2 | 8/2003 |
| WO | 03/085107 A1 | 10/2003 |

OTHER PUBLICATIONS

Rudikoff et al (Proc. Natl. Acad. Sci. USA. 1982; 79: 1979-1983).*
Mariuzza et al. (Annu. Rev. Biophys. Biophys. Chem. 1987; 16: 139-159).*
Gussow et al. (Methods in Enzymology. 1991; 203: 99-121).*
Winkler et al. (J. Immunol. Oct. 15, 2000; 165 (8): 4505-4514).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5536).*
Caldas et al. (Mol. Immunol. May 2003; 39 (15): 941-952).*
Vajdos et al. (J. Mol. Biol. Jul. 5, 2002; 320 (2): 415-428).*
De Pascalis et al. (J. Immunol. 2002; 169 (6): 3076-3084).*
Wu et al. (J. Mol. Biol. Nov. 19, 1999; 294 (1): 151-162).*
Casset et al. (Biochem. Biophys. Res. Commun. Jul. 18, 2003; 307 (1): 198-205).*
MacCallum et al. (J. Mol. Biol. Oct. 11, 1996; 262 (5): 732-745).*
Holm et al. (Mol. Immunol. Feb. 2007; 44 (6): 1075-1084).*
George et al. (Circulation. 1998; 97: 900-906).*

(Continued)

*Primary Examiner* — Stephen Rawlings
(74) *Attorney, Agent, or Firm* — Nelson Mullins Riley & Scarborough LLP; Jane E. Remillard; Jill Gorny Sloper

(57) ABSTRACT

The invention pertains to anti-PSMA antibodies that lack fucosyl residues. The antibodies of the invention exhibit increased antibody-dependent cellular cytotoxicity (ADCC) activity as compared to the fucosylated form of the antibodies. The invention also provides host cells that express the anti-PSMA antibodies that lack fucosyl residues, wherein the host cells are deficient for a fucosyl transferase. Methods of using the antibodies to inhibit the growth of PSMA$^+$ cells, such as tumor cells, are also provided.

22 Claims, 22 Drawing Sheets

OTHER PUBLICATIONS

Veldscholte et al. (J. Steroid Biochem. Mol. Biol. Mar. 1992; 41 (3-8): 665-9).*

George, Jacob et al., "Differential Effects of Anti-beta2-Glycoprotein I Antibodies on Endothelial Cells and on the Manifestations of Experimental Antiphospholipid Syndrome," Circulation, vol. 97:900-906 (1998).

Mori, Katsuhiro et al., "Engineering Chinese Hamster Ovary Cells to Maximize Effector Function of Produced Antibodies Using FUT8 siRNA," Biotechnol. Bioeng., vol. 88(7):901-908 (2004).

Niwa, Rinpei et al., "Defucosylated Chimeric Anti-CC Chemokine Receptor 4 IgG1 with Enhanced Antibody-Dependent Cellular Cytotoxicity Shows Potent Therapeutic Activity to T-Cell Leukemia and Lymphoma," Cancer Research, vol. 64:2127-2133 (2004).

Okazaki, Akira et al., "Fucose Depletion from Human IgG1 Oligosaccharide Enhances Binding Enthalpy and Association Rate Between IgG1 and FcgammaRIIIa," J. Mol. Biol., vol. 336:1239-1249 (2004).

Bander, Neil H. et al., "Phase I Trial of 177Lutetium-Labeled J591, a Monoclonal Antibody to Prostate-Specific Membrane Antigen, in Patients With Androgen-Independent Prostate Cancer," Journal of Clinical Oncology, vol. 23 (23):4591-4601 (2005).

Beutler, Hans-Otto, "L-Glutamate, Colorimetric Method with Glutamate Dehydrogenase and Diaphorase," Methods of Enzymatic Analysis, 3rd Edition, Bergmeyer, H.U. ed., vol. VIII, pp. 369-376, VCH Publishers (UK) Ltd., Cambridge, UK (1985).

Brueggermann, Marianne et al., "Strategies for expressing human antibodies repertoires in transgenic mice," Immunology, Today, vol. 17(8):391-396 (1996).

Caldas, Cristina et al., "Humanization of the anti-CD18 antibody 6.7: an unexpected effect of a framework residue in binding to antigen," Molecular Immunology, vol. 39:941-952 (2003).

Carter, Ruth E. et al., "Prostate-specific membrane antigen is a hydrolase with substrate and pharmacologic characteristics of a neuropeptidase," Proc. Natl. Acad. Sci. USA, vol. 93:749-753 (1996).

Chang, Sam S. et al., "Five Different Anti-Prostate-specific Membrane Antigen (PSMA) Antibodies Confirm PSMA Expression in Tumor-associated Neuvasculature," Cancer Research, vol. 59:3192-3198 (1999).

Chang, Sam S. et al., "Prostate-specific Membrane Antigen Is Produced in Tumor-associated Neovasculature," Clinical Cancer Research, vol. 5:2674-2681 (1999).

Chien, Nadine C. et al., "Significant structural and functional change of an antigen-binding site by a distant amino acid substitution: Proposal of a structural mechanism," Proc. Natl. Acad. Sci. USA, vol. 86:5532-5536 (1989).

Curnow, Randall T., "Clinical experience with CD64-directed immunotherapy. An overview," Cancer Immunol. Immunother., vol. 45:210-215 (1997).

Davies, Julian et al., "Expression of GnTIII in a Recombinant Anti-CD20 CHO Production Cell Line: Expression of Antibodies with Altered Glycoforms Leads to an Increase in ADCC Through Higher Affinity for Fcgamma RIII," Biotechnol. Bioeng., vol. 74(4):288-294 (2001).

Donovan, Gerald P. et al., "Antibody and Vaccine Therapies Targeting Prostate Specific Membrane Antigen (PSMA)," Proceedings of the American Association for Cancer Research, vol. 42:818, No. 4389 (2001).

Fernandez, I.M. et al., "Epitope polarity and adjuvants influence the fine specificity of the humoral response against Semliki Forest virus specific peptide vaccines," Vaccine, vol. 16(16):1531-1536 (1998).

Fernandez, I.M. et al., "Influence of Epitope Polarity and Adjuvants on the Immunogenicity and Efficacy of a Synthetic Peptide Vaccine against Semliki Forest Virus," Journal of Virology, vol. 67(10):5843-5848 (1993).

Giusti, Angela M. et al., "Somatic diversification of S107 from an antiphosphocholine to an anti-DNA autoantibody is due to a single base change in its heavy chain variable region," Proc. Natl. Acad. Sci. USA, vol. 84:2926-2930 (1987).

Gong, Michael C. et al., "Prostate-specific membrane antigen (PSMA)-specific monoclonal antibodies in the treatment of prostate and other cancers," Cancer and Metastasis Reviews, vol. 18:483-490 (1999).

Green, Larry L., "Antibody engineering via genetic engineering of the mouse: XenoMouse strains are a vehicle for the facile generation of therapeutic human monoclonal antibodies," Journal of Immunological Methods, vol. 231:11-23 (1999).

Greenspan, Neil S. et al., "Defining epitopes: It's not easy as it seems," Nature Biotechnology, vol. 17:936-937 (1999).

Guessow, Detlef et al., "Humanization of Monoclonal Antibodies," Methods in Enzymology, vol. 203, Molecular Design and Modeling Concepts and Applications, Part B, Antibodies and Antigens, Nucleic Acids, Polysaccharides, and Drugs, John J. Langone, Ed., Academic Press, Inc., San Diego, Chpt. 5, pp. 99-121 (1991).

Hamilton, A. et al., "A novel humanized antibody against Prostate Specific Membrane Antigen (PSMA) for in vivo targeting and therapy," Proceedings of the American Association for Cancer Research 89th Annual Meeting, New Orleans, Louisiana, USA, vol. 39, No. 2997 (1989).

Heston, Warren D.W., "Characterization and Glutamyl Preferring Carboxypeptidase Function of Prostate Specific Membrane Antigen: A Novel Folate Hydrolase," Urology, vol. 49(Suppl. 3A):104-112 (1997).

Holmes, Eric H. et al., "Analysis of Glycosylation of Prostate-Specific Membrane Antigen Derived From LNCaP Cells, Prostatic Carcinoma Tumors, and Serum From Prostate Cancer Patients," The Prostate Supplement, vol. 7:25-29 (1996).

Holmes, Eric H. et al., "Development and Characterization of Monoclonal Antibodies Specific for the Extracellular Domain of Prostate-Specific Membrane Antigen," Cancer Biotherapy & Radiopharmaceuticals, vol. 13(1):55, No. 12 (1998).

Holmes, Eric H., "PSMA specific antibodies and their diagnostic and therapeutic use," Exp. Opin. Invest Drugs, vol. 10(3):511-519 (2001).

Horoszewicz, Julius S. et al., "Monoclonal Antibodies to a New Antigenic Marker in Epithelial Prostatic Cells and Serum of Prostatic Cancer Patients," Anticancer Research, vol. 7:927-936 (1987).

Israeli, Ron S. et al., "Expression of the Prostate-specific Membrane Antigen," Cancer Research, vol. 54:1807-1811 (1994).

Israeli, Ron S. et al., "Molecular Cloning of a Complementary DNA Encoding a Prostate-specific Membrane Antigen," Cancer Research, vol. 53:227-230 (1993).

Jakobovits, Aya, "The long-awaited magic bullets: therapeutic human monoclonal antibodies from transgenic mice," Exp. Opin. Invest. Drugs, vol. 7(4):607-614 (1998).

Jiang, Beihai et al., "A Novel Peptide Isolated from a Phage Display Peptide Library with Trastuzumab Can Mimic Antigen Epitope of HER-2," The Journal of Biological Chemistry, vol. 28(6):4656-1662 (2005).

Lazar, Eliane et al., "Transforming Growth Factor a: Mutation of Aspartic Acid 47 and Leucine 48 Results in Different Biological Activities," Molecular and Cellular Biology, vol. 8(3):1247-1252 (1988).

Leek, J. et al., "Prostate-specific membrane antigen: evidence for the existence of a second related human gene," Br. J. Cancer, vol. 72(3):583-585 (1995).

Liu, He et al., "Monoclonal Antibodies to the Extracellular Domain of Prostate-specific Membrane Antigen Also React with Tumor Vascular Endothelium," Cancer Research, vol. 57:3629-3634 (1997).

Mariuzza, R.A. et al., "The Structural Basis of Antigen-antibody Recognition," Ann. Rev. Biophys. Biophys. Chem., vol. 16:139-159 (1987).

Morris, Michael J. et al., "Pilot Trial of Unlabeled and Indium-111-Labeled Anti-Prostate-Specific Membrane Antigen Antibody J591 for Castrate Metastatic Prostate Cancer," Clin. Cancer Res., vol. 11(20):7454-7461 (2005).

Murphy, G.P. et al., "Comparison of Prostate Specific Antigen, Prostate Specific Membrane Antigen, and LNCaP-Based Enzyme-Linked Immunosorbent Assays in Prostatic Cancer Patients and Patients With Benign Prostatic Enlargement," The Prostate, vol. 26:164-168 (1995).

Murphy, Gerald et al., "Comparison of Prostate Specific Membrane Antigen, and Prostate Specific Antigen Levels in Prostatic Cancer Patients," Anticancer Research, vol. 15:1473-1480 (1995).

Murphy, Gerald P. et al., "Isolation and Characterization of Monoclonal Antibodies Specific for the Extracellular Domain of Prostate Specific Membrane Antigen," The Journal of Urology, vol. 160:2396-2401 (1998).

Murphy, G.P. et al., "Measurement of Prostate-Specific Membrane Antigen in the Serum With a New Antibody," The Prostate, vol. 28:266-271 (1996).

Murphy, Gerald P. et al., "Measurement of Serum Prostate-specific Membrane Antigen, a New Prognostic Marker for Prostate Cancer," Urology, vol. 51(Suppl. 5A):89-97 (1998).

Nakamura, R.M. et al., "Enzyme immunoassays: heterogeneous and homogeneous systems," Handbook of Exp. Immunol., Well et al., Eds., Blackwell Scientific Publications, Oxford, Chpt. 27:27.1-27.20 (1997).

Niwa, Rinpei et al., "Enhancement of the Antibody-Dependent Cellular Cytotoxicity of Low-Fucose IgG1 Is Independent of FcgammaRIIIa Functional Polymorphism," Clinical Cancer Research, vol. 10:6248-6255 (2004).

O'Keefe, Denise S. et al., "Comparative Analysis of Prostate-Specific Membrane Antigen (PSMA) Versus a Prostate-Specific Membrane Antigen-Like Gene," The Prostate, vol. 58:200-210 (2004).

Pohl, C. et al., "CD30-Specific AB1-AB2-AB3 Internal Image Antibody Network: Potential Use as Anti-Idiotype Vaccine Against Hodgkin's Lymphoma," Int. J. Cancer, vol. 54:418-425 (1993).

Rochon, Yvan P. et al., "Western Blot Assay for Prostate-Specific Membrane Antigen in Serum of Prostate Cancer Patients," The Prostate, vol. 25:219-223 (1994).

Roitt et al., Immunology, 3rd Ed., Mosby, St. Louis, p. 1.6 (1993).

Schmittgen, Thomas D. et al., "Expression of Prostate Specific Membrane Antigen and Three Alternatively Spliced Variants of PSMA in Prostate Cancer Patients," Int. J. Cancer, vol. 107:323-329 (2003).

Sharkey, Robert M. et al., "Enhanced Clearance of Radiolabeled Murine Monoclonal Antibody by a Syngeneic Anti-Idiotype Idiotype Antibody in Tumor-Bearing Nude Mice," Int. J. Cancer, vol. 51:266-273 (1992).

Shields, Robert L. et al., "Lack of Fucose on Human IgG1 N-Linked Oligosaccharide Improves Binding to Human FcgammaRIII and Antibody-dependent Cellular Toxicity," The Journal of Biological Chemistry, vol. 277 (30):26733-26740 (2002).

Shinkawa, Toyohide et al., "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity," The Journal of Biological Chemistry, vol. 278(5):3466-3473 (2003).

Stancovski, Ilana et al., "Mechanistic aspects of the opposing effects of monoclonal antibodies to the ERBB2 receptor on tumor growth," Proc. Natl. Acad. Sci. USA, vol. 88:8691-8695 (1991).

Su, Sai L. et al., "Alternatively Spliced Variants of Prostate-specific Membrane Antigen RNA: Ratio of Expression as a Potential Measurement of Progression," Cancer Research, vol. 1441-1443 (1995).

Tino, William T. et al., "Isolation and Characterization of Monoclonal Antibodies Specific for Protein Conformational Epitopes Present in Prostate-Specific Membrane Antigens (PSMA)," Hybridoma, vol. 19(3):249-257 (2000).

Tjoa, Benjamin et al., "In Vitro Propagated Dendritic Cells From Prostate Cancer Patients as a Component of Prostate Cancer Immunotherapy," The Prostate, vol. 27:63-69 (1995).

Troyer, John K. et al., "Biochemical Characterization and Mapping of the 7EII-C5.3 Epitope of the Prostate-Specific Membrane Antigen," Urol. Oncol., vol. 1:29-37 (1995).

Troyer, John K. et al., "Detection and Characterization of the Prostate-specific Membrane Antigen (PSMA) in Tissue Extracts and Body Fluids," Int. J. Cancer, vol. 62:552-558 (1995).

Troyer, J.K. et al., "Subcellular localization of the 7E11-C5 prostate specific antigen," Proceedings of the American Association for Cancer Research, vol. 35:283, No. 1688 (1994).

Vaughan, Tristan J. et al., "Human antibodies by design," Nature Biotechnology, vol. 16:535-539 (1998).

Wright, G.L. Jr. et al., "Characterization of a new prostate carcinoma-associated marker: 7E11-C5," Antibody, Immunoconjugates and Radiopharmaceuticals, vol. 3(1):89, No. 193 (1990).

Yamane-Ohnuki, Naoko et al., "Establishment of FUT8 Knockout Chinese Hamster Ovary Cells: An Ideal Host Cell Line for Producing Completely Defucosylated Antibodies With Enhanced Antibody-Dependent Cellular Cytotoxicity," Biotechnology and Bioengineering, vol. 87(5):614-622 (2004).

Zhu, Lei et al., "Production of human monoclonal antibody in eggs of chimeric chickens," Nature Biotechnology, vol. 23(9):1159-1169 (2005).

Written Opinion for Application No. PCT/US2006/005853, dated Sep. 21, 2006.

Bander, Neil H. et al., "Targeted Systemic Therapy of Prostate Cancer With a Monoclonal Antibody to Prostate-Specific Membrane Antigen," Seminars in Oncology, vol. 30(5):667-677 (2003).

Henry, Michael D. et al., "A Prostate-Specific Membrane Antigen-Targeted Monoclonal Antibody-Chemotherapeutic Conjugate Designed for the Treatment of Prostate Cancer," Cancer Research, vol. 64:7995-8001 (2004).

Patri, Anil K. et al., "Synthesis and in Vitro Testing of J591 Antibody-Dendrimer Conjugates for Targeted Prostate Cancer Therapy," Bioconjugate Chem., vol. 15:1174-1181 (2004).

US 6,290,956, 09/2001, Bander (withdrawn)

* cited by examiner

Fig. 1

```
                   CDR1
L6 germline:  E I V L T Q S P A T L S L S P G E R A T L S C  R A S Q S V S S Y L A
4A3:          - - - - - - - - - - - - - - - - - - - - - - -  - - - - - - - - - - -
7F12:         - - - - - - - - - - - - - - - - - - - - - - -  - - - - - - - - - - -
8C12:         - - - - - - - - - - - - - - - - - - - - - - -  - - - - - - - - - - -

CDR2
L6 germline:  W Y Q Q K P G Q A P R L L I Y  D A S N R A T  G I P A R F S G S G S
4A3:          - F - - - - - - - - - - - - -  - - - - - - -  - - - - - - - - - - -
7F12:         - - - - - - - - - - - - - - -  - - - - - - -  - - - - - - - - - - -
8C12:         - - - - - - - - - - - - - - -  - - - - - - -  - - - - - - - - - - -

L6 germline:  G T D F T L T I S S L E P E D F A V Y Y C
4A3:          - - - - - - - - - - - - - - - - - - - - -
7F12:         - - - - - - - - - - - - - - - - - - - - -
8C12:         - - - - - - - - - - - - - - - - - - - - -

CDR3
L6 germline:  Q Q R S N W - - L M Y T  F G Q G T K L E I K
4A3:          - - - - - - - - - - - -  - - - - - - - - - -
7F12:         - - - - - - - D - - - -  - - - - - - - - - -
8C12:         - - - - - - - - - - - -  - - - - - - - - - -
```

*Fig. 2*

```
                                              CDR1
VK 04/014
germline:    D I Q L T Q S P S S L S A S V G D R V T I T C  R V S Q G I S S Y L N
8A11:        - - - - - - - - - - - - - - - - - - - - S - -  - - - - - - - - - - -
16F9:        - - - - - - - - - - - - - - - - - - - - - - -  - - - - - - - - - - -

CDR2
014 germline: W Y R Q K P G K V P K L L I Y  S A S N L Q S  G V P S R F S G S G S
8A11:         - - - - - - - - - - - - - - -  - - - - - - -  - - - - - - - - - - -
16F9:         - - - - - - - - - - - - - M -  - - - - - - -  - - - - - - - - - - -

CDR3
014 germline: G T D F T L T I S S L Q P E D V A T Y Y G  Q R T Y N A P F T  F G P G
8A11:         - - - - - - - - - - N - - - - - - - - -  - - - - - - - - -  - - - -
16F9:         - - - - - - - - - - - - - - - - - - - -  - - - - - - - - -  - - - -

Anti-PMSA 1C3 VH
    V segment:    3-30.3
    D segment:    undetermined
    J segment:    JH6b

```
        Q   V   Q   L   V   E   S   G   G   G   V   V   Q   P   G   R   S   L
   1    CAG GTG CAA CTG GTG GAG TCT GGG GGA GGC GTG GTC CAG CCT GGG AGG TCC CTG

CDR1
                                                              ------------------
        R   L   S   C   A   A   S   G   F   T   F   S   S   Y   A   M   H   W
  55    AGA CTC TCC TGT GCA GCC TCT GGA TTC ACC TTC AGT AGC TAT GCT ATG CAC TGG

CDR2
                                                              ------------------
        V   R   Q   A   P   G   K   G   L   E   W   V   A   V   I   S   Y   D
 109    GTC CGC CAG GCT CCA GGC AAG GGG CTG GAG TGG GTG GCA GTT ATA TCA TAT GAT

CDR2
        ----------------------------------------------------
        G   N   N   K   Y   Y   A   D   S   V   K   G   R   F   T   I   S   R
 163    GGA AAC AAT AAA TAC TAC GCA GAC TCC GTG AAG GGC CGA TTC ACC ATC TCC AGA

D   N   S   K   N   T   L   Y   L   Q   M   N   S   L   R   A   E   D
 217    GAC AAT TCC AAG AAC ACG CTG TAT CTG CAA ATG AAC AGC CTG AGA GCT GAG GAC

CDR3
                                                              ------------------
        T   A   V   Y   Y   C   A   R   A   V   P   W   G   S   R   Y   Y   Y
 271    ACG GCT GTG TAT TAC TGT GCG AGA GCC GTC CCC TGG GGA TCG AGG TAC TAC TAC
                                                                        └──→ JH6b

CDR3
        ----------------------
        Y   G   M   D   V   W   G   Q   G   T   T   V   T   V   S   S
 325    TAC GGT ATG GAC GTC TGG GGC CAA GGG ACC ACG GTC ACC GTC TCC TCA
```

*Fig. 4A*

```
Anti-PSMA 1C3 VK
    V segment:      L18
    J segment:      JK4

A   I   Q   L   T   Q   S   P   S   S   L   S   A   S   V   G   D   R
  1     GCC ATC CAG TTG ACC CAG TCT CCA TCC TCC CTG TCT GCA TCT GTA GGA GAC AGA

CDR1
                                        ~~~~~~~~~~~~~~~~~~~~~~~~~~~~~~~~~~~~~~~~~~
        V   T   I   T   C   R   A   S   Q   G   I   S   S   A   L   A   W   Y
  55    GTC ACC ATC ACT TGC CGG GCA AGT CAG GGC ATT AGC AGT GCT TTA GCC TGG TAT

CDR2
                                                            ~~~~~~~~~~~~~~~~~~~~
        Q   Q   K   S   G   K   A   P   K   L   L   I   F   D   A   S   S   L
  109   CAG CAG AAA TCA GGG AAA GCT CCT AAG CTC CTG ATC TTT GAT GCC TCC AGT TTG

CDR2
        ~~~~~~~
        E   S   G   V   P   S   R   F   S   G   S   G   S   G   T   D   F   T
  163   GAA AGT GGG GTC CCA TCA AGG TTC AGC GGC AGT GGA TCT GGG ACA GAT TTC ACT

CDR3
                                                                            ~~~~~~~
        L   T   I   S   S   L   Q   P   E   D   F   A   T   Y   Y   C   Q   Q
  217   CTC ACC ATC AGC AGC CTG CAG CCT GAA GAT TTT GCA ACT TAT TAC TGT CAA CAG

CDR3
        ~~~~~~~~~~~~~~~~~~~~~~~~~~~~
        F   N   S   Y   P   L   T   F   G   G   G   T   K   V   E   I   K
  271   TTT AAC AGT TAT CCT CTC ACT TTC GGC GGA GGG ACC AAG GTG GAG ATC AAA
                            └──▶ JK4
```

*Fig. 4B*

```
Anti-PMSA 2A10 VH
    V segment:    5-51
    D segment:    7-27
    J segment:    JH2

E   V   Q   L   V   Q   S   G   A   E   V   K   K   P   G   E   S   L
    1   GAG GTG CAG CTG GTG CAG TCT GGA GCA GAG GTG AAA AAG CCC GGG GAG TCT CTG

CDR1
                                                                    ------------------

K   I   S   C   K   G   S   G   Y   S   F   T   S   N   W   I   G   W
    55  AAG ATC TCC TGT AAG GGT TCT GGA TAC AGC TTT ACC AGT AAC TGG ATC GGC TGG

CDR2
                                                                    ------------------

V   R   Q   M   P   G   K   G   L   E   W   M   G   I   I   Y   P   G
    109 GTG CGC CAG ATG CCC GGG AAA GGC CTG GAG TGG ATG GGA ATC ATC TAT CCT GGT

CDR2
        ----------------------------------------------------------------
        D   S   D   T   R   Y   S   P   S   F   Q   G   Q   V   T   I   S   A
    163 GAC TCT GAT ACC AGA TAC AGC CCG TCC TTC CAA GGC CAG GTC ACC ATC TCA GCC

D   K   S   I   S   T   A   Y   L   Q   W   S   S   L   K   A   S   D
    217 GAC AAG TCC ATC AGC ACC GCC TAC CTG CAG TGG AGC AGC CTG AAG GCC TCG GAC

CDR3
                                                                --------------------------------------------
        T   A   M   Y   Y   C   A   R   Q   T   G   F   L   W   S   S   D   L
    271 ACC GCC ATG TAT TAC TGT GCG AGG CAA ACT GGT TTC CTC TGG TCC TCC GAT CTC
                                                            └──→ JH2

W   G   R   G   T   L   V   T   V   S   S
    325 TGG GGC CGT GGC ACC CTG GTC ACT GTC TCC TCA
```

*Fig. 5A*

Anti-PSMA 2A10 VK

V segment:     L18
    J segment:     JK4

```
         A   I   Q   L   T   Q   S   P   S   S   L   S   A   S   V   G   D   R
  1     GCC ATC CAG TTG ACC CAG TCT CCA TCC TCC CTG TCT GCA TCT GTA GGA GAC AGA

CDR1
                                    ------------------------------------------
         V   T   I   T   C   R   A   S   Q   D   I   S   S   A   L   A   W   Y
 55     GTC ACC ATC ACT TGC CGG GCA AGT CAG GAC ATT AGC AGT GCT TTA GCC TGG TAT

CDR2
                                                        --------------------
         Q   Q   K   P   G   K   A   P   K   L   L   I   Y   D   A   S   S   L
109     CAA CAG AAA CCA GGG AAA GCT CCT AAG CTC CTG ATC TAT GAT GCC TCC AGT TTG

CDR2
        --------
         E   S   G   V   P   S   R   F   S   G   Y   G   S   G   T   D   F   T
163     GAA AGT GGG GTC CCA TCA AGG TTC AGC GGC TAT GGA TCT GGG ACA GAT TTC ACT

CDR3
                                                                   --------
         L   T   I   N   S   L   Q   P   E   D   F   A   T   Y   Y   C   Q   Q
217     CTC ACC ATC AAC AGC CTG CAG CCT GAA GAT TTT GCA ACT TAT TAC TGT CAA CAG

CDR3
        ------------------------------
         F   N   S   Y   P   L   T   F   G   G   G   T   K   V   E   I   K
271     TTT AAT AGT TAC CCG CTC ACT TTC GGC GGA GGG ACC AAG GTG GAG ATC AAA
```

*Fig. 5B*

Anti-PMSA 2C6 VH
V segment:    5-51
D segment:    6-13
J segment:    JH4b

```
         E   V   Q   L   V   Q   S   G   S   E   V   K   K   P   G   E   S   L
  1      GAG GTG CAG CTG GTG CAG TCT GGA TCA GAG GTG AAA AAG CCC GGG GAG TCT CTG

CDR1
                                                    ----------------------
         K   I   S   C   K   G   S   G   Y   S   F   T   N   Y   W   I   G   W
 55      AAG ATC TCC TGT AAG GGT TCT GGA TAC AGC TTT ACC AAC TAC TGG ATC GGC TGG

CDR2
                                                    ----------------------
         V   R   Q   M   P   G   K   G   L   E   W   M   G   I   I   Y   P   G
109      GTG CGC CAG ATG CCC GGG AAA GGC CTG GAG TGG ATG GGG ATC ATC TAT CCT GGT

CDR2
   ------------------------------------------------
         D   S   D   T   R   Y   S   P   S   F   Q   G   Q   V   T   I   S   A
163      GAC TCT GAT ACC AGA TAC AGC CCG TCC TTC CAA GGC CAG GTC ACC ATC TCA GCC

D   K   S   I   S   T   A   Y   L   Q   W   S   S   L   K   A   S   D
217      GAC AAG TCC ATC AGC ACC GCC TAT CTG CAG TGG AGC AGC CTG AAG GCC TCG GAC

CDR3
                                                    ----------------------------------------
         T   A   M   Y   Y   C   A   S   P   G   Y   T   S   S   W   T   S   F
271      ACC GCC ATG TAT TAC TGT GCG AGT CCC GGG TAT ACC AGC AGT TGG ACT TCT TTT

CDR3
         --------
         D   Y   W   G   Q   G   T   L   V   T   V   S   S
325      GAC TAC TGG GGC CAG GGA ACC CTG GTC ACC GTC TCC TCA
```

*Fig. 6A*

Anti-PSMA 2C6 VK

V segment:       L6
J segment:       JK3

```
      E   I   V   L   T   Q   S   P   A   T   L   S   L   S   P   G   E   R
  1   GAA ATT GTG TTG ACA CAG TCT CCA GCC ACC CTG TCT TTG TCT CCA GGG GAA AGA

CDR1
                      ------------------------------------------------------
      A   T   L   S   C   R   A   S   Q   S   V   S   S   Y   L   A   W   Y
 55   GCC ACC CTC TCC TGC AGG GCC AGT CAG AGT GTT AGC AGC TAC TTA GCC TGG TAC

CDR2
                                                      ----------------------
      Q   Q   K   P   G   Q   A   P   R   L   L   I   Y   D   A   S   N   R
109   CAA CAG AAA CCT GGC CAG GCT CCC AGG CTC CTC ATC TAT GAT GCA TCC AAC AGG

CDR2
      -------
      A   T   G   I   P   A   R   F   S   G   S   G   S   G   T   D   F   T
163   GCC ACT GGC ATC CCA GCC AGG TTC AGT GGC AGT GGG TCT GGG ACA GAC TTC ACT

CDR3
                                                                      -------
      L   T   I   S   S   L   E   P   E   D   F   A   V   Y   Y   C   Q   Q
217   CTC ACC ATC AGC AGC CTA GAG CCT GAA GAT TTT GCA GTT TAT TAC TGT CAG CAG

CDR3
      ----------------------------------------
      R   S   N   W   P   L   F   T   F   G   P   G   T   K   V   D   I   K
271   CGT AGC AAC TGG CCC CTA TTC ACT TTC GGC CCT GGG ACC AAA GTG GAT ATC AAA
```

*Fig. 6B*

Anti-PMSA 2F5 VH
    V segment:    5-51
    D segment:    7-27
    J segment:    JH2

```
        E   V   Q   L   V   Q   S   G   A   E   V   K   K   P   G   E   S   L
    1   GAG GTG CAG CTG GTG CAG TCT GGA GCA GAG GTG AAA AAG CCC GGG GAG TCT CTG

CDR1
                                                            ~~~~~~~~~~~~~~~~~~~
        K   I   S   C   K   G   S   G   Y   S   F   T   S   N   W   I   G   W
   55   AAG ATC TCC TGT AAG GGT TCT GGA TAC AGT TTT ACC AGC AAC TGG ATC GGC TGG

CDR2
                                                            ~~~~~~~~~~~~~~~~~~~
        V   R   Q   M   P   G   K   G   L   E   W   M   G   I   I   Y   P   G
  109   GTG CGC CAG ATG CCC GGG AAA GGC CTG GAG TGG ATG GGG ATC ATC TAT CCT GGT

CDR2
        ~~~~~~~~~~~~~~~~~~~~~~~~~~~~~~~~~~~~~~~~~~~~~~~~~~~
        D   S   D   T   R   Y   S   P   S   F   Q   G   Q   V   T   I   S   A
  163   GAC TCT GAT ACC AGA TAC AGC CCG TCC TTC CAA GGC CAG GTC ACC ATC TCA GCC

D   K   S   I   S   T   A   Y   L   Q   W   N   S   L   K   A   S   D
  217   GAC AAG TCC ATC AGC ACC GCC TAC CTG CAG TGG AAC AGC CTG AAG GCC TCG GAC

CDR3
                                            ~~~~~~~~~~~~~~~~~~~~~~~~~~~~~~~~~~~
        T   A   M   Y   Y   C   A   R   Q   T   G   F   L   W   S   F   D   L
  271   ACC GCC ATG TAT TAC TGT GCG AGA CAA ACT GGT TTC CTC TGG TCC TTC GAT CTC
                                                            └──► JH2

W   G   R   G   T   L   V   T   V   S   S
  325   TGG GGC CGT GGC ACC CTG GTC ACT GTC TCC TCA
```

*Fig. 7A*

```
Anti-PSMA 2F5 VK
    V segment:    L18
    J segment:    JK4

A   I   Q   L   T   Q   S   P   S   S   L   S   A   S   V   G   D   R
  1   GCC ATC CAG TTG ACC CAG TCT CCA TCC TCC CTG TCT GCA TCT GTA GGA GAC AGA

CDR1
                        ~~~~~~~~~~~~~~~~~~~~~~~~~~~~~~~~~~~~~~~~~~~~~~~
      V   T   I   T   C   R   A   S   Q   D   I   S   S   A   L   A   W   Y
 55   GTC ACC ATC ACT TGC CGG GCA AGT CAG GAC ATT AGC AGT GCT TTA GCC TGG TAT

CDR2
                                                            ~~~~~~~~~~~~~~~~~~~~
      Q   Q   K   P   G   K   A   P   K   L   L   I   Y   D   A   S   S   L
109   CAG CAG AAA CCG GGG AAA GCT CCT AAG CTC CTG ATC TAT GAT GCC TCC AGT TTG

CDR2
      ~~~~~~~
      E   S   G   V   P   S   R   F   S   G   S   G   S   G   T   D   F   T
163   GAA AGT GGG GTC CCA TCA AGG TTC AGC GGC AGT GGA TCT GGG ACA GAT TTC ACT

CDR3
                                                                    ~~~~~~~
      L   T   I   S   S   L   Q   P   E   D   F   A   T   Y   Y   C   Q   Q
217   CTC ACC ATC AGC AGC CTG CAG CCT GAA GAT TTT GCA ACT TAT TAC TGT CAA CAG

CDR3
      ~~~~~~~~~~~~~~~~~~~~~~~~~~~~~
      F   N   S   Y   P   L   T   F   G   G   G   T   K   V   E   I   K
271   TTT AAT AGT TAC CCG CTC ACT TTC GGC GGA GGG ACC AAG GTG GAG ATC AAA
                            └─►JK4

I   K
325   ATC AAA
```

*Fig. 7B*

```
                                                                              CDR1
5-51 germline:  E V Q L V Q S G A E V K K P G E S L K I S C K G S G Y S F T S Y W I G
2A10 VH:        - - - - - - - - - - - - - - - - - - - - - - - - - - - - - - N - - -
2C6 VH:         - - - - - - - - S - - - - - - - - - - - - - - - - - - - - - - - - -
2F5 VH:         - - - - - - - - - - - - - - - - - - - - - - - - - - - - - N - - - -

CDR2
5-51 germline:  W V R Q M P G K G L E W M G I I Y P G D S D T R Y S P S F Q G Q V T I
2A10 VH:        - - - - - - - - - - - - - - - - - - - - - - - - - - - - - - - - - -
2C6 VH:         - - - - - - - - - - - - - - - - - - - - - - - - - - - - - - - - - -
2F5 VH:         - - - - - - - - - - - - - - - - - - - - - - - - - - - - - - - - - -

CDR3
5-51 germline:  S A D K S I S T A Y L Q W S S L K A S D T A M Y Y C A R
2A10 VH:        - - - - - - - - - - - - - - N - - - - - - - - - - - - -
2C6 VH:         - - - - - - - - - - - - - - - - - - - - - - - - - - - -
2F5 VH:         - - - - - - - - - - - - - - - - - - - - - - - - - - - -

CDR3
2A10 VH:  S - - D L W G R G T L V T V S S           (JH2)
2C6 VH:   T S F - Y - - Q - - - - - - - -   S P G Y T S S W   (JH4b)
2F5 VH:   F - - - - - - - - - - - - - - -   Q T G F L W S     (JH2)
```

Fig. 8

```
                                              CDR1
3-30.3 germline:   Q V Q L V E S G G G V V Q P G R S L R L S C A A S G F T F S S Y A M H W V R Q
1C3 VH:            - - - - - - - - - - - - - - - - - - - - - - - - - - - - - - - - - - - - - -

CDR2
3-30.3 germline:   A P G K G L E W V A V I S Y D G S N K Y Y A D S V K G R F T I S R D N S K N T
1C3 VH:            - - - - - - - - - - - - - - - - - N - - - - - - - - - - - - - - - - - - - -

CDR3
3-30.3 germline:   L Y L Q M N S L R A E D T A V Y Y C A R
1C3 VH:            - - - - - - - - - - - - - - - - - - - - - A V P W G S R Y Y Y Y Y G M D V W G Q G JH6b germline:     T T V T V S S
1C3 VH:            - - - - - - - (JH6b)
```

*Fig. 9*

```
L6 germline:  E I V L T Q S P A T L S L P G E R A T L S C R A S Q S V S S Y L A
2C6 VK:       - - - - - - - - - - - - - - - - - - - - - - - - - - - - - - - -
                                                          |_____CDR1_____|

L6 germline:  W Y Q Q K P G Q A P R L L I Y D A S N R A T G I P A R F S G S G S G
2C6 VK:       - - - - - - - - - - - - - - - - - - - - - - - - - - - - - - - - -
                                          |_____CDR2_____|

L6 germline:  T D F T L T I S S L E P E D F A V Y Y C Q Q R S N W       F T F G P G
JK3 germline:                                                   - - P L
2C6 VK:       - - - - - - - - - - - - - - - - - - - - - - - - -       - - - - - -
                                                      |_____CDR3_____|

JK3 germline: T K V D I K   (JK3)
2C6 VK:       - - - - - -
```

*Fig. 10*

```
                                                                    CDR1
L18 germline:  A I Q L T Q S P S S L S A S V G D R V T I T C R A S Q G I S S A L A
1C3 VK:        - - - - - - - - - - - - - - - - - - - - - - - - - - - - - - - - -
2A10 VK:       - - - - - - - - - - - - - - - - - - - - - - - - - - D - - - - - -
2F5 VK:        - - - - - - - - - - - - - - - - - - - - - - - - - - D - - - - - -

CDR2
L18 germline:  W Y Q Q K P G K A P K L L I Y D A S S L E S G V P S R F S G S G S G
1C3 VK:        - - - - - - - - - - - - - - - - - - - - - - - - - - - - - - - - -
2A10 VK:       - - - S - - - - - - - - - - - F - - - - - - - - - - - - - - - Y -
2F5 VK:        - - - - - - - - - - - - - - - - - - - - - - - - - - - - - - - - -

CDR3
L18 germline:  T D F T L T I S S L Q P E D F A T Y Y C Q Q F N S Y P       L T F G G G T
JK4 germline:                                                              L T F G G G T
1C3 VK:        - - - - - - - - - - - - - - - - - - - - - - - - - -        - - - - - - -
2A10 VK:       - - - - - - - - - N - - - - - - - - - - - - - - - -        - - - - - - -
2F5 VK:        - - - - - - - - - - - - - - - - - - - - - - - - - -        - - - - - - -

JK4 germline:  K V E I K
1C3 VK:        - - - - -   (JK4)
2A10 VK:       - - - - -   (JK4)
2F5 VK:        - - - - -   (JK4)
```

*Fig. 11*

Structure characterization of anti-PSMA 7F12 expressed in chicken eggs
| Obs. mass+Na+ | Theo. mass+ Na+ | Structure | Possible structure connectivity | Type |
|---|---|---|---|---|
| 1136.4 | 1136.5 | $(Man)_3(GlcNAc)_3$ | 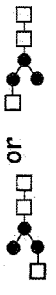 | |
| 1257.4 | 1257.6 | $(Hex)_2(Man)_3(GlcNAc)_2$ |  | |
| 1298.4 | 1298.44 | $(Hex)(Man)_3(GlcNAc)_3$ |  | |
| 1339.46 | 1339.5 | $(Man)_3(GlcNAc)_4$ | 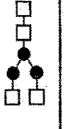 | G0 |
| 1460.49 | 1460.5 | $(Hex)_2(Man)_3(GlcNAc)_3$ |  | |
| 1501.53 | 1501.5 | $(Hex)(Man)_3(GlcNAc)_4$ |  | |
Fig. 13A

| Obs. mass+Na+ | Theo. mass+ Na+ | Structure | Possible structure connectivity | Type |
|---|---|---|---|---|
| 1542.56 | 1542.6 | (Man)$_3$(GlcNAc)$_5$ | | |
| 1663.6 | 1663.58 | (Hex)$_2$(Man)$_3$(GlcNAc)$_4$ | | |
| 1704.6 | 1704.6 | (Hex)(Man)$_3$(GlcNAc)$_5$ | | |
| 1745.66 | 1745.6 | (Man)$_3$(GlcNAc)$_6$ | | |
| 1866.7 | 1866.7 | (Hex)$_2$(Man)$_3$(GlcNAc)$_5$ | | |
| 1948.7 | 1948.68 | (Man)$_3$(GlcNAc)$_6$ | | |

MONOCLONAL ANTIBODIES AGAINST PROSTATE SPECIFIC MEMBRANE ANTIGEN (PSMA) LACKING IN FUCOSYL RESIDUES

BACKGROUND OF THE INVENTION

Prostate cancer is a leading cause of morbidity and mortality among men. Treatments for prostate cancer include surgery, hormones, radiation, and chemotherapy. There is little effective treatment for metastatic prostate disease. Therefore, the identification of genes and/or gene products that represent diagnostic and prognostic markers, as well as targets for therapy, is critical. Prostate specific antigen (PSA) is one such cancer marker which is useful in the clinical diagnosis and staging of prostate cancer. However, PSA cannot differentiate benign prostatic hyperplasia (BPH) from prostatitis or prostate cancer in the range of 4-10 ng/ml, thus, necessitating a cytologic and/or histologic assessment to confirm the proper diagnosis (Barren, R. J. et al. (1998) Prostate 36:181-188).

Prostate specific membrane antigen (PSMA) is a 750 amino acid, type II transmembrane glycoprotein of approximately 110 kD that has 54% homology to the transferrin receptor. PSMA has 3 structural domains, including a 19 amino acid intracellular domain, a 24 amino acid transmembrane domain, and a 707 amino acid extracellular domain. The PSMA protein displays neurocarboxypeptidase and folate hydrolase activity and is reported to be involved in the neuroendocrine regulation of prostate growth and differentiation (Heston, W. D. (1996) Urologe-Ausgabe A. 35:400-407). PSM' is an alternatively spliced form of PSMA which is localized in the cytoplasm.

PSMA is predominantly expressed by prostatic epithelial cells. The expression of PSMA is increased in prostate cancer, especially in poorly differentiated, metastatic, and hormone refractory carcinomas (Gregorakis, A. K. et al. (1998) Seminars in Urologic Oncology 16:2-12; Silver, D. A. (1997) Clinical Cancer Research 3:81-85). Low level expression of PSMA is observed in extraprostatic tissues such as the small bowel, salivary gland, duodenal mucosa, proximal renal tubules, and brain (Silver, D. A. (1997) Clinical Cancer Research 3:81-85). PSMA is also expressed in endothelial cells of capillary vessels in peritumoral and endotumoral areas of certain malignancies, including renal cell carcinomas, and colon carcinomas, but not in blood vessels from normal tissues. In addition, PSMA is reported to be related to tumor angiogenesis (Silver, D. A. (1997) Clinical Cancer Research 3:81-85).

Antibodies against the extracellular domain of PSMA have been described (see e.g., Liu, H. et al. (1997) Cancer Res. 57:3629-3634; Murphy, G. P. et al. (1998) J. Urol. 160:2396-2401; Wang, S. et al. (2001) Int. J. Cancer 92:871-876; Kato, K. et al. (2003) Int. J. Urol. 10:439-444; U.S. Pat. No. 6,150,508 and U.S. Pat. No. 6,107,090). More recently, human and humanized antibodies that bind PSMA have been described (see e.g., Bander, N. H. et al. (2003) Semin. Oncol. 30:667-676; PCT Publication WO 02/098897; PCT Publication WO 01/09192; PCT Publication WO 03/064606; PCT Publication WO 03/034903; and US Application No. 2004/0033229). Such antibodies have been used for imaging of prostate cancer cells (see e.g., Yao, D. et al. (2002) Semin. Urol. Oncol. 20:211-218; Bander, N. H. et al. (2003) J. Urol. 170:1717-1721). Anti-PSMA antibodies also have been used for therapeutic intervention in treatment of prostate cancer, typically as a conjugate with a chemotherapeutic agent or radioactive isotope (see e.g., Nanus, D. M. et al. (2003) J. Urol. 170:S84-89; Milowsky, M. I. et al. (2004) J. Clin. Oncol. 22:2522-2531; Henry, M. D. et al. (2004) Cancer Res. 64:7995-8001).

Improved therapeutic antibodies against PSMA that are effective for treating and/or preventing diseases involving PSMA expression, particularly antibodies that have cytotoxic effects without the need to be conjugated to a chemotherapeutic agent or radioactive isotope, are desired.

SUMMARY OF THE INVENTION

The present invention provides isolated defucosylated antibodies (i.e., antibodies lacking fucose residues) that bind to human PSMA and exhibit enhanced antibody directed cellular cytotoxic (ADCC) killing of PSMA-expressing cells, as compared to the non-defucosylated form of the antibody (i.e., antibodies containing fucose residues). Also provided are methods for treating a variety of diseases involving PSMA expression using the antibodies and compositions of the invention.

The defucosylated antibodies of the present invention bind to PSMA and inhibit the growth of cells expressing PSMA by enhancing antibody dependent cellular cytotoxicity (ADCC) in the presence of human effector cells (e.g., monocytes or mononuclear cells), as compared to the fucosylated form of the antibody. Accordingly, the antibodies of the present invention provide an improved means for treating disorders characterized by expression of PSMA.

Accordingly, in one aspect, the invention pertains to an isolated anti-prostate specific membrane antigen (PSMA) antibody, which lacks fucose residues. Preferably, the antibody enhances antibody dependent cellular cytotoxicity of cells expressing cell surface PSMA, as compared to a form of the antibody that contains fucose residues. In preferred embodiments, the antibody that lacks fucose residues has an $EC_{50}$ of ADCC activity against LNCaP prostate cancer cells of 0.05 µg/ml or less, or 0.04 µg/ml or less, or 0.03 µg/ml or less, or 0.02 µg/ml or of approximately 0.018 µg/ml or less. In other preferred embodiments, the antibody that lacks fucose residues has an $EC_{50}$ of ADCC activity against LNCaP prostate cancer cells that is at least 3-fold lower (or at least 4-fold lower, or at least 5-fold lower or at least 6-fold lower) than the $EC_{50}$ of ADCC activity against LNCaP prostate cancer cells of the form of the antibody that contains fucose residues.

Preferably, the defucosylated antibody of the invention is a monoclonal antibody. In one aspect, the invention pertains to a humanized or chimeric monoclonal antibody. Preferably, the humanized or chimeric antibody is prepared from a mouse anti-PSMA antibody selected from the group consisting of: 3F5.4G6, 3D7.1.1, 4E10-1.14, 3E11, 4D8, 3E6, 3C9, 2C7, 1G3, 3C4, 3C6, 4D4, 1G9, 5C8B9, 3G6, 4C8B9, E99, J415, J533 and J591. In another aspect, the invention pertains to a human monoclonal antibody.

In a preferred embodiment, the human monoclonal antibody comprises a human heavy chain variable region and a human light chain variable region, wherein:

(a) the human heavy chain variable region comprises an amino acid sequence selected from the group consisting of SEQ ID NOs: 1-9; and (b) the human light chain variable region comprises an amino acid sequence selected from the group consisting of SEQ ID NOs: 10-18.

In various embodiments, the following heavy and light chain combinations are preferred: the human heavy chain variable region comprises the amino acid sequence of SEQ ID NO: 1 and the human light chain variable region comprises the amino acid sequence of SEQ ID NO: 10;

the human heavy chain variable region comprises the amino acid sequence of SEQ ID NO: 2 and the human light chain variable region comprises the amino acid sequence of SEQ ID NO: 11;

the human heavy chain variable region comprises the amino acid sequence of SEQ ID NO: 3 and the human light chain variable region comprises the amino acid sequence of SEQ ID NO: 12;

the human heavy chain variable region comprises the amino acid sequence of SEQ ID NO: 4 and the human light chain variable region comprises the amino acid sequence of SEQ ID NO: 13;

the human heavy chain variable region comprises the amino acid sequence of SEQ ID NO: 5 and the human light chain variable region comprises the amino acid sequence of SEQ ID NO: 14;

the human heavy chain variable region comprises the amino acid sequence of SEQ ID NO: 6 and the human light chain variable region comprises the amino acid sequence of SEQ ID NO: 15;

the human heavy chain variable region comprises the amino acid sequence of SEQ ID NO: 7 and the human light chain variable region comprises the amino acid sequence of SEQ ID NO: 16;

the human heavy chain variable region comprises the amino acid sequence of SEQ ID NO: 8 and the human light chain variable region comprises the amino acid sequence of SEQ ID NO: 17;

the human heavy chain variable region comprises the amino acid sequence of SEQ ID NO: 9 and the human light chain variable region comprises the amino acid sequence of SEQ ID NO: 18.

In another embodiment, a monoclonal antibody of the invention comprises:
- (a) a human heavy chain variable region CDR1 comprising an amino acid sequence selected from the group consisting of SEQ ID NOs: 19-27;
- (b) a human heavy chain variable region CDR2 comprising an amino acid sequence selected from the group consisting of SEQ ID NOs: 28-36;
- (c) a human heavy chain variable region CDR3 comprising an amino acid sequence selected from the group consisting of SEQ ID NOs: 37-45;
- (d) a human light chain variable region CDR1 comprising an amino acid sequence selected from the group consisting of SEQ ID NOs: 46-54;
- (e) a human light chain variable region CDR2 comprising an amino acid sequence selected from the group consisting of SEQ ID NOs: 55-63; and
- (f) a human light chain variable region CDR3 comprising an amino acid sequence selected from the group consisting of SEQ ID NOs: 64-72.

In various embodiments, the following heavy chain and light chain CDR1, CDR2 and CDR3 combinations are preferred:
- (a) a human heavy chain variable region CDR1 comprising SEQ ID NO: 19;
- (b) a human heavy chain variable region CDR2 comprising SEQ ID NO: 28;
- (c) a human heavy chain variable region CDR3 comprising SEQ ID NO: 37;
- (d) a human light chain variable region CDR1 comprising SEQ ID NO: 46;
- (e) a human light chain variable region CDR2 comprising SEQ ID NO: 55; and
- (f) a human light chain variable region CDR3 comprising SEQ ID NO: 64; or
- (a) a human heavy chain variable region CDR1 comprising SEQ ID NO: 20;
- (b) a human heavy chain variable region CDR2 comprising SEQ ID NO: 29;
- (c) a human heavy chain variable region CDR3 comprising SEQ ID NO: 38;
- (d) a human light chain variable region CDR1 comprising SEQ ID NO: 47;
- (e) a human light chain variable region CDR2 comprising SEQ ID NO: 56; and
- (f) a human light chain variable region CDR3 comprising SEQ ID NO: 65; or
- (a) a human heavy chain variable region CDR1 comprising SEQ ID NO: 21;
- (b) a human heavy chain variable region CDR2 comprising SEQ ID NO: 30;
- (c) a human heavy chain variable region CDR3 comprising SEQ ID NO: 39;
- (d) a human light chain variable region CDR1 comprising SEQ ID NO: 48;
- (e) a human light chain variable region CDR2 comprising SEQ ID NO: 57; and
- (f) a human light chain variable region CDR3 comprising SEQ ID NO: 66; or
- (a) a human heavy chain variable region CDR1 comprising SEQ ID NO: 22;
- (b) a human heavy chain variable region CDR2 comprising SEQ ID NO: 31;
- (c) a human heavy chain variable region CDR3 comprising SEQ ID NO: 40;
- (d) a human light chain variable region CDR1 comprising SEQ ID NO: 49;
- (e) a human light chain variable region CDR2 comprising SEQ ID NO: 58; and
- (f) a human light chain variable region CDR3 comprising SEQ ID NO: 67; or
- (a) a human heavy chain variable region CDR1 comprising SEQ ID NO: 23;
- (b) a human heavy chain variable region CDR2 comprising SEQ ID NO: 32;
- (c) a human heavy chain variable region CDR3 comprising SEQ ID NO: 41;
- (d) a human light chain variable region CDR1 comprising SEQ ID NO: 50;
- (e) a human light chain variable region CDR2 comprising SEQ ID NO: 59; and
- (f) a human light chain variable region CDR3 comprising SEQ ID NO: 68; or
- (a) a human heavy chain variable region CDR1 comprising SEQ ID NO: 24;
- (b) a human heavy chain variable region CDR2 comprising SEQ ID NO: 33;
- (c) a human heavy chain variable region CDR3 comprising SEQ ID NO: 42;
- (d) a human light chain variable region CDR1 comprising SEQ ID NO: 51;
- (e) a human light chain variable region CDR2 comprising SEQ ID NO: 60; and
- (f) a human light chain variable region CDR3 comprising SEQ ID NO: 69; or
- (a) a human heavy chain variable region CDR1 comprising SEQ ID NO: 25;
- (b) a human heavy chain variable region CDR2 comprising SEQ ID NO: 34;
- (c) a human heavy chain variable region CDR3 comprising SEQ ID NO: 43;

(d) a human light chain variable region CDR1 comprising SEQ ID NO: 52;
(e) a human light chain variable region CDR2 comprising SEQ ID NO: 61; and
(f) a human light chain variable region CDR3 comprising SEQ ID NO: 70; or
(a) a human heavy chain variable region CDR1 comprising SEQ ID NO: 26;
(b) a human heavy chain variable region CDR2 comprising SEQ ID NO: 35;
(c) a human heavy chain variable region CDR3 comprising SEQ ID NO: 44;
(d) a human light chain variable region CDR1 comprising SEQ ID NO: 53;
(e) a human light chain variable region CDR2 comprising SEQ ID NO: 62; and
(f) a human light chain variable region CDR3 comprising SEQ ID NO: 71; or
(a) a human heavy chain variable region CDR1 comprising SEQ ID NO: 27;
(b) a human heavy chain variable region CDR2 comprising SEQ ID NO: 36;
(c) a human heavy chain variable region CDR3 comprising SEQ ID NO: 45;
(d) a human light chain variable region CDR1 comprising SEQ ID NO: 54;
(e) a human light chain variable region CDR2 comprising SEQ ID NO: 63; and
(f) a human light chain variable region CDR3 comprising SEQ ID NO: 72.

In another aspect, the invention provides a defucosylated human anti-PSMA antibody which comprises a heavy chain variable region that is a product of or derived from a human $V_H$ 5-51 or $V_H$ 3-30.3 gene. The invention also provides a defucosylated human anti-PSMA antibody which comprises a light chain variable region that is a product of or derived from a human $V_k$ L6, 04/014 or L18 gene. The invention still further provides a defucosylated human anti-PSMA antibody which comprises a heavy chain variable region that is a product of or derived from a human $V_H$ 5-51 or $V_H$ 3-30.3 gene and a light chain variable region that is a product of or derived from a human $V_k$ L6, 04/014 or L18 gene.

In another aspect, the invention pertains to a chimeric chicken comprising immunoglobulin heavy and light chain genes encoding an anti-PSMA antibody such that the anti-PSMA antibody is expressed in eggs of the chimeric chicken, wherein the anti-PSMA antibody expressed in the eggs of the chimeric chicken lacks fucose residues. Preferably, the immunoglobulin heavy and light chain genes are human immunoglobulin heavy and light chain genes.

In another aspect, the invention pertains to a host cell comprising immunoglobulin heavy and light chain genes encoding an anti-PSMA antibody, wherein said host cell lacks a fucosyltransferase such that the anti-PSMA antibody expressed by said host cell lacks fucose residues. Preferably, the immunoglobulin heavy and light chain genes are human immunoglobulin heavy and light chain genes. Preferably, the fucosyltransferase is FUT8. Preferably, the host cell is a CHO cell.

In another aspect, the invention provides a method of inhibiting growth of PSMA+ cells. The method involves contacting the cells with a defucosylated anti-PSMA antibody under conditions sufficient to induce antibody-dependent cellular cytoxicity (ADCC) of said cells. The cells can be, for example, tumor cells. Preferably, the anti-PSMA antibody is a human antibody.

The invention also provides a method of inhibiting growth of tumor cells in a subject, wherein the tumor cells or vascular endothelial cells proximate to the tumor cells express PSMA. The method involves administering to the subject a defucosylated anti-PSMA antibody in an amount effective to inhibit growth of the tumor cells in the subject. Preferably, the anti-PSMA antibody is a human antibody. In preferred embodiments, the tumor cells are prostate carcinoma tumor cells.

Other features and advantages of the instant invention will be apparent from the following detailed description and examples which should not be construed as limiting. The contents of all references, Genbank™ entries, patents and published patent applications cited throughout this application are expressly incorporated herein by reference.

BRIEF DESCRIPTION OF THE DRAWINGS

FIG. 1 shows the alignment of the amino acid sequence of the heavy chain variable region of 4A3, 7F12, 8C12, 8A11 and 16F9 (SEQ ID NOs: 1-5, respectively) with the human germline $V_H$ 5-51 amino acid sequence (SEQ ID NO: 73).

FIG. 2 shows the alignment of the amino acid sequence of the light chain variable region of 4A3, 7F12 and 8C12 (SEQ ID NOs: 10-12, respectively) with the human germline $V_k$ L6 amino acid sequence (SEQ ID NO: 74).

FIG. 3 shows the alignment of the amino acid sequence of the light chain variable region of 8A11 and 16F9 (SEQ ID NOs: 13 and 14, respectively) with the human germline $V_k$ 04/014 amino acid sequence (SEQ ID NO: 75).

FIG. 4A shows the nucleotide sequence (SEQ ID NO: 78) and amino acid sequence (SEQ ID NO: 9) of the heavy chain variable region of the 1C3 human monoclonal antibody. The CDR1 (SEQ ID NO: 27), CDR2 (SEQ ID NO: 36) and CDR3 (SEQ ID NO: 45) regions are delineated and the V, D and J germline derivations are indicated.

FIG. 4B shows the nucleotide sequence (SEQ ID NO: 82) and amino acid sequence (SEQ ID NO: 18) of the light chain variable region of the 1C3 human monoclonal antibody. The CDR1 (SEQ ID NO: 54), CDR2 (SEQ ID NO: 63) and CDR3 (SEQ ID NO: 72) regions are delineated and the V and J germline derivations are indicated.

FIG. 5A shows the nucleotide sequence (SEQ ID NO: 79) and amino acid sequence (SEQ ID NO: 6) of the heavy chain variable region of the 2A10 human monoclonal antibody. The CDR1 (SEQ ID NO: 24), CDR2 (SEQ ID NO: 33) and CDR3 (SEQ ID NO: 42) regions are delineated and the V and J germline derivations are indicated.

FIG. 5B shows the nucleotide sequence (SEQ ID NO: 83) and amino acid sequence (SEQ ID NO: 15) of the light chain variable region of the 2A10 human monoclonal antibody. The CDR1 (SEQ ID NO: 51), CDR2 (SEQ ID NO: 60) and CDR3 (SEQ ID NO: 69) regions are delineated and the V and J germline derivations are indicated.

FIG. 6A shows the nucleotide sequence (SEQ ID NO: 80) and amino acid sequence (SEQ ID NO: 7) of the heavy chain variable region of the 2C6 human monoclonal antibody. The CDR1 (SEQ ID NO: 25), CDR2 (SEQ ID NO: 34) and CDR3 (SEQ ID NO: 43) regions are delineated and the V, D, and J germline derivations are indicated.

FIG. 6B shows the nucleotide sequence (SEQ ID NO: 84) and amino acid sequence (SEQ ID NO: 16) of the light chain variable region of the 2C6 human monoclonal antibody. The CDR1 (SEQ ID NO: 52), CDR2 (SEQ ID NO: 61) and CDR3 (SEQ ID NO: 70) regions are delineated and the V and J germline derivations are indicated.

FIG. 7A shows the nucleotide sequence (SEQ ID NO: 81) and amino acid sequence (SEQ ID NO: 8) of the heavy chain variable region of the 2F5 human monoclonal antibody. The CDR1 (SEQ ID NO:26), CDR2 (SEQ ID NO: 35) and CDR3 (SEQ ID NO: 44) regions are delineated and the V, D, and J germline derivations are indicated.

FIG. 7B shows the nucleotide sequence (SEQ ID NO: 85) and amino acid sequence (SEQ ID NO: 17) of the light chain variable region of the 2F5 human monoclonal antibody. The CDR1 (SEQ ID NO: 53), CDR2 (SEQ ID NO: 62) and CDR3 (SEQ ID NO: 71) regions are delineated and the V and J germline derivations are indicated.

FIG. 8 shows the alignment of the amino acid sequence of the heavy chain variable region of 2A10, 2C6 and 2F5 (SEQ ID NOs: 6-8, respectively) with the human germline $V_H$ 5-51 amino acid sequence (SEQ ID NO: 73).

FIG. 9 shows the alignment of the amino acid sequence of the heavy chain variable region of 1C3 (SEQ ID NO: 9) with the human germline $V_H$ 3-30.3 amino acid sequence (SEQ ID NO: 76) and the JH6b germline (SEQ ID NO: 86).

FIG. 10 shows the alignment of the amino acid sequence of the light chain variable region of 2C6 (SEQ ID NO: 16) with the human germline $V_k$ L6 amino acid sequence (SEQ ID NO: 74) and the JK3 germline (SEQ ID NO: 87).

FIG. 11 shows the alignment of the amino acid sequence of the light chain variable region of 1C3, 2A10 and 2F5 (SEQ ID NOs: 18, 15 and 17, respectively) with the human germline $V_k$ L18 amino acid sequence (SEQ ID NO: 77) and the JK4 germline (SEQ ID NO: 88).

FIGS. 13A-13B are summaries of the oligosaccharide structures of the 7F12 anti-PSMA antibody expressed in chicken eggs, as determined by MALDI TOF mass spectrometry. The dark circles represent mannose; the light circles represent hexose (mannose or galactose) and the dark squares represent N-acetyl glucosamine. The vertical line indicates that the last hexose could be connected to any one of the mannose or N-acetyl glucosamine residues along the line.

FIG. 14A shows results using IL-2 stimulated effector cells. FIG. 14B shows results using fresh human peripheral blood effector cells.

FIGS. 16A and 16B represent two independent experiments using LNCaP-C42b target cells and IL-2 stimulated effector cells. FIG. 16C represents an experiment using LNCaP-C42b target cells and fresh human peripheral blood effector cells.

DETAILED DESCRIPTION OF THE INVENTION

Figure 12:
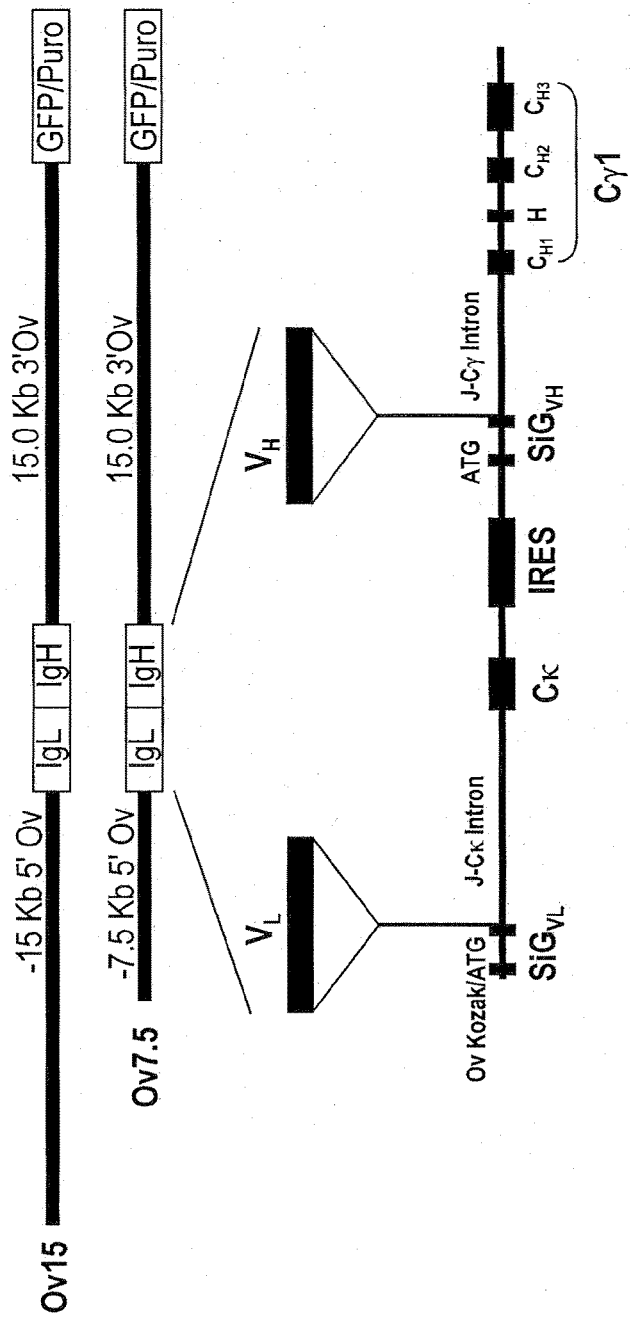
FIG. 12 is a diagram of the Ov7.5 and Ov15 expression vectors. Positions of the 5' and 3' regulatory sequences of Ov are indicated. Included in the 3' end of the vector is a cassette with both EGFP and puromycin (Puro) driven by a promoter (Cx) that functions in all cell types to facilitate isolation of stably transfected lines of cES cells and the identification of the cES cell contribution to the chimeras. Details of the MAb cassette are illustrated in the lower part of the diagram. The thin black line represents intron sequences or non-translated sequences derived from the human L and H chains (although intron sequences are not present in the Ov15Mab7F12 construct). $SiG_{VL}$: sequence for signal peptide of the L chain, VL: sequence for V gene of the L chain, Cκ: sequence for constant region of the Kappa L chain, IRES: internal ribosomal entry sequence, $SiG_{VH}$: sequence for signal peptide of the H chain, VH: sequence for V gene of the H chain, $C_{H1}H$, $C_{H2}$ and $C_{H3}$: coding sequences of the $C_H1$, Hinge, $C_H2$ and $C_H3$ domains of the gamma1 H chain.

The present invention provides antibody compositions and improved antibody-based therapies for treating and diagnosing a variety of disorders associated with PSMA expression and/or PSMA expressing cells. The antibodies of the invention lack fucosyl residues on the antibody carbohydrate chains. Furthermore, the antibodies exhibit enhanced antibody directed cellular cytotoxic (ADCC) killing of PSMA+ cells.

In particular embodiments, the antibodies of the present invention are humanized or fully human antibodies and are particularly useful for the therapeutic treatment in humans of disorders associated with PSMA expressing cells. Methods of using anti-PSMA antibodies lacking fucosyl residues for therapeutic treatment (e.g., to treat and/or prevent diseases associated with expression of PSMA) are also encompassed by the invention.

In order that the present invention may be more readily understood, certain terms will be defined as follows. Additional definitions are set forth throughout the detailed description.

The terms "prostate specific membrane antigen" and "PSMA" are used Interchangeably herein, and include any variants, isoforms and species homologs of human PSMA that are naturally expressed by cells and that retain binding to the antibodies 4A3, 7F12, 8C12, 8A11, 16F9, 2A10, 2C6, 2F5 and 1C3 described herein. The complete amino acid sequence of human PSMA protein has the Genbank™ accession number NP_004467. The complete cDNA sequence encoding the human PSMA protein has the Genbank™ accession number NM_004476.

As used herein, the terms "antibody that lacks fucose residues" and "defucosylated antibody" are used interchangeably and are intended to refer to an antibody in which the carbohydrate portion of the antibody does not contain a fucosyl residue or from which the fucosyl residue has been removed. An antibody that lacks fucose residues can be generated, for example, by expression of the antibody in a cell or expression system that minimizes or does not attach fucosyl residues to the antibody carbohydrate chain, or by chemical modification of the antibody to remove fucosyl residues from the carbohydrate chain (e.g., treatment of the antibody with a fucosidase). As such, the terms "lacks fucose residues" and "defucosylated" are not intended to be limited by the mechanism by which the antibody with altered carbohydrate structure is prepared.

As used herein, the term "antibody expressing fucose residues" and "fucosylated antibody" are used interchangeably and are intended to refer to an antibody in which the carbohydrate portion of the antibody contains fucose.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

As used herein, the term "effector cell" refers to an immune cell which is involved in the effector phase of an immune response, as opposed to the cognitive and activation phases of an immune response. Exemplary immune cells include a cell of a myeloid or lymphoid origin, e.g., lymphocytes (e.g., B cells and T cells including cytolytic T cells (CTLs)), killer cells, natural killer cells, macrophages, monocytes, eosinophils, neutrophils, polymorphonuclear cells, granulocytes, mast cells, and basophils. Some effector cells express specific Fc receptors and carry out specific immune functions. In preferred embodiments, an effector cell is capable of inducing antibody-dependent cell-mediated cytotoxicity (ADCC), e.g., a neutrophil capable of inducing ADCC. For example, monocytes and macrophages, which express FcR are involved in specific killing of target cells and presenting antigens to other components of the immune system, or binding to cells that present antigens. In other embodiments, an effector cell can phagocytose a target antigen or target cell. The expression of a particular FcR on an effector cell can be regulated by humoral factors such as cytokines. For example, expression of FcαRI has been found to be up-regulated by G-CSF or GM-CSF. This enhanced expression increases the effector function of FcαRI-bearing cells against targets. An effector cell can phagocytose or lyse a target antigen or a target cell.

"Target cell" refers to any cell or pathogen whose elimination would be beneficial in a subject (e.g., a human or animal) and that can be targeted by a composition (e.g., antibody) of the invention. For example, the target cell can be a cell expressing or overexpressing PSMA.

The term "antibody-dependent cellular cytotoxicity" or "ADCC" refers to a cell-mediated cytotoxic reaction in which a PSMA+ target cell with bound anti-PSMA antibody is recognized by an effector cell bearing Fc receptors and is subsesquently lysed without requiring the involvement of complement.

As used herein, the term "enhances ADCC" (e.g., referring to cells) is intended to include any measurable increase in cell lysis when contacted with an anti-PSMA antibody lacking fucosyl residues as compared to the cell killing of the same cell in contact with a fucosylated anti-PSMA antibody in the presence of effector cells (for example, at a ratio of target cells:effector cells of 1:50), e.g., an increase in cell lysis by at least about 10%, 20%, 30%, 40%, 50%, 60%, 70%, 80%, 90%, 100%, 150%, 200%, 250%, 300%, or 325%.

The term "antibody" as referred to herein includes whole antibodies and any antigen binding fragment (i.e., "antigen-binding portion") or single chains thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion"), as used herein, refers to one or more fragments of an antibody that retain the ability to specifically bind to an antigen (e.g., PSMA). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to refer to antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo).

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell. The term "human monoclonal antibody", as used herein, also includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

An "isolated antibody," as used herein, is intended to refer to an antibody which is substantially free of other antibodies having different antigenic specificities (e.g., an isolated antibody that specifically binds to PSMA is substantially free of antibodies that specifically bind antigens other than PSMA). An isolated antibody that specifically binds to an epitope, isoform or variant of human PSMA may, however, have cross-reactivity to other related antigens, e.g., from other species (e.g., PSMA species homologs). Moreover, an isolated antibody may be substantially free of other cellular material and/or chemicals. In one embodiment of the invention, a combination of "isolated" monoclonal antibodies having different specificities are combined in a well defined composition.

The term "humanized antibody" is intended to refer to antibodies in which CDR sequences derived from the germline of another mammalian species, such as a mouse, have been grafted onto human framework sequences. Additional framework region modifications may be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

The term "epitope" means a protein determinant capable of specific binding to, or specific binding by, an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

As used herein, "specific binding" refers to antibody binding to a predetermined antigen. Typically, the antibody binds with a dissociation constant ($K_D$) of $10^{-7}$M or less, and binds to the predetermined antigen with a $K_D$ that is at least two-fold less than its $K_D$ for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen".

As used herein, "isotype" refers to the antibody class (e.g., IgM or IgG1) that is encoded by heavy chain constant region genes.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, CHO cells, transfectomas, and lymphocytic cells.

As used herein, the term "subject" includes any human or nonhuman animal. The term "nonhuman animal" includes all vertebrates, e.g., mammals and non-mammals, such as nonhuman primates, sheep, dogs, cats, horses, cows, chickens, amphibians, reptiles, etc.

The terms "transgenic, nonhuman animal" refers to a nonhuman animal having a genome comprising one or more human heavy and/or light chain transgenes or transchromosomes (either integrated or non-integrated into the animal's natural genomic DNA) and which is capable of expressing fully human antibodies. For example, a transgenic mouse can have a human light chain transgene and either a human heavy chain transgene or human heavy chain transchromosome, such that the mouse produces human anti-PSMA antibodies when immunized with PSMA antigen and/or cells expressing PSMA. The human heavy chain transgene can be integrated into the chromosomal DNA of the mouse, as is the case for transgenic, e.g., HuMAb mice, or the human heavy chain transgene can be maintained extrachromosomally, as is the case for transchromosomal (e.g., KM) mice as described in WO 02/43478. Such transgenic and transchromosomal mice are capable of producing multiple isotypes of human monoclonal antibodies to PSMA (e.g., IgG, IgA and/or IgE) by undergoing V-D-J recombination and isotype switching.

Various aspects of the invention are described in further detail in the following subsections.

Anti-PSMA Antibodies Lacking Fucose Residues and Having Enhanced ADCC Activity

The present invention relates to a defucosylated anti-PSMA antibody with enhanced antibody directed cellular cytotoxicity (ADCC) against cells expressing PSMA as compared to the fucosylated form of the antibody. In a preferred embodiment, a defucosylated antibody of the invention enhances ADCC of LnCaP prostate carcinoma cells (ATCC® CRL-1740™) in vitro compared to the fucosylated form of the antibody, for example under conditions of an antibody concentration of 0.1 µg/ml and a target cell to effector cell ratio of 1:100. Preferably, the effector cells used are IL-2 stimulated effector cells from human peripheral blood (e.g., $1 \times 10^6$ human peripheral blood mononuclear cells are incubated with 10 U/ml of human IL-2 overnight at 37° C.). The defucosylated form of the antibody preferably is compared to a fucosylated form that is obtained from expression in mammalian host cells, such as CHO cells.

In preferred embodiments, the defucosylated form of the antibody has an $EC_{50}$ for ADCC activity of 0.05 µg/ml or less, more preferably 0.04 µg/ml or less, even more preferably 0.03 µg/ml or less, even more preferably 0.02 µg/ml or less, and even more preferably an $EC_{50}$ of approximately 0.018 µg/ml. In other preferred embodiments, the defucosylated form of the antibody has an $EC_{50}$ for ADCC activity of 0.01 µg/ml or less, more preferably 0.009 µg/ml or less, even more preferably 0.008 µg/ml or less, even more preferably 0.007 µg/ml or less, even more preferably 0.005 µg/ml or less and even more preferably an $EC_{50}$ of approximately 0.002 µg/ml. Preferably, the $EC_{50}$ for ADCC activity is determined using the assay described in Example 4 and using IL-2 stimulated effector cells or using the assay described in Example 4 and using fresh human peripheral blood effector cells.

In other preferred embodiments, the defucosylated form of the antibody has an $EC_{50}$ for ADCC activity that is at least 3-fold less than the $EC_{50}$ of the fucosylated form of the antibody (e.g., a CHO cell-expressed form of the antibody), more preferably at least 4-fold less than the $EC_{50}$ of the fucosylated form of the antibody, even more preferably at least 5-fold less than the $EC_{50}$ of the fucosylated form of the antibody, even more preferably at least 6-fold less than the $EC_{50}$ of the fucosylated form of the antibody, even more preferably at least 7-fold less than the $EC_{50}$ of the fucosylated form of the antibody, even more preferably at least 8-fold less than the $EC_{50}$ of the fucosylated form of the antibody, even more preferably at least 9-fold less than the $EC_{50}$ of the fucosylated form of the antibody and even more preferably at least 10-fold less than the $EC_{50}$ of the fucosylated form of the antibody. Again, preferably, the $EC_{50}$ for ADCC activity is determined using the assay described in Example 4 and using IL-2 stimulated effector cells or using the assay described in Example 4 and using fresh human peripheral blood effector cells. Typically, the ratio of EC50 (fucosylated):EC50 (defucosylated) was found to be greater using the fresh human peripheral blood effector cells, although the maximum percent lysis was found to be less using the fresh peripheral blood effector cells.

The increased ADCC activity of a defucosylated antibody of the invention can be quantitated, for example, as an increase in percent cell lysis, as compared to the fucosylated form of the antibody, when ADCC activity is measured under the same conditions for the defucosylated and fucosylated forms (e.g., same antibody concentrations and same target to effector cell ratios). Additionally or alternatively, the increased ADCC activity of a defucosylated antibody of the invention can be quantitated, for example, as an increased potency as measured by a decrease in the $EC_{50}$ value for the defucosylated form, as compared to the fucosylated form. This can be quantitated by the ratio of the $EC_{50}$ for the fucosylated form to the defucosylated form.

Examples of PSMA+ cell lines that can be used in the ADCC assays of the invention and against which a defucosylated antibody of the invention exhibits enhanced ADCC activity, as compared to the fucosylated form of the antibody, include LnCaP cells, 22Rv1 cells and/or PCa2b cells. The enhanced ADCC effect by defucosylated anti-PSMA antibodies may result in ADCC activity on PSMA+ cells at antibody concentrations where ADCC would not be observed with the fucosylated form of the antibody.

Defucosylation of Anti-PSMA Antibodies

Anti-PSMA antibodies (e.g., murine, chimeric, humanized and human antibodies) are known in the art, and may be used in the present invention. The anti-PSMA antibody of the present invention is modified such that the antibody is lacking in fucosyl residues. An antibody can be made that is lacking in fucosyl residues by one of a variety of methods. For example, the antibody can expressed, using recombinant DNA technology, in a cell with an altered glycosylation mechanism such that addition of fucosyl residues to carbohydrate chains is inhibited. Additionally or alternatively, an antibody can be defucosylated through chemical removal of the fucosyl residue.

Still further, in a preferred embodiment, the antibody can be expressed in a chimeric chicken expression system, such that the antibody is produced in the eggs of the chimeric chicken. Preparation of chimeric chickens that express anti-PSMA antibody in the eggs of the chicken are described in detail in Example 1 and the lack of fucose residues on such chicken egg-expressed anti-PSMA antibodies is demonstrated in Example 3. Chimeric chickens suitable for use in expressing proteins in the eggs of the chicken are described in PCT Publication WO 2004/015123. Accordingly, in another aspect, the invention pertains to a chimeric chicken comprising immunoglobulin heavy and light chain genes encoding an anti-PSMA antibody such that the anti-PSMA antibody is expressed in eggs of the chimeric chicken, wherein the anti-PSMA antibody expressed in the eggs of the chimeric chicken lacks fucose residues. Preferably, the immunoglobulin heavy and light chain genes are human immunoglobulin heavy and light chain genes.

In another embodiment, the antibody is expressed in a cell that is lacking in a fucosyltransferase enzyme such that the cell line produces proteins lacking fucose in their carbohydrates (see Examples 5 and 6). For example, the cell lines Ms704, Ms705, and Ms709 lack the fucosyltransferase gene, FUT8 (alpha (1,6) fucosyltransferase), such that antibodies expressed in the Ms704, Ms705, and Ms709 cell lines lack fucose on their carbohydrates. The Ms704, Ms705, and Ms709 FUT8$^{-/-}$ cell lines were created by the targeted disruption of the FUT8 gene in CHO/DG44 cells using two replacement vectors (see U.S. Patent Publication No. 20040110704 by Yamane et al. and Yamane-Ohnuki et al. (2004) *Biotechnol Bioeng* 87:614-22). As another example, EP 1,176,195 by Hanai et al. describes a cell line with a functionally disrupted FUT8 gene, which encodes a fucosyl transferase, such that antibodies expressed in such a cell line exhibit hypofucosylation by reducing or eliminating the alpha 1,6 bond-related enzyme. Hanai et al. also describe cell lines which naturally have a low enzyme activity for adding fucose to the N-acetylglucosamine that binds to the Fc region of the antibody or does not have the enzyme activity, for example the rat myeloma cell line YB2/0 (ATCC® CRL 1662™). PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al. (2002) *J. Biol. Chem.* 277:26733-26740). PCT Publication WO 99/54342 by Umana et al. describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) *Nat. Biotech.* 17:176-180).

In another embodiment, an anti-PSMA antibody is expressed and the fucosyl residue(s) is cleaved using a fucosidase enzyme. For example, the fucosidase alpha-L-fucosidase removes fucosyl residues from antibodies (Tarentino, A. L. et al. (1975) *Biochem.* 14:5516-23).

Additionally, in other embodiments, other forms of glycosylation of an antibody are also modified. For example, an aglycoslated antibody can be made (i.e., the antibody lacks glycosylation). Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Characterization of Absence of Fucosyl Residues on Anti-PSMA Antibodies

Antibodies of the invention lack fucosyl residues, for example in the Fc portion carbohydrate chain. Antibodies can be tested for the absence of fucosyl residues using standard techniques known in the art, such as APTS capillary electrophoresis laser induced fluorescence. Briefly, the N-linked oligosaccharides of the purified anti-PSMA antibody can be released by adding the peptide N-glycanase (Prozyme™) and incubating overnight. The carbohydrates are resuspended and derivatized with 8-aminopyrene-1,3,6-trisulfonate (APTS) under mild reductive amination conditions in which desialylation and loss of fucosyl residues is minimized. The reaction adducts are analyzed by capillary electrophoresis with a laser-induced fluorescence detector (Beckman Coulter). An absence of fucose can be observed by a shift in the electrophoresis compared to the same antibody containing fucose. Another technique for testing the absence of fucose on anti-PSMA antibodies is a monosaccharide analysis using HPLC. Other techniques for analyzing the carbohydrate content and structure for the antibody include MS profiling of expressed carbohydrates (glycomics), direct MALDI-TOF analysis of released intact glycans (to provide the mass of classes of carbohydrates), low CID MSMS spectra (to provide structure composition of the glycans), high CID MSMS spectra and MSn spectra (to provide information about the connectivity of the glycans) and sequential exoglycosidase digestion (to provide structure connectivity information of the glycans). Methodologies for examining the carbohydrate content of antibodies are described in detail in Example 3.

Characterization of Antibody Dependent Cell Killing of PSMA+ Cells

Defucosylated anti-PSMA antibodies can be tested for their ability to mediate phagocytosis and killing of cells expressing PSMA. In one embodiment, a defucosylated anti-PSMA antibody enhances killing of cells expressing PSMA in comparison to the same antibody containing fucose when compared at the same concentration. In another embodiment, a defucosylated anti-PSMA antibody induces killing of cells expressing PSMA where the same antibody containing fucose does not induce cell killing at the same concentration.

The ADCC activity of a monoclonal antibody can be tested in established in vitro assays. As an example, a chromium release ADCC assay may be used. Briefly, peripheral blood mononuclear cells (PBMCs), or other effector cells, from healthy donors can be purified by Ficoll Hypaque density centrifugation, followed by lysis of contaminating erythrocytes. Washed PBMCs can be suspended in RPMI supplemented with 10% heat-inactivated fetal calf serum and mixed with $^{51}$Cr labeled cells expressing PSMA, at various ratios of effector cells to tumor cells (effector cells:tumor cells). Anti-PSMA antibody can then be added at various concentrations. An isotype matched antibody can be used as a negative control. Assays can be carried out for 4-18 hours at 37° C. Samples can be assayed for cytolysis by measuring $^{51}$Cr release into the culture supernatant. Anti-PSMA monoclonal can also be tested in combinations with each other to determine whether cytolysis is enhanced with multiple monoclonal antibodies.

An alternative assay that can be used to test for anti-PSMA antibody ability to mediate phagocytosis and killing of cells expressing PSMA is a time resolved fluorometry assay. Briefly, PSMA expressing cells are loaded with an acetoxymethyl ester of fluorescence enhancing ligand (BATDA), which penetrates cell membranes. Inside the cell, the ester bonds are hydrolized and the compound can no longer pass the cell membrane. Anti-PSMA antibody can then be added at various concentrations. Following cytolysis, an europeum solution (Perkin Elmer) is added and any free ligand binds the europeum to form a highly fluorescent and stable chelate (EuTDA) that can be read on a microplate reader (Perkin Elmer). The measured signal correlates with the amount of lysed cells.

Preferred ADCC assays for examining the ADCC activity of the anti-PSMA antibodies of the invention are described in detail in Example 4.

Anti-PSMA antibodies also can be tested in an in vivo model (e.g., in mice) to determine their efficacy in mediating phagocytosis and killing of cells expressing PSMA, e.g., tumor cells. These antibodies can be selected, for example, based on the following criteria, which are not intended to be exclusive:

1) binding to live cells expressing PSMA;
2) high affinity of binding to PSMA;
3) binding to a unique epitope on PSMA (to eliminate the possibility that monoclonal antibodies with complimentary activities when used in combination would compete for binding to the same epitope);
4) internalization by cells expressing PSMA;

5) mediation of in vitro of growth inhibition, phagocytosis and/or killing of cells expressing PSMA in the presence of human effector cells.

Preferred monoclonal antibodies of the invention meet one or more of these criteria. In a particular embodiment, the monoclonal antibodies are used in combination, e.g., as a pharmaceutical composition comprising two or more anti-PSMA monoclonal antibodies or fragments thereof. For example, anti-PSMA monoclonal antibodies having different, but complementary activities can be combined in a single therapy to achieve a desired therapeutic or diagnostic effect. An illustration of this would be a composition containing an anti-PSMA monoclonal antibody that mediates highly effective killing of target cells in the presence of effector cells, combined with another anti-PSMA monoclonal antibody that inhibits the growth of cells expressing PSMA.

Characterization of Binding to PSMA

Antibodies of the invention can be tested for binding to PSMA by, for example, standard assays known in the art, such as ELISA, FACS analysis and/or Biacore™ analysis. In a typical ELISA assay, briefly, microtiter plates are coated with purified PSMA at 0.25 µg/ml in PBS, and then blocked with 5% bovine serum albumin in PBS. Dilutions of antibody are added to each well and incubated for 1-2 hours at 37° C. The plates are washed with PBS/Tween and then incubated with secondary reagent (e.g., for human antibodies or a goat-anti-human IgG Fc-specific polyclonal reagent) conjugated to alkaline phosphatase for 1 hour at 37° C. After washing, the plates are developed with pNPP substrate (1 mg/ml), and analyzed at OD of 405-650.

In order to demonstrate binding of monoclonal antibodies to live cells expressing the PSMA, flow cytometry can be used. In a typical (but non-limiting) example of a flow cytometry protocol, cell lines expressing PSMA (grown under standard growth conditions) are mixed with various concentrations of monoclonal antibodies in PBS containing 0.1% BSA and 20% mouse serum, and incubated at 37° C. for 1 hour. After washing, the cells are reacted with Fluorescein-labeled secondary antibody (e.g., anti-human IgG antibody) under the same conditions as the primary antibody staining. The samples can be analyzed by a FACScan™ instrument using light and side scatter properties to gate on single cells. An alternative assay using fluorescence microscopy may be used (in addition to or instead of) the flow cytometry assay. Cells can be stained exactly as described above and examined by fluorescence microscopy. This method allows visualization of individual cells, but may have diminished sensitivity depending on the density of the antigen.

Anti-PSMA antibodies can be further tested for reactivity with PSMA antigen by Western blotting. For example, cell extracts from cells expressing PSMA can be prepared and subjected to sodium dodecyl sulfate (SDS) polyacrylamide gel electrophoresis. After electrophoresis, the separated antigens are transferred to nitrocellulose membranes, blocked with 20% mouse serum, and probed with the monoclonal antibodies to be tested. Antibody binding can be detected using anti-species specific secondary antibody linked to alkaline phosphatase and developed with BCIP/NBT substrate tablets (Sigma® Chem. Co., St. Louis, Mo.). Other techniques for evaluating the binding ability of antibodies towards PSMA are known in the art, including RIAs and Biacore™ analysis. Suitable assays to determine PSMA binding are described in detail in Example 4.

Chimeric or Humanized Anti-PSMA Antibodies

In certain embodiments, a defucosylated anti-PSMA antibody of the invention is a chimeric or humanized antibody. Such antibodies can be prepared using mouse anti-PSMA antibodies that are available in the art and established procedures for converting a mouse antibody to a chimeric or humanized antibody. Non-limiting examples of such mouse anti-PSMA antibodies include the 3F5.4G6, 3D7.1.1, 4E10-1.14, 3E11, 4D8, 3E6, 3C9, 2C7, 1G3, 3C4, 3C6, 4D4, 1G9, 5C8B9, 3G6, 4C8B9, E99, J415, J533 and J591 monoclonal antibodies. Hybridomas secreting 3F5.4G6, 3D7.1.1, 4E10-1.14, 3E11, 4D8, 3E6, 3C9, 2C7, 1G3, 3C4, 3C6, 4D4, 1G9, 5C8B9, 3G6 or 4C8B9 have been publicly deposited and are described in U.S. Pat. No. 6,159,508. Hybridomas secreting E99, J415, J533 or J591 have been publicly deposited and are described in U.S. Pat. No. 6,107,090. Moreover, humanized anti-PSMA antibodies, including a humanized version of J591, are described in further detail in PCT Publication WO 02/098897. Furthermore, other mouse anti-human PSMA antibodies have been described in the art, such as mAb 107-1A4 (Wang, S. et al. (2001) Int. J. Cancer 92:871-876) and mAb 2C9 (Kato, K. et al. (2003) Int. J. Urol. 10:439-444).

Human Monoclonal Anti-PSMA Antibodies

Preferred antibodies of the invention include human anti-PSMA monoclonal antibodies. Examples of human anti-PSMA monoclonal antibodies include the 4A3, 7F12, 8C12, 8A11, 16F9, 2A10, 2C6, 2F5 and 1C3 antibodies, isolated and structurally characterized as originally described in PCT Publications WO 01/09192 and WO 03/064606 and in U.S. Provisional Application Ser. No. 60/654,125, entitled "Human Monoclonal Antibodies to Prostate Specific Membrane Antigen (PSMA)", filed on Feb. 18, 2005, the contents of each of which are expressly incorporated herein by reference. The $V_H$ amino acid sequences of 4A3, 7F12, 8C12, 8A11, 16F9, 2A10, 2C6, 2F5 and 1C3 are shown in SEQ ID NOs: 1-9, respectively. The $V_L$ amino acid sequences of 4A3, 7F12, 8C12, 8A11, 16F9, 2A10, 2C6, 2F5 and 1C3 are shown in SEQ ID NOs: 10-18, respectively. Other human anti-PSMA antibodies that can be used in the invention include the antibodies disclosed in PCT Publication WO 03/034903 and US Application No. 2004/0033229.

Given that each of these antibodies can bind to PSMA, the $V_H$ and $V_L$ sequences can be "mixed and matched" to create other anti-PSMA binding molecules of the invention. PSMA binding of such "mixed and matched" antibodies can be tested using the binding assays well known in the art, such as FACS analysis and ELISA assays. Preferably, when $V_H$ and $V_L$ chains are mixed and matched, a $V_H$ sequence from a particular $V_H/V_L$ pairing is replaced with a structurally similar $V_H$ sequence Likewise, preferably a $V_L$ sequence from a particular $V_H/V_L$ pairing is replaced with a structurally similar $V_L$ sequence. For example, the $V_H$ sequences of 4A3, 7F12, 8C12, 8A11, 16F9, 2A10, 2C6 and 2F5 are particularly amenable for mixing and matching, since these antibodies use $V_H$ sequences derived from the same germline sequence ($V_H$ 5-51) and thus they exhibit structural similarity. Likewise, the $V_L$ sequences of 4A3, 7F12, 8C12, and 2C6 are particularly amenable for mixing and matching, since these antibodies use $V_L$ sequences derived from the same germline sequence ($V_L$ L6) and thus they exhibit structural similarity. Likewise, the $V_L$ sequences of 8A11 and 16F9 are particularly amenable for mixing and matching, since these antibodies use $V_L$ sequences derived from the same germline sequence ($V_L$ 04/014) and thus they exhibit structural similarity. Likewise, the $V_L$ sequences of 1C3, 2A10 and 2F5 are particularly amenable for mixing and matching, since these antibodies use $V_L$ sequences derived from the same germline sequence ($V_L$ L18) and thus they exhibit structural similarity.

In particular embodiments, the invention provides a defucosylated monoclonal antibody, or antigen binding portion thereof, comprising:

(a) a heavy chain variable region comprising an amino acid sequence selected from the group consisting of SEQ ID NOs: 1-9; and (b) a light chain variable region comprising an amino acid sequence selected from the group consisting of SEQ ID NO: 10-18;

wherein the antibody specifically binds human PSMA.
Preferred heavy and light chain combinations include:

(a) a heavy chain variable region comprising the amino acid sequence of SEQ ID NO: 1; and (b) a light chain variable region comprising the amino acid sequence of SEQ ID NO: 10; or (a) a heavy chain variable region comprising the amino acid sequence of SEQ ID NO: 2; and (b) a light chain variable region comprising the amino acid sequence of SEQ ID NO: 11; or (a) a heavy chain variable region comprising the amino acid sequence of SEQ ID NO: 3; and (b) a light chain variable region comprising the amino acid sequence of SEQ ID NO: 12.

(a) a heavy chain variable region comprising the amino acid sequence of SEQ ID NO: 4; and (b) a light chain variable region comprising the amino acid sequence of SEQ ID NO: 13; or (a) a heavy chain variable region comprising the amino acid sequence of SEQ ID NO: 5; and (b) a light chain variable region comprising the amino acid sequence of SEQ ID NO: 14; or (a) a heavy chain variable region comprising the amino acid sequence of SEQ ID NO: 6; and (b) a light chain variable region comprising the amino acid sequence of SEQ ID NO: 15; or (a) a heavy chain variable region comprising the amino acid sequence of SEQ ID NO: 7; and (b) a light chain variable region comprising the amino acid sequence of SEQ ID NO: 16; or (a) a heavy chain variable region comprising the amino acid sequence of SEQ ID NO: 8; and (b) a light chain variable region comprising the amino acid sequence of SEQ ID NO: 17; or (a) a heavy chain variable region comprising the amino acid sequence of SEQ ID NO: 9; and (b) a light chain variable region comprising the amino acid sequence of SEQ ID NO: 18.

In another aspect, the invention provides defucosylated antibodies that comprise the heavy chain and light chain CDR1s, CDR2s and CDR3s of 4A3, 7F12, 8C12, 8A11, 16F9, 2A10, 2C6, 2F5 or 1C3, or combinations thereof. The amino acid sequences of the $V_H$ CDR1s of 4A3, 7F12, 8C12, 8A11, 16F9, 2A10, 2C6, 2F5 and 1C3 are shown in SEQ ID NOs: 19-27, respectively. The amino acid sequences of the $V_H$ CDR2s of 4A3, 7F12, 8C12, 8A11, 16F9, 2A10, 2C6, 2F5 and 1C3 are shown in SEQ ID NOs: 28-36, respectively. The amino acid sequences of the $V_H$ CDR3s of 4A3, 7F12, 8C12, 8A11, 16F9, 2A10, 2C6, 2F5 and 1C3 are shown in SEQ ID NOs: 37-45, respectively. The amino acid sequences of the $V_K$ CDR1s of 4A3, 7F12, 8C12, 8A11, 16F9, 2A10, 2C6, 2F5 and 1C3 are shown in SEQ ID NOs: 46-54, respectively. The amino acid sequences of the $V_K$ CDR2s of 4A3, 7F12, 8C12, 8A11, 16F9, 2A10, 2C6, 2F5 and 1C3 are shown in SEQ ID NOs: 55-63, respectively. The amino acid sequences of the $V_K$ CDR3s of 4A3, 7F12, 8C12, 8A11, 16F9, 2A10, 2C6, 2F5 and 1C3 are shown in SEQ ID NOs: 64-72, respectively. The CDR regions are delineated using the Kabat system (Kabat, E. A., et al. (1991) *Sequences of Proteins of Immunological Interest*, Fifth Edition, U.S. Department of Health and Human Services, NIH Publication No. 91-3242).

Given that each of these antibodies can bind to PSMA and that antigen-binding specificity is provided primarily by the CDR1, 2 and 3 regions, the $V_H$ CDR1, 2 and 3 sequences and $V_k$ CDR1, 2 and 3 sequences can be "mixed and matched" (i.e., CDRs from different antibodies can be mixed and match, although each antibody must contain a $V_H$ CDR1, 2 and 3 and a $V_k$ CDR1, 2 and 3) to create other anti-PSMA binding molecules of the invention. PSMA binding of such "mixed and matched" antibodies can be tested using binding assays know in the art, for example, FACS analysis and ELISA assays. Preferably, when $V_H$ CDR sequences are mixed and matched, the CDR1, CDR2 and/or CDR3 sequence from a particular $V_H$ sequence is replaced with a structurally similar CDR sequence(s). Likewise, when $V_k$ CDR sequences are mixed and matched, the CDR1, CDR2 and/or CDR3 sequence from a particular $V_k$ sequence preferably is replaced with a structurally similar CDR sequence(s). It will be readily apparent to the ordinarily skilled artisan that novel $V_H$ and $V_L$ sequences can be created by substituting one or more $V_H$ and/or $V_L$ CDR region sequences with structurally similar sequences from the CDR sequences disclosed herein for monoclonal antibodies 4A3, 7F12, 8C12, 8A11, 16F9, 2A10, 2C6, 2F5 and 1C3.

Accordingly, in another aspect, the invention provides a defucosylated monoclonal antibody, or antigen binding portion thereof comprising:

(a) a heavy chain variable region CDR1 comprising an amino acid sequence selected from the group consisting of SEQ ID NOs: 19-27;

(b) a heavy chain variable region CDR2 comprising an amino acid sequence selected from the group consisting of SEQ ID NOs: 28-36;

(c) a heavy chain variable region CDR3 comprising an amino acid sequence selected from the group consisting of SEQ ID NOs: 37-45;

(d) a light chain variable region CDR1 comprising an amino acid sequence selected from the group consisting of SEQ ID NOs: 46-54;

(e) a light chain variable region CDR2 comprising an amino acid sequence selected from the group consisting of SEQ ID NOs: 55-63; and (f) a light chain variable region CDR3 comprising an amino acid sequence selected from the group consisting of SEQ ID NOs: 64-72;

wherein the antibody specifically binds PSMA.

In a preferred embodiment, the antibody comprises:
(a) a human heavy chain variable region CDR1 comprising SEQ ID NO: 19;
(b) a human heavy chain variable region CDR2 comprising SEQ ID NO: 28;
(c) a human heavy chain variable region CDR3 comprising SEQ ID NO: 37;
(d) a human light chain variable region CDR1 comprising SEQ ID NO: 46;
(e) a human light chain variable region CDR2 comprising SEQ ID NO: 55; and
(f) a human light chain variable region CDR3 comprising SEQ ID NO: 64.

In another preferred embodiment, the antibody comprises:
(a) a human heavy chain variable region CDR1 comprising SEQ ID NO: 20;
(b) a human heavy chain variable region CDR2 comprising SEQ ID NO: 29;
(c) a human heavy chain variable region CDR3 comprising SEQ ID NO: 38;
(d) a human light chain variable region CDR1 comprising SEQ ID NO: 47;

(e) a human light chain variable region CDR2 comprising SEQ ID NO: 56; and
(f) a human light chain variable region CDR3 comprising SEQ ID NO: 65.

In another preferred embodiment, the antibody comprises:
(a) a human heavy chain variable region CDR1 comprising SEQ ID NO: 21;
(b) a human heavy chain variable region CDR2 comprising SEQ ID NO: 30;
(c) a human heavy chain variable region CDR3 comprising SEQ ID NO: 39;
(d) a human light chain variable region CDR1 comprising SEQ ID NO: 48;
(e) a human light chain variable region CDR2 comprising SEQ ID NO: 57; and
(f) a human light chain variable region CDR3 comprising SEQ ID NO: 66.

In another preferred embodiment, the antibody comprises:
(a) a human heavy chain variable region CDR1 comprising SEQ ID NO: 22;
(b) a human heavy chain variable region CDR2 comprising SEQ ID NO: 31;
(c) a human heavy chain variable region CDR3 comprising SEQ ID NO: 40;
(d) a human light chain variable region CDR1 comprising SEQ ID NO: 49;
(e) a human light chain variable region CDR2 comprising SEQ ID NO: 58; and
(f) a human light chain variable region CDR3 comprising SEQ ID NO: 67.

In another preferred embodiment, the antibody comprises:
(a) a human heavy chain variable region CDR1 comprising SEQ ID NO: 23;
(b) a human heavy chain variable region CDR2 comprising SEQ ID NO: 32;
(c) a human heavy chain variable region CDR3 comprising SEQ ID NO: 41;
(d) a human light chain variable region CDR1 comprising SEQ ID NO: 50;
(e) a human light chain variable region CDR2 comprising SEQ ID NO: 59; and
(f) a human light chain variable region CDR3 comprising SEQ ID NO: 68.

In another preferred embodiment, the antibody comprises:
(a) a human heavy chain variable region CDR1 comprising SEQ ID NO: 24;
(b) a human heavy chain variable region CDR2 comprising SEQ ID NO: 33;
(c) a human heavy chain variable region CDR3 comprising SEQ ID NO: 42;
(d) a human light chain variable region CDR1 comprising SEQ ID NO: 51;
(e) a human light chain variable region CDR2 comprising SEQ ID NO: 60; and
(f) a human light chain variable region CDR3 comprising SEQ ID NO: 69.

In another preferred embodiment, the antibody comprises:
(a) a human heavy chain variable region CDR1 comprising SEQ ID NO: 25;
(b) a human heavy chain variable region CDR2 comprising SEQ ID NO: 34;
(c) a human heavy chain variable region CDR3 comprising SEQ ID NO: 43;
(d) a human light chain variable region CDR1 comprising SEQ ID NO: 52;
(e) a human light chain variable region CDR2 comprising SEQ ID NO: 61; and
(f) a human light chain variable region CDR3 comprising SEQ ID NO: 70.

In another preferred embodiment, the antibody comprises:
(a) a human heavy chain variable region CDR1 comprising SEQ ID NO: 26;
(b) a human heavy chain variable region CDR2 comprising SEQ ID NO: 35;
(c) a human heavy chain variable region CDR3 comprising SEQ ID NO: 44;
(d) a human light chain variable region CDR1 comprising SEQ ID NO: 53;
(e) a human light chain variable region CDR2 comprising SEQ ID NO: 62; and
(f) a human light chain variable region CDR3 comprising SEQ ID NO: 71.

In another preferred embodiment, the antibody comprises:
(a) a human heavy chain variable region CDR1 comprising SEQ ID NO: 27;
(b) a human heavy chain variable region CDR2 comprising SEQ ID NO: 36;
(c) a human heavy chain variable region CDR3 comprising SEQ ID NO: 45;
(d) a human light chain variable region CDR1 comprising SEQ ID NO: 54;
(e) a human light chain variable region CDR2 comprising SEQ ID NO: 63; and
(f) a human light chain variable region CDR3 comprising SEQ ID NO: 72.

Antibodies Having Particular Germline Sequences

In certain embodiments, a defucosylated antibody of the invention comprises a heavy chain variable region from a particular germline heavy chain immunoglobulin gene and/or a light chain variable region from a particular germline light chain immunoglobulin gene.

For example, in a preferred embodiment, the invention provides a defucosylated monoclonal antibody, or an antigen-binding portion thereof, comprising a heavy chain variable region that is the product of or derived from a human $V_H$ 5-51 gene, wherein the antibody specifically binds to human PSMA. In another preferred embodiment, the invention provides a defucosylated monoclonal antibody, or an antigen-binding portion thereof, comprising a heavy chain variable region that is the product of or derived from a human $V_H$ 3-30.3 gene, wherein the antibody specifically binds PSMA. In another preferred embodiment, the invention provides a defucosylated monoclonal antibody, or an antigen-binding portion thereof, comprising a light chain variable region that is the product of or derived from a human $V_k$ L6 gene, wherein the antibody specifically binds to human PSMA. In another preferred embodiment, the invention provides a defucosylated monoclonal antibody, or an antigen-binding portion thereof, comprising a light chain variable region that is the product of or derived from a human $V_k$ 04/014 gene, wherein the antibody specifically binds to human PSMA. In another preferred embodiment, the invention provides a defucosylated monoclonal antibody, or an antigen-binding portion thereof, comprising a light chain variable region that is the product of or derived from a human $V_k$ L18 gene, wherein the antibody specifically binds to human PSMA.

In yet another preferred embodiment, the invention provides a defucosylated monoclonal antibody, or an antigen-binding portion thereof, wherein the antibody:
(a) comprises a heavy chain variable region that is the product of or derived from a human $V_H$ 5-51 or 3-30.3 gene (which encodes the amino acid sequence set forth in SEQ ID NOs: 73 and 76, respectively);

(b) comprises a light chain variable region that is the product of or derived from a human $V_k$ L6, 04/014, or L18 gene (which encode the amino acid sequences set forth in SEQ ID NOs: 74, 75 and 77, respectively); and (c) specifically binds to human PSMA.

A preferred $V_H$ and $V_k$ germline combination is $V_H$ 5-51 and $V_k$ L6. Examples of antibodies having $V_H$ and $V_K$ of $V_H$ 5-51 and $V_k$ L6, respectively, are the 4A3, 7F12, 8C12 and 2C6 antibodies. Another preferred $V_H$ and $V_k$ germline combination is $V_H$ 5-51 and $V_k$ 04/014. Examples of antibodies having $V_H$ and $V_k$ of $V_H$ 5-51 and Vk 04/014, respectively, are the 8A11 and 16F9 antibodies. Another preferred $V_H$ and $V_k$ germline combination is $V_H$ 5-51 and $V_k$ L18. Examples of antibodies having $V_H$ and $V_k$ of $V_H$ 5-51 and $V_k$ L18, respectively, are the 2A10 and 2F5 antibodies. Another preferred $V_H$ and $V_k$ germline combination is $V_H$ 3-30.3 and $V_k$ L18. An example of an antibody having $V_H$ and $V_k$ of $V_H$ 3-30.3 and $V_k$ L18, respectively, is the 1C3 antibody.

As used herein, a human antibody comprises heavy or light chain variable regions that is "the product of" or "derived from" a particular germline sequence if the variable regions of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins (eg., using the Vbase database) and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally-occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

Homologous Antibodies

In yet another embodiment, a defucosylated antibody of the invention comprises heavy and light chain variable regions comprising amino acid sequences that are homologous to the amino acid sequences of the preferred antibodies described herein, and wherein the antibodies retain the desired functional properties of the anti-PSMA antibodies of the invention.

For example, the invention provides a defucosylated monoclonal antibody, or antigen binding portion thereof, comprising a heavy chain variable region and a light chain variable region, wherein:

(a) the heavy chain variable region comprises an amino acid sequence that is at least 80% homologous to an amino acid sequence selected from the group consisting of SEQ ID NOs: 1-9;

(b) the light chain variable region comprises an amino acid sequence that is at least 80% homologous to an amino acid sequence selected from the group consisting of SEQ ID NOs: 10-18; and (c) the antibody specifically binds to human PSMA.

In other embodiments, the $V_H$ and/or $V_L$ amino acid sequences may be 85%, 90%, 95%, 96%, 97%, 98% or 99% homologous to the sequences set forth above. An antibody having $V_H$ and $V_L$ regions having high (i.e., 80% or greater) homology to the $V_H$ and $V_L$ regions of the sequences set forth above, can be obtained by mutagenesis (e.g., site-directed or PCR-mediated mutagenesis) of one or more nucleic acid molecules encoding SEQ ID NOs: 1-18, followed by testing of the encoded altered antibody for retained function (i.e., binding to PSMA) using the binding assays described herein. Nucleic acid molecules encoding SEQ ID NOs: 6-9 and 15-18 can be found in SEQ ID NOs: 78-85. Nucleic acid molecules encoding SEQ ID NOs: 1-5 and 10-14 can be found in PCT Publication WO 03/064606, FIGS. 17A and 17B.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at www.gcg.com), using a NWSgapdna. CMP matrix and a gap weight of 40, 50, 60, 70, or 80 and a length weight of 1, 2, 3, 4, 5, or 6. The percent identity between two nucleotide or amino acid sequences can also determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

The percent identity between two amino acid sequences can be determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present invention can further be used as a "query sequence" to perform a search against public databases to, for example, identify related sequences. Such searches can be performed using the XBLAST™ program (version 2.0) of Altschul, et al. (1990) *J. Mol. Biol.* 215:403-10. BLAST™ protein searches can be performed with the XBLAST™ program, score=50, wordlength=3 to obtain amino acid sequences homologous to the antibody molecules of the invention. To obtain gapped alignments for comparison purposes, Gapped BLAST™ can be utilized as described in Altschul et al., (1997) *Nucleic Acids Res.* 25(17):3389-3402. When utilizing BLAST™ and Gapped BLAST™ programs, the default parameters of the respective programs (e.g., XBLAST™ and NBLAST™) can be used. See www.ncbi.nlm.nih.gov.

Antibodies with Conservative Modifications

In certain embodiments, a defucosylated antibody of the invention comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the preferred antibodies described herein (e.g., 4A3, 7F12, 8C12, 8A11, 16F9, 2A10, 2C6, 2F5 or 1C3), or conservative modifications thereof, and wherein the antibodies retain the desired functional properties of the anti-PSMA antibodies of the invention. Accordingly, the invention provides a defucosylated monoclonal antibody, or antigen binding portion thereof, comprising a heavy chain variable region comprising CDR1, CDR2, and CDR3 sequences and a light chain variable region comprising CDR1, CDR2, and CDR3 sequences, wherein:

(a) the heavy chain variable region CDR3 sequence comprises the amino acid sequence of SEQ ID NO: 37-45, and conservative modifications thereof;

(b) the light chain variable region CDR3 sequence comprises the amino acid sequence of SEQ ID NO: 64-72, and conservative modifications thereof; and (c) the antibody specifically binds to human PSMA.

In a preferred embodiment, the heavy chain variable region CDR2 sequence comprises the amino acid sequence of SEQ ID NO: 28-36, and conservative modifications thereof; and the light chain variable region CDR2 sequence comprises the amino acid sequence of SEQ ID NO: 55-63, and conservative modifications thereof. In another preferred embodiment, the heavy chain variable region CDR1 sequence comprises the amino acid sequence of SEQ ID NO: 19-27, and conservative modifications thereof; and the light chain variable region CDR1 sequence comprises the amino acid sequence of SEQ ID NO: 46-54, and conservative modifications thereof.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function (i.e., the functions set forth in (i) through (iv) above) using the functional assays described herein.

Alternatively, in another embodiment, mutations can be introduced randomly along all or part of a anti-PSMA antibody coding sequence, such as by saturation mutagenesis, and the resulting modified anti-PSMA antibodies can be screened for binding activity.

Antibodies that Bind to the Same Epitope as Anti-PSMA Antibodies of the Invention In another embodiment, the invention provides defucosylated antibodies that bind to the same epitope as do the various anti-PSMA antibodies of the invention provided herein, such as other human antibodies that bind to the same epitope as the 4A3, 7F12, 8C12, 8A11, 16F9, 2A10, 2C6, 2F5 or 1C3 antibodies described herein. Such additional antibodies can be identified based on their ability to cross-compete (e.g., to competitively inhibit the binding of, in a statistically significant manner) with other antibodies of the invention, such as 4A3, 7F12, 8C12, 8A11, 16F9, 2A10, 2C6, 2F5 or 1C3, in standard PSMA binding assays. The ability of a test antibody to inhibit the binding of, e.g., 4A3, 7F12, 8C12, 8A11, 16F9, 2A10, 2C6, 2F5 or 1C3, to human PSMA demonstrates that the test antibody can compete with that antibody for binding to human PSMA; such an antibody may, according to non-limiting theory, bind to the same or a related (e.g., a structurally similar or spatially proximal) epitope on human PSMA as the antibody with which it competes. In a preferred embodiment, the defucosylated antibody that binds to the same epitope on human PSMA as 4A3, 7F12, 8C12, 8A11, 16F9, 2A10, 2C6, 2F5 or 1C3 is a human monoclonal antibody. Such human monoclonal antibodies can be prepared and isolated as described in PCT Publications WO 01/09192 and WO 03/064606.

Engineered and Modified Antibodies

A defucosylated antibody of the invention further can be prepared using an antibody having one or more of the $V_H$ and/or $V_L$ sequences disclosed herein as starting material to engineer a modified antibody, which modified antibody may have altered properties from the starting antibody. An antibody can be engineered by modifying one or more amino acid residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) *Nature* 332:323-327; Jones, P. et al. (1986) *Nature* 321:522-525; Queen, C. et al. (1989) *Proc. Natl. Acad. See. U.S.A.* 86:10029-10033; U.S. Pat. No. 5,225,539 to Winter, and U.S. Pat. Nos. 5,530,101; 5,585,089; 5,693,762 and 6,180,370 to Queen et al.).

Accordingly, another embodiment of the invention pertains to a defucosylated monoclonal antibody, or antigen binding portion thereof, comprising a heavy chain variable region comprising CDR1, CDR2, and CDR3 sequences comprising an amino acid sequence selected from the group consisting of SEQ ID NOs: 19-27, SEQ ID NOs: 28-36, and SEQ ID NOs: 37-45, respectively, and a light chain variable region comprising an amino acid sequence selected from the group consisting of SEQ ID NOs: 46-54, SEQ ID NOs: 55-63 and SEQ ID NOs: 64-72, respectively. Thus, such antibodies contain the $V_H$ and $V_L$ CDR sequences of monoclonal antibodies 4A3, 7F12, 8C12, 8A11, 16F9, 2A10, 2C6, 2F5 or 1C3, yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat, E. A., et al. (1991) *Sequences of Proteins of Immunological Interest*, Fifth Edition, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" *J. Mol. Biol.* 227:776-798; and Cox, J. P. L. et al. (1994) "A Directory of Human Germ-line $V_H$ Segments Reveals a Strong Bias in their Usage" *Eur. J. Immunol.* 24:827-836; the contents of each of which are expressly incorporated herein by reference.

Preferred framework sequences for use in the antibodies of the invention are those that are structurally similar to the framework sequences used by selected antibodies of the invention, e.g., similar to the $V_H$ 5-51 or 3-30.3 sequences (SEQ ID NOs: 73 and 76, respectively) and/or the $V_k$ L6, 04/014 or L18 framework sequence (SEQ ID NOs: 74, 75 and 77, respectively) used by preferred monoclonal antibodies of the invention. The $V_H$ CDR1, 2 and 3 sequences, and the $V_K$ CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Another type of variable region modification is to mutate amino acid residues within the $V_H$ and/or $V_K$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Preferably conservative modifications (as discussed above) are introduced. The mutations may be amino acid substitutions, additions or deletions, but are preferably substitutions. Moreover, typically no more than one, two, three, four or five residues within a CDR region are altered.

Accordingly, in another embodiment, the invention provides defucosylated anti-PSMA monoclonal antibodies, or antigen binding portions thereof, comprising a heavy chain variable region comprising: (a) a $V_H$ CDR1 region comprising an amino acid sequence selected from the group consisting of SEQ ID NO: 19-27, or an amino acid sequence having one, two, three, four or five amino acid substitutions, deletions or additions as compared to an amino acid sequence selected from the group consisting of SEQ ID NO: 19-27; (b) a $V_H$ CDR2 region comprising an amino acid sequence selected from the group consisting of SEQ ID NO: 28-36, or an amino acid sequence having one, two, three, four or five amino acid substitutions, deletions or additions as compared to an amino acid sequence selected from the group consisting of SEQ ID NO: 28-36; (c) a $V_H$ CDR3 region comprising an amino acid sequence selected from the group consisting of SEQ ID NO: 37-45, or an amino acid sequence having one, two, three, four or five amino acid substitutions, deletions or additions as compared to an amino acid sequence selected from the group consisting of SEQ ID NO: 37-45; (d) a $V_K$ CDR1 region comprising an amino acid sequence selected from the group consisting of SEQ ID NO: 46-54, or an amino acid sequence having one, two, three, four or five amino acid substitutions, deletions or additions as compared to an amino acid sequence selected from the group consisting of SEQ ID NO: 46-54; (e) a $V_K$ CDR2 region comprising an amino acid sequence selected from the group consisting of SEQ ID NO: 55-63, or an amino acid sequence having one, two, three, four or five amino acid substitutions, deletions or additions as compared to an amino acid sequence selected from the group consisting of SEQ ID NO: 55-63; and (f) a $V_K$ CDR3 region comprising an amino acid sequence selected from the group consisting of SEQ ID NO: 64-72, or an amino acid sequence having one, two, three, four or five amino acid substitutions, deletions or additions as compared to an amino acid sequence selected from the group consisting of SEQ ID NO: 64-72.

Engineered antibodies of the invention include those in which modifications have been made to framework residues within $V_H$ and/or $V_K$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. For example, for 8C12 and 8A11, amino acid residue #13 (within FR1) of $V_H$ is a threonine whereas this residue in the corresponding $V_H$ 5-51 germline sequence is a lysine. To return the framework region sequences to their germline configuration, the somatic mutations can be "backmutated" to the germline sequence by, for example, site-directed mutagenesis or PCR-mediated mutagenesis (e.g., residue 13 of FR1 of the $V_H$ of 8C12 or 8A11 can be "backmutated" from threonine to lysine. Such "backmutated" antibodies are also intended to be encompassed by the invention.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication WO 94/29351 by Bodmer et al.

In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta. Moreover, the binding sites on human IgG1 for FcγR1, FcγRII, FcγRIII and FcRn have been mapped and variants with improved binding have been described (see Shields, R. L. et al. (2001) *J. Biol. Chem.* 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A.

Another modification of the antibodies herein that is contemplated by the invention is pegylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP 0 154 316 by Nishimura et al. and EP 0 401 384 by Ishikawa et al.

Methods of Engineering Antibodies

As discussed above, the defucosylated anti-PSMA antibodies having $V_H$ and $V_K$ sequences disclosed herein can be used to create new anti-PSMA antibodies by modifying the VH and/or $V_K$ sequences, or the constant region(s) attached thereto. Thus, in another aspect of the invention, the structural features of an anti-PSMA antibody of the invention, e.g. 4A3, 7F12, 8C12, 8A11, 16F9, 2A10, 2C6, 2F5 or 1C3, are used to create structurally related defucosylated anti-PSMA antibodies that retain at least one functional property of the antibodies of the invention, such as binding to human PSMA. For example, one or more CDR regions of 4A3, 7F12, 8C12, 8A11, 16F9, 2A10, 2C6, 2F5 or 1C3, or mutations thereof, can be combined recombinantly with known framework regions and/or other CDRs to create additional, recombinantly-engineered, anti-PSMA antibodies of the invention, as discussed above. Other types of modifications include those described in the previous section. The starting material for the engineering method is one or more of the $V_H$ and/or $V_K$ sequences provided herein, or one or more CDR regions thereof. To create the engineered antibody, it is not necessary to actually prepare (i.e., express as a protein) an antibody having one or more of the $V_H$ and/or $V_K$ sequences provided herein, or one or more CDR regions thereof. Rather, the information contained in the sequence(s) is used as the starting material to create a "second generation" sequence(s)

derived from the original sequence(s) and then the "second generation" sequence(s) is prepared and expressed as a protein.

Accordingly, in another embodiment, the invention provides a method for preparing an anti-PSMA antibody comprising:

(a) providing: (i) a heavy chain variable region antibody sequence comprising a CDR1 sequence selected from the group consisting of SEQ ID NOs: 19-27, a CDR2 sequence selected from the group consisting of SEQ ID NOs: 28-36 and/or a CDR3 sequence selected from the group consisting of SEQ ID NOs: 37-45; and/or (ii) a light chain variable region antibody sequence comprising a CDR1 sequence selected from the group consisting of SEQ ID NOs: 46-54, a CDR2 sequence selected from the group consisting of SEQ ID NOs: 55-63 and/or a CDR3 sequence selected from the group consisting of SEQ ID NOs: 64-72;

(b) altering at least one amino acid residue within the heavy chain variable region antibody sequence and/or the light chain variable region antibody sequence to create at least one altered antibody sequence; and (c) expressing the altered antibody sequence as a protein.

Standard molecular biology techniques can be used to prepare and express the altered antibody sequence. The altered antibody sequence so prepared can then be made in defucosylated form using the methods disclosed herein to obtain a defucosylated altered anti-PSMA antibody.

The functional properties of the altered antibodies can be assessed using standard assays available in the art and/or described herein, such as those set forth in the Examples (e.g., flow cytometry, binding assays, ADCC assays).

In certain embodiments of the methods of engineering antibodies of the invention, mutations can be introduced randomly or selectively along all or part of an anti-PSMA antibody coding sequence and the resulting modified anti-PSMA antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Nucleic Acid Molecules Encoding Antibodies of the Invention

Another aspect of the invention pertains to nucleic acid molecules that encode the antibodies of the invention. The term "nucleic acid molecule", as used herein, is intended to include DNA molecules and RNA molecules. A nucleic acid molecule may be single-stranded or double-stranded, but preferably is double-stranded DNA. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. (1987) *Current Protocols in Molecular Biology*, Greene Publishing and Wiley Interscience, New York. A nucleic acid of the invention can be, for example, DNA or RNA and may or may not contain intronic sequences. In a preferred embodiment, the nucleic acid is a cDNA molecule.

Nucleic acids of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Preferred nucleic acids molecules of the invention are those encoding the VH and VL sequences of the 4A3, 7F12, 8C12, 8A11, 16F9, 2A10, 2C6, 2F5 and 1C3 monoclonal antibodies. The DNA sequences encoding the VH and VL amino acid sequences of 4A3, 7F12, 8C12, 8A11, 16F9 are published in PCT Publication No. WO 03/064606 (see FIGS. 17A and 17B), the contents of which is expressly incorporated by reference. The DNA sequence encoding the VH sequence of 1C3 is shown in SEQ ID NO: 78. The DNA sequence encoding the VL sequence of 1C3 is shown in SEQ ID NO: 82. The DNA sequence encoding the VH sequence of 2A10 is shown in SEQ ID NO: 79. The DNA sequence encoding the VL sequence of 2A10 is shown in SEQ ID NO: 83. The DNA sequence encoding the VH sequence of 2C6 is shown in SEQ ID NO: 80. The DNA sequence encoding the VL sequence of 2C6 is shown in SEQ ID NO: 84. The DNA sequence encoding the VH sequence of 2F5 is shown in SEQ ID NO: 81. The DNA sequence encoding the VL sequence of 2C6 is shown in SEQ ID NO: 85.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al. (1991) *Sequences of Proteins of Immunological Interest*, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) *Sequences of Proteins of Immunological Interest*, Fifth Edition, U.S. Department of Health and Human Services, NIH Publication No. 91-3242) and DNA fragments encompassing these regions can be obtained by standard PCR amplification. The light chain constant region can be a kappa or lambda constant region, but most preferably is a kappa constant region.

To create a scFv gene, the VH- and VL-encoding DNA fragments are operatively linked to another fragment encoding a flexible linker, e.g., encoding the amino acid sequence (Gly$_4$-Ser)$_3$ (SEQ ID NO: 89), such that the VH and VL sequences can be expressed as a contiguous single-chain protein, with the VL and VH regions joined by the flexible linker (see e.g., Bird et al. (1988) Science 242:423-426; Huston et al. (1988) Proc. Natl. Acad. Sci. USA 85:5879-5883; McCafferty et al., (1990) Nature 348:552-554).

The nucleic acid compositions of the present invention, while often in a native sequence (except for modified restriction sites and the like), from either cDNA, genomic or mixtures may be mutated, thereof in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

Production of Monoclonal Antibodies of the Invention

Monoclonal antibodies (mAbs) of the present invention can be produced by a variety of techniques, including conventional monoclonal antibody methodology e.g., the standard somatic cell hybridization technique of Kohler and Milstein (1975) Nature 256: 495. Although somatic cell hybridization procedures are preferred, in principle, other techniques for producing monoclonal antibody can be employed e.g., viral or oncogenic transformation of B lymphocytes.

The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

In various embodiments, the antibody can be, for example, human antibodies, humanized antibodies or chimeric antibodies.

Chimeric or humanized antibodies of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.). A variety of mouse anti-PSMA antibodies are known in the art that can be used to create chimeric or humanized anti-PSMA antibodies, for example, 3F5.4G6, 3D7.1.1, 4E10-1.14, 3E11, 4D8, 3E6, 3C9, 2C7, 1G3, 3C4, 3C6, 4D4, 1G9, 5C8B9, 3G6, 4C8B9, E99, J415, J533 and J591. In a preferred embodiment, the antibodies of the invention are human monoclonal antibodies. Such human monoclonal antibodies directed against PSMA can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb Mouse® (Medarex, Inc.) contains human immunoglobulin gene miniloci that encode unrearranged human heavy (μ and γ) and κ light chain immunoglobulin sequences, together with targeted mutations that inactivate the endogenous μ and κ chain loci (see e.g., Lonberg, et al. (1994) Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg, N. et al. (1994), supra; reviewed in Lonberg, N. (1994) Handbook of Experimental Pharmacology 113:49-101; Lonberg, N. and Huszar, D. (1995) Intern. Rev. Immunol. 13: 65-93, and Harding, F. and Lonberg, N. (1995) Ann. N.Y. Acad. Sci. 764:536-546). The preparation and use of HuMab® mice, and the genomic modifications carried by such mice, is further described in Taylor, L. et al. (1992) Nucleic Acids Research 20:6287-6295; Chen, J. et al. (1993) International Immunology 5: 647-656; Tuaillon et al. (1993) Proc. Natl. Acad. Sci. USA 90:3720-3724; Choi et al. (1993) Nature Genetics 4:117-123; Chen, J. et al. (1993) EMBO J. 12: 821-830; Tuaillon et al. (1994) J. Immunol. 152:2912-2920; Taylor, L. et al. (1994) International Immunology 6: 579-591; and Fishwild, D. et al. (1996) Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In another embodiment, human antibodies of the invention can be raised using a mouse that carries human immunoglobulin sequences on transgenes and transchomosomes, such as a mouse that carries a human heavy chain transgene and a human light chain transchromosome. Such mice, referred to herein as "KM mice", are described in detail in PCT Publication WO 02/43478 to Ishida et al.

Still further, alternative transgenic animal systems expressing human immunoglobulin genes are available in the art and can be used to raise anti-PSMA antibodies of the invention. For example, an alternative transgenic system referred to as the Xenomouse™ (Abgenix, Inc.) can be used; such mice are described in, for example, U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise anti-PSMA antibodies of the invention. For example, mice carrying both a human heavy chain transchromosome and a human light chain tranchromosome, referred to as "TC mice" can be used; such mice are described in Tomizuka et al. (2000) Proc. Natl. Acad. Sci. USA 97:722-727. Furthermore, cows carrying human heavy and light chain transchromosomes have been described in the art (Kuroiwa et al. (2002) Nature Biotechnology 20:889-894) and can be used to raise anti-PSMA antibodies of the invention.

Human monoclonal antibodies of the invention can also be prepared using phage display methods for screening libraries of human immunoglobulin genes. Such phage display methods for isolating human antibodies are established in the art.

See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Immunization of Human Ig Mice

When human Ig mice are used to raise human antibodies of the invention, such mice can be immunized with a cell line that expresses PSMA (such as LnCaP cells, ATCC® CRL-1740™), with a purified or enriched preparation of PSMA antigen (such as LnCaP cell membranes) and/or with recombinant PSMA, or a recombinant PSMA fusion protein, as generally described by Lonberg, N. et al. (1994) *Nature* 368 (6474): 856-859; Fishwild, D. et al. (1996) *Nature Biotechnology* 14: 845-851; and PCT Publication WO 98/24884 and WO 01/14424. Preferably, the mice will be 6-16 weeks of age upon the first infusion. For example, a membrane preparation of LnCaP cells can be used to immunize the human Ig mice intraperitoneally.

Detailed procedures to generate fully human monoclonal antibodies to PSMA are described in PCT Publications WO 01/09192 and WO 03/064606. Cumulative experience with various antigens has shown that the transgenic mice respond when initially immunized intraperitoneally (IP) with antigen in complete Freund's adjuvant, followed by every other week IP immunizations (up to a total of 6) with antigen in incomplete Freund's adjuvant. However, adjuvants other than Freund's are also found to be effective. In addition, whole cells in the absence of adjuvant are found to be highly immunogenic. The immune response can be monitored over the course of the immunization protocol with plasma samples being obtained by retroorbital bleeds. The plasma can be screened by ELISA (as described below), and mice with sufficient titers of anti-PSMA human immunoglobulin can be used for fusions. Mice can be boosted intravenously with antigen 3 days before sacrifice and removal of the spleen. It is expected that 2-3 fusions for each immunization may need to be performed. Between 6 and 24 mice are typically immunized for each antigen. Usually both HCo7 and HCo12 strains are used. In addition, both HCo7 and HCo12 transgene can be bred together into a single mouse having two different human heavy chain transgenes (HCo7/HCo12).

Generation of Hybridomas Producing Human Monoclonal Antibodies of the Invention

To generate hybridomas producing human monoclonal antibodies of the invention, splenocytes and/or lymph node cells from immunized transgenic mice carrying human immunoglobulin genes can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3X63-Ag8.653 nonsecreting mouse myeloma cells (ATCC® CRL 1580™) with 50% PEG. Cells are plated at approximately $2 \times 10^5$ in flat bottom microtiter plate, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma®; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-sepharose™ (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

Generation of Transfectomas Producing Monoclonal Antibodies of the Invention

Antibodies of the invention also can be produced in a host cell transfectoma using, for example, a combination of well known recombinant DNA techniques and gene transfection methods (e.g., Morrison, S. (1985) *Science* 229:1202).

For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_K$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe, Y. et al. (1988) *Mol. Cell. Biol.* 8:466-472).

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12-13).

Preferred host cells for expressing the recombinant antibodies of the invention include cells which modify the fucosylation of an expressed antibody. For example, the host cell may be a cell that is lacking in a fucosyltransferase enzyme such that the host cell produces proteins lacking fucose in their carbohydrates, or a host cell that expresses glycoprotein-modifying glycosyl transferases such that expressed antibodies in the host cell have increased bisecting GlcNac structures that prevents fucosylation. Other mammalian host cells for expressing the recombinant antibodies include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NS0 myeloma cells, COS cells and SP2 cells. In particular, for use with NS0 myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Immunoconjugates

In another aspect, the present invention features a defucosylated anti-PSMA antibody, or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other preferred examples of therapeutic cytotoxins that can be conjugated to an antibody of the invention include duocarmycins, calicheamicins, maytansines and auristatins, and derivatives thereof. An example of a calicheamicin antibody conjugate is commercially available (Mylotarg™; Wyeth-Ayerst).

Cytoxins can be conjugated to antibodies of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito, G. et al. (2003) *Adv. Drug Deliv. Rev.* 55:199-215; Trail, P. A. et al. (2003) *Cancer Immunol. Immunother.* 52:328-337; Payne, G. (2003) *Cancer Cell* 3:207-212; Allen, T. M. (2002) *Nat. Rev. Cancer* 2:750-763; Pastan, I. and Kreitman, R. J. (2002) *Curr. Opin. Investig. Drugs* 3:1089-1091; Senter, P. D. and Springer, C. J. (2001) *Adv. Drug Deliv. Rev.* 53:247-264.

Antibodies of the present invention also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine[131], indium[111], yttrium[90] and lutetium[177]. Method for preparing radioimmunconjugates are established in the art. Examples of radioimmunoconjugates are commercially available, including Zevalin™ (IDEC Pharmaceuticals) and Bexxar™ (Corixa Pharmaceuticals), and similar methods can be used to prepare radioimmunoconjugates using the antibodies of the invention.

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in *Monoclonal Antibodies And Cancer Therapy*, Reisfeld et al. (eds.), pp. 243-56 (Alan R. Liss, Inc. 1985); Hellstrom et al., "Antibodies For Drug Delivery", in *Controlled Drug Delivery* (2nd Ed.), Robinson et al. (eds.), pp. 623-53 (Marcel Dekker, Inc. 1987); Thorpe, "Antibody Carriers Of Cytotoxic Agents In Cancer Therapy: A Review", in *Monoclonal Antibodies '84: Biological And Clinical Applications*, Pinchera et al. (eds.), pp. 475-506 (1985); "Analysis, Results, And Future Prospective Of The Therapeutic Use Of Radiolabeled Antibody In Cancer Therapy", in *Monoclonal Antibodies For Cancer Detection And Therapy*, Baldwin et al. (eds.), pp. 303-16 (Academic Press 1985), and Thorpe et al., "The Preparation And Cytotoxic Properties Of Antibody-Toxin Conjugates", *Immunol. Rev.,* 62:119-58 (1982).

Pharmaceutical Compositions

In another aspect, the present invention provides a composition, e.g., a pharmaceutical composition, containing one or a combination of monoclonal antibodies, or antigen-binding portion(s) thereof, of the present invention, formulated together with a pharmaceutically acceptable carrier. Such compositions may include one or a combination of (e.g., two or more different) antibodies, or immunoconjugates of the invention. For example, a pharmaceutical composition of the invention can comprise a combination of antibodies (or immunoconjugates) that bind to different epitopes on the target antigen or that have complementary activities.

Pharmaceutical compositions of the invention also can be administered in combination therapy, i.e., combined with other agents. For example, the combination therapy can include a defucosylated anti-PSMA antibody of the present invention combined with at least one other anti-neoplastic, anti-inflammatory or immunosuppressive agent. Such therapeutic agents include, among others, steroidal and nonsteroidal anti-inflammatory drugs (NSAIDS), e.g., aspirin and other salicylates, such as ibuprofen (Motrin™, Advil™), naproxen (Naprosyn™), sulindac (Clinoril™), diclofenac (Voltaren™), piroxicam (Feldene™), ketoprofen (Orudis™), diflunisal (Dolobid™), nabumetone (Relafen™), etodolac (Lodine™), oxaprozin (Daypro™), indomethacin (Indocin™), and aspirin in high doses. Other examples of therapeutic agents that can be used in combination therapy are described in greater detail below in the section on uses of the antibodies of the invention.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody or immunoconjuage, may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for a defucosylated anti-PSMA antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three monthgs or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml.

Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-PSMA antibody of the invention preferably results in a decrease in severity of disease symptoms, an increase in frequency and duration of disease symptom-free periods, or a prevention of impairment or disability due to the disease affliction. For example, for the treatment of cancerous tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

A composition of the present invention can be administered via one or more routes of administration using one or more of a variety of methods known in the art. As will be appreciated by the skilled artisan, the route and/or mode of administration will vary depending upon the desired results. Preferred routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, a defucosylated antibody of the invention can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the defucosylated antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V.V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); p 120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273.

Uses and Methods of the Invention

The defucosylated antibodies, antibody compositions and methods of the present invention have numerous in vitro and in vivo diagnostic and therapeutic utilities involving the diagnosis and treatment of disorders involving expression of PSMA. For example, these molecules can be administered to cells in culture, e.g. in vitro or ex vivo, or to human subjects, e.g., in vivo, to treat, prevent and to diagnose a variety of disorders. As used herein, the term "subject" is intended to include human and non-human animals. Non-human animals includes all vertebrates, e.g., mammals and non-mammals, such as non-human primates, sheep, dogs, cats, cows, horses, pigs, chickens, avians, amphibians, and reptiles. Preferred subjects include human patients having disorders associated with PSMA expression. When antibodies to PSMA are administered together with another agent, the two can be administered in either order or simultaneously.

Suitable routes of administering the antibody compositions (e.g., antibody or immunoconjugate) of the invention in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

In one embodiment, the antibodies of the invention can be initially tested for binding activity associated with therapeutic or diagnostic use in vitro. For example, compositions of the invention can be tested using ELISA and flow cytometric assays. Moreover, the activity of these molecules in triggering at least one effector-mediated effector cell activity, including inhibiting the growth of and/or killing of cells expressing PSMA can be assayed. Protocols for assaying for effector cell-mediated ADCC are described in the Examples below.

A. Detection Methods

In one embodiment, the antibodies of the invention can be used to detect levels of PSMA, or levels of cells which contain PSMA on their membrane surface, which levels can then be linked to certain disease symptoms.

In a particular embodiment, the invention provides methods for detecting the presence of PSMA in a sample, or measuring the amount of PSMA on the surface of cells, comprising contacting the sample, and a control sample, with a defucosylated antibody, or an antigen binding portion thereof, which specifically binds to PSMA, under conditions that allow for formation of a complex between the antibody or portion thereof and PSMA. The formation of a complex is then detected, wherein a difference complex formation between the sample compared to the control sample is indicative the presence of PSMA in the sample. For example, standard detection methods, well-known in the art, such as ELISA and flow cytometic assays, can be performed using the compositions of the invention.

Accordingly, in one aspect, the invention further provides methods for detecting the presence of PSMA (e.g., human PSMA) in a sample, or measuring the amount of PSMA, comprising contacting the sample, and a control sample, with an antibody of the invention, or an antigen binding portion thereof, which specifically binds to PSMA, under conditions that allow for formation of a complex between the antibody or portion thereof and PSMA. The formation of a complex is then detected, wherein a difference in complex formation between the sample compared to the control sample is indicative of the presence of PSMA in the sample.

The compositions of the invention can also be used to target cells expressing PSMA, for example for labeling such cells. For such use, the binding agent can be linked to a molecule that can be detected. Thus, the invention provides methods for localizing ex vivo or in vitro cells expressing PSMA. The detectable label can be, e.g., a radioisotope, a fluorescent compound, an enzyme, or an enzyme co-factor.

B. Inhibition of Growth of PSMA+ Cells

The antibodies can be used to inhibit growth of cells expressing PSMA which, in turn, can be linked to the prevention or amelioration of certain disease symptoms associated with PSMA expression. Differences in PSMA expression during a disease state as compared to a non-disease state can be determined by contacting a test sample from a subject suffering from the disease and a control sample with the anti-PSMA antibody under conditions that allow for the formation of a complex between the antibody and PSMA. Any complexes formed between the antibody and PSMA are detected and compared in the sample and the control.

For example, the antibodies can be used to elicit in vivo or in vitro one or more of the following biological activities: to inhibit the growth of and/or kill a cell expressing PSMA; to mediate phagocytosis or ADCC of a cell expressing PSMA in the presence of human effector cells; to inhibit shedding of soluble PSMA. As discussed herein, the defucosylated antibodies of the invention exhibit enhanced ADCC activity as compared to the fucosylated form of the antibody.

Accordingly, in another aspect, the invention provides a method of inhibiting growth of PSMA$^+$ cells comprising contacting said cells with a defucosylated anti-PSMA antibody under conditions sufficient to induce antibody-dependent cellular cytotoxicity (ADCC) of said cells. The cells can be, for example, tumor cells. In a preferred embodiment, the anti-PSMA antibody is a human antibody.

In one embodiment, the antibodies, or binding portions thereof, of the present invention can be used to modulate PSMA levels on target cells, such as by capping and eliminating receptors on the cell surface. Mixtures of anti-Fc receptor antibodies can also be used for this purpose.

Target-specific effector cells, e.g., effector cells linked to compositions of the invention can also be used as therapeutic agents. Effector cells for targeting can be human leukocytes such as macrophages, neutrophils or monocytes. Other cells include eosinophils, natural killer cells and other IgG- or IgA-receptor bearing cells. If desired, effector cells can be obtained from the subject to be treated. The target-specific effector cells, can be administered as a suspension of cells in a physiologically acceptable solution. The number of cells administered can be in the order of $10^8$-$10^9$ but will vary depending on the therapeutic purpose. In general, the amount will be sufficient to obtain localization at the target cell, e.g., a tumor cell expressing PSMA, and to effect cell killing by, e.g., phagocytosis. Routes of administration can also vary.

Therapy with target-specific effector cells can be performed in conjunction with other techniques for removal of targeted cells. For example, anti-tumor therapy using the compositions of the invention and/or effector cells armed with these compositions can be used in conjunction with chemotherapy. Additionally, combination immunotherapy may be used to direct two distinct cytotoxic effector populations toward tumor cell rejection.

C. Use of Immunoconjugates and Combination Therapy

In one embodiment, immunoconjugates of the invention can be used to target compounds (e.g., therapeutic agents, labels, cytotoxins, radiotoxins immunosuppressants, etc.) to cells which have PSMA cell surface molecules by linking such compounds to the antibody. Thus, the invention also provides methods for localizing ex vivo or in vitro cells expressing PSMA (e.g., with a detectable label, such as a radioisotope, a fluorescent compound, an enzyme, or an enzyme co-factor). Alternatively, the immunoconjugates can be used to kill cells which have PSMA cell surface receptors by targeting cytotoxins or radiotoxins to PSMA, such as to PSMA-expressing tumor cells to thereby eliminate the tumor cell.

In other embodiments, the subject can be additionally treated with an agent that modulates, e.g., enhances or inhibits, the expression or activity of Fcγ or Fcγ receptors by, for example, treating the subject with a cytokine. Preferred cytokines for administration during treatment include of granulocyte colony-stimulating factor (G-CSF), granulocyte-macrophage colony-stimulating factor (GM-CSF), interferon-γ (IFN-γ), and tumor necrosis factor (TNF).

In another embodiment, patients treated with antibody compositions of the invention can be additionally administered (prior to, simultaneously with, or following administration of an antibody of the invention) with another therapeutic agent, such as a cytotoxic or radiotoxic agent, which enhances or augments the therapeutic effect of the human antibodies. The antibody can be linked to the agent (as an immunocomplex) or can be administered separate from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, and cyclophosphamide hydroxyurea which, by themselves, are only effective at levels which are toxic or subtoxic to a patient. Cisplatin is intravenously administered as a 100 mg/ml dose once every four weeks and adriamycin is intravenously administered as a 60-75 mg/ml dose once every 21 days. Co-administration of the anti-PSMA antibodies, or antigen binding fragments thereof, of the present invention with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

D. Treatment of Cancer

PSMA has been shown to be expressed on tumor cells, such as prostate carcinoma tumor cells, and also has been shown to be expressed on vascular endothelial cells proximate to cancerous cells, such as urothelial cancerous cells, colon cancerous cells, rectal cancerous cells, lung cancerous cells, breast cancerous cells and metastatic adenocarcinoma cancerous cells of the liver (see U.S. Pat. No. 6,136,311). Accordingly, the antibodies of the invention can be used to treat cancer by inhibiting growth of PSMA-expressing tumor cells or by inhibiting growth of vascular endothelial cells proximate to tumor cells. Thus, in another embodiment, the present invention provides a method of inhibiting growth of a tumor in a subject, wherein cells of the tumor or vascular endothelial cells proximate to the tumor are PSMA$^+$, in which a defucosylated anti-PSMA antibody of the invention is administered to the subject such that growth of the tumor is inhibited. For human subjects, the antibody preferably is a humanized or human antibody. In a preferred embodiment, the tumor cells are prostate tumor cells. In other embodiments, the tumor cells are from cancers such as colon, renal, rectal, urothelial, breast, bladder, liver, pancreas or melanoma.

The treatment methods of the invention involve administering to a subject an antibody composition of the present invention in an amount effective to treat or prevent the disorder. The antibody composition can be administered alone or along with another therapeutic agent, such as a cytotoxic or a radiotoxic agent (conjugated to or administered with the antibody) which acts in conjunction with or synergistically with the antibody composition to treat or prevent the disease associated with PSMA expression.

Kits

Also within the scope of the invention are kits comprising an antibody of the invention and instructions for use. The kit can further contain one or more additional reagents, such as an immunostimulatory reagent, a cytotoxic agent or a radiotoxic agent, or one or more additional antibodies of the invention (e.g., an antibody having a complementary activity which binds to an epitope in the PSMA antigen distinct from the first antibody). Kits typically include a label indicating the intended use of the contents of the kit. The term label includes any writing, or recorded material supplied on or with the kit, or which otherwise accompanies the kit.

The present invention is further illustrated by the following examples which should not be construed as further limiting. The contents of all figures and all references, patents and published patent applications cited throughout this application are expressly incorporated herein by reference.

Example 1

Expression of Anti-PSMA Monoclonal Antibody in Eggs of Chimeric Chickens

In this example, the expression of the anti-PSMA human monoclonal antibody, 7F12, in the eggs of chimeric chickens is described. General methodologies for expressing proteins, including antibodies, in the eggs of chimeric chickens is described in PCT Publication WO 2004/015123, the contents of which are expressly incorporated herein by reference. Additional information regarding expression of antibodies in eggs of chimeric chickens is described in U.S. application Ser. No. 11/062,325, entitled "Tissue Specific Expression of Antibodies in Chickens", filed Feb. 18, 2005, the contents of which are expressly incorporated herein by reference.

In the following example, a transgene containing an endogenous egg white regulatory sequence comprising a promoter together with exogenous immunoglobulin light and heavy chain genes is constructed to yield tissue specific antibody expression in the tubular gland cells of the oviduct. The antibody molecules so expressed are then deposited in the egg white of a transgenic chicken. In this embodiment, antibodies encoded by any rearranged immunoglobulin gene are expressed specifically in tissue comprising the tubular gland cells of the magnum region of the oviduct and can be isolated from the whites of eggs. The rearranged immunoglobulin genes encoding the monoclonal antibody are preferentially expressed in the oviduct to the substantial exclusion of expression in other tissues, although expression in other tissues may exist above detectable levels.

Preferred transgene constructs for ovalbumin derived monoclonal antibody constructs are shown in FIG. 12. These transgene constructs, designated Ov7.5 and Ov15, have approximately 7.5 kb and 15 kb, respectively, of the ovalbumin promoter flanking the MAb coding region at the 5' end sequence and 15 kb of the promoter sequence 3' of the coding region. The coding regions comprise the variable regions for both the light chain and heavy chain, J-C intron sequences, the kappa light chain constant region, an IRES sequence and the gamma 1 isotype heavy chain constant regions. The 3' end of the construct comprises a GFP gene and a selectable marker, in this case a puromycin resistance gene driven by the CX promoter. The lengths of the ovalbumin promoter sequence both 3' and 5' of the monoclonal antibody coding region are examples only and analogous constructs may include 25-100 kb or more of the 5' sequence as well as varying lengths in the 3' sequence. Those of ordinary skill in the art will appreciate that the GFP marker is present only for detection in physiological specimens and can be removed without departing from the utility of the transgene. The puromycin resistance marker can be substituted with any marker that provides the ability to select embryonic stem cells that are successfully transformed with the transgene. Several types of analogous selectable marker are well known in the art and can be used essentially interchangeably with the puromycin resistance gene of this embodiment.

The transgene used for expression of the human anti-PSMA mAb 7F12 was referred to as Ov15 mAb7F12 and included 15 kb of the 5' regulatory sequences of the ovalbumin promoter. Additionally, the signal peptide was directly joined to VL to prevent its removal during mRNA processing. Newly derived female cES cell lines (prepared as described in PCT Publication WO 2004/015123) were used so that high grade chimeras could produce eggs. The Ov15MAb7F12 vector was transfected into a female cES cell line and stably transfected clones were screened by PCR. One clone (OVH) was further analyzed by Southern blot. It showed that only one copy of the Ov15MAb7F12 transgene was integrated into the cES genome and the transgene contained at least 10 kb of the 5' Ov promoter sequences.

Chimeric chickens were made from the OVH clone for transgene analysis. Ten chimeric chicks were used for early estrogen induction. Donor cES-derived areas (GFP-positive) from various tissues including the magnum portion of the oviduct, muscle, brain, liver and gut, were collected. RT-PCR with primers specific for L and H chains were used to monitor expression of the transgene. L and H chain transcripts were detected in the magnum but not in muscle, brain and liver samples from 3 out of 4 induced female chicks (OV15-34, OV15-76 and OV15-83). However, low-level expression was also detected in ileum, cecum and colon. Immunohistochemistry of sections from estrogen-induced magnums confirmed the expression of the monoclonal antibody in GFP-positive tubular gland cells but not in GFP-positive epithelial cells. Taken together, these data demonstrate that the Ov15MAb7F12 vector directed transgene expression in the tubular gland cells of the oviduct. The low-level ectopic expression detected in the gut suggests that 15 Kb of the 5' regulatory sequences of Ov may not be sufficient to confer positional independent, tissue-specific expression of the transgene.

Sixty-nine chimeras were generated from OVH cES cells carrying the Ov15MAb7F12 to evaluate the deposition of the fully human MAb into eggs. Thirty chimeric hens were raised to sexual maturity and commenced laying. Eggs from all of the hens contained MAb in their egg white as indicated by ELISA analysis. The concentration and amount of MAb in eggs varied among the chimeric hens, presumably due to the varying degree of chimerism in the magnum. Eight chimeric hens laid eggs that contained more than 1 mg of MAb per egg and the maximal level among the 30 chimeras was 3.4 mg of MAb per egg. Four chimeric hens laid eggs whose mean level of MAb was between 1.2 and 1.6 mg per egg. Six chimeric hens laid eggs whose mean level of MAb was between 0.5 and 1.0 mg per egg.

The presence of MAb in egg white was further analyzed by western blot with a rabbit anti-human IgG (H+L) that recognizes both the H and L chains. Egg white from a wild type, non-chimeric White Leghorn hen was used as the negative control. Purified human IgG1, κ (Sigma™) was used as the reference standard. Full-length L and H chains were detected in egg white samples from five chimeric hens (OV15-17, OV15-29, Ov15-71, OV16-34 and OV16-42). Fully assembled $H_2L_2$ was also seen, although small amounts of assembly intermediates were also present.

To determine the variation of the MAb concentration deposited in egg white, eggs from 5 different chimeric hens (OV16-34, OV16-42, OV17-29, OV17-52 and OV17-83) were monitored over a period of 3-4 months. In 3 hens, the amount of MAb peaked during the first few weeks, then dropped approximately two fold and remained stable over the next few months. In two hens, the expression level remained relatively stable over the time course. If not all of the tubular glands secrete and deposit ovalbumin protein as the egg is passing through the magnum portion of the oviduct, the amount of MAb deposited in the egg white could vary as each egg passes through the magnum due to the chimeric nature of the tubular glands in these hens.

Blood samples from 26 chimeric hens and a Barred Plymouth Rock (BPR) hen (negative control) were analyzed by ELISA for the presence of human IgG. Eighteen hens had detectable levels of MAb in blood with the highest concentration of 39 ng/ml observed in hen OV17-83. The correlation coefficient (r) between the level of MAb in blood and the concentration of MAb in egg white was 0.67. However, this comparison was complicated by the fact that the extent of chimerism in different tissues can vary significantly. For example, hen OV17-122 had very little MAb in egg (0.02 mg/egg on average) but had the second highest concentration of MAb in blood (36 ng/ml). We speculate that the presence of MAb in blood may not be a consequence of leakage from oviduct expression but instead reflects ectopic expression (for example, the gut where ectopic expression was detected by RT-PCR in estrogen-induced chimeras).

Example 2

Purification and Protein Characterization of Antibody Product

MAb 7F12 was purified from egg white as follows. Egg white was first mixed at a low shear rate for 30 min at room temperature and then ovomucin precipitated by a method known in the art. One volume of homogenized egg white suspension was added to three volumes of reverse osmosis water and stirred for 30 min. The diluted suspension was adjusted to pH 6.0 using 0.5 M phosphoric acid and then centrifuged for 20 min at 12,100 g. Approximately 3% of the egg white protein containing mostly ovomucin was removed by this method. The supernatant was adjusted to pH 7.4 using 0.5 M dibasic sodium phosphate and 150 mM sodium chloride concentration with crystalline salt. The human IgG was purified on a Protein A-Sepharose™ FF column (Amersham Biosciences) at a 120 cm/h linear flow rate. The adsorbed human IgG was washed with five column volumes of the loading buffer (PBS, pH 7.4) and then eluted by using 3 mM phosphoric acid. The eluted human IgG fraction was adjusted to pH 7.5 using 60 mM sodium phosphate (pH 7.5) containing 230 mM NaCl to achieve a final concentration of 40 mM sodium phosphate and 150 mM NaCl. The sample was then filtered through a 0.2 μm syringe filter (Pall).

Most of the purified material was a fully assembled MAb molecule with a purity greater than 90% (determined by ELISA and A280). The MAb7F12 produced in chicken was compared in several assays with MAb7F12 produced in conventional CHO cell culture, as follows:

1. SEC-HPLC Analysis of Antibody

About 10 μg of IgG sample was analyzed on a Waters 2795 HPLC using a 4.6×300 mm BioSep™ SEC 53000 column (Phenomenex). Chromatography was carried out in 0.1 M sodium phosphate, 0.15 M NaCl, and 0.1 M sodium sulfate, pH 7.2 at 0.4 ml/min flow rate for 20 min. Separations were monitored at $A_{280}$. Molecular weight standards (Bio-Rad) were used to determine approximate molecular weight. SEC-HPLC analysis showed that both were more than 90% IgG monomer.

2. Nano LC ESI MS/MS Sequence Analysis of Protein

Both MAb preparations (chicken egg-expressed and CHO cell-expressed) were reduced and alkylated, dialyzed overnight and digested with trypsin for 4 hours at 37° C. in 25 mM ammonium bicarbonate (PH 8). Tandem mass spectrometry of both tryptic digests was performed on a Nano HPLC system (Dionex, Sunnyvale, Calif.) interfaced to a QSTAR™ pulsar mass spectrometer (MDS Sciex, Concord, Ontario, Canada) operation in positive ion mode and using collision induced dissociation (CID) to obtain tandem spectra. A 1 μl aliquot of each sample was injected and separated using a 75 μm diameter Pepmap C18 column at a flow rate of 250 nl/min. The mobile phase was solvent A (95% water, 5% acetonitrile, 0.5% formic acid) and solvent B (20% water, 80% acetonitrile, 0.5% formic acid). The instrument was operated in information dependent acquisition mode with 7 s operating cycles, recording a full spectrum for 2 s then selecting the most intense ion to record a CID spectrum during the next 5 s. Spectra were analyzed using Mascot™ (Matrix Science, London, UK). Analysis of both MAb preparations by the described methods showed no sequence difference depending on the expression system.

3. LC-MS Analysis

IgG samples (50 µg) in 4 M guanidine HCl were reduced in 25 mM DTT by incubating the samples at 60° C. for 90 min. Samples were then alkylated in 45 mM iodoacetic acid for 15 min at room temperature in the dark and the reaction was stopped with 22 mM DTT. Prior to LC-MS samples were dialyzed against 1 L of 25 mM ammonium bicarbonate and 50 µl of each sample was injected to a Poros™ R1/10 2.1×100 mm column (Applied Biosystems® ) using a Waters 2795 HPLC equipped with a Micromass ZQ™ mass spectrometer and analyzed in positive ion mode. The mobile phase was (A) 0.1% formic acid and 0.01% trifluoroacetic acid (TFA) and (B) 100% $CH_3CN$ with 0.1% formic acid and 0.01% TFA. Elution (0.25 ml/min) was conducted by a linear gradient of 10-60% of (B) in (A) developed over 100 min.

Analysis of the L chain showed that both MAb preparations had identical mass (+/−3 Da.).

4. cIEF Analysis

IgG samples (50 µg each at 1.0 mg/ml) were dialyzed against water to remove salts before CE analysis. Capillary electrophoresis isoelectric focusing was performed on a P/ACE™ MDQ CE system (Beckman) with normal polarity, using a 50 µm internal diameter eCAP neutral capillary (Beckman) with 30 cm effective length. Sample was injected for 60 s by pressure injection at 20 psi. Separation was carried out using 15 kV for 45 min. The temperature of the capillary was 20° C. The anolyte was 20 mM phosphoric acid and the catholyte was 40 mM sodium hydroxide. The rinse solution was 10 mM phosphoric acid and the cathodic mobilizer solution was used as provided (Beckman). The separations were monitored at $A_{280}$. The cIEF analysis indicated that both have similar isoelectric points (pI) although CHO derived MAb7F12 had an increased charge heterogeneity.

5. Thermal Stability by Differential Scanning Calorimetry

The thermal stabilities 7F12 produced in the chicken and CHO expression systems were obtained using differential scanning calorimetry (DSC) and compared with their corresponding forms that were deglycosylated in their Fc domain. Calorimetric measurements of melting temperatures ($T_m$) were carried out on a VP-Capillary DSC differential scanning microcalorimeter platform that is combined with an autosampler (MicroCal LLC, Northampton, Mass., USA). Sample cell volume is 0.144 mL. Denaturation data on the glycosylated and deglycosylated forms of the antibodies was obtained by heating the samples, at a concentration of 2.3 µM, from 30 to 95° C. at a rate of 1° C./min. The protein samples were present in phosphate-buffered saline (PBS) at pH 7.4. The same buffer was used in the reference cell to obtain the molar heat capacity by comparison. The observed thermograms were baseline corrected and normalized data was analyzed using Origin v7.0.

The unfolding profiles of the CHO and chicken derived antibodies were quite different, whereas the unfolding profiles of the Fc-deglycosylated antibodies were almost identical. The DSC data indicated that the differences in the thermal stabilities of the CHO and chicken derived Mabs is primarily due to the different glycosylation patterns present in their respective $C_H2$ domains. Of the several melting transition points, the first one is critical as it determines the overall stability of the antibodies at lower temperature. The $T_{m1}$ of the chicken derived antibody was determined to be 63.8° C., whereas the $T_{m1}$ of the CHO expressed antibody was determined to be 62.7° C. Given that the $T_{m1}$ of the chicken derived antibody is higher than the $T_{m1}$ of the CHO expressed antibody, it is likely that the chicken derived antibody is more thermo-stable at room temperature.

Example 3

Oligosaccharide Analysis of Chicken-Expressed Anti-PSMA Antibody

In this example, the glycosylation pattern of the chicken egg-expressed 7F12 antibody was analyzed using a variety of different techniques.

1. Oligosaccharide Characterization by CE-LIF

Oligosaccharides were released from IgG samples (100 µg) by overnight incubation of the samples with 12.5 mU PNGaseF (Prozyme™ ) at 40° C. Under the conditions used, the N-linked glycans from the Fc portion of HuMAbF1 expressed in CHO cells and chicken were released. Following ethanol precipitation to remove MAb protein, the supernatant containing the glycans was dried by vacuum centrifugation and resuspended in 19 mM APTS (Beckman) in 15% acetic acid and 1 M sodium cyanoborohydride in THF (Sigma® ). The glycan labeling reaction was allowed to continue overnight at 40° C. followed by 25-fold dilution of sample in water. APTS-labeled glycans were applied to capillary electrophoresis with laser induced fluorescence on a P/ACE™ MDQ CE system (Beckman) with reverse polarity, using a 50 µm internal diameter N—CHO coated capillary (Beckman) with 50 cm effective length. Samples were pressure (8 sec.) injected and separation was carried out at 20° C. using Carbohydrate Separation Gel Buffer (Beckman) at 25 kV for 20 min. The separations were monitored using a laser-induced fluorescence detection system (Beckman) with a 3 mW argon ion laser and excitation wavelength of 488 nm and emission of 520 nm. The oligosaccharide profile of 7F12 produced in the chicken was found to be quite different from that of 7F12 produced in the CHO cells.

2. Oligosaccharide Characterization by MALDI Q-TOF MS

Purified antibodies (100 µg each at 1.0 mg/ml) were treated with 4 µl of PNGaseF, an endoglycosidase that cleaves N-linked carbohydrates (Prozyme™ ). The samples were incubated at 37° C. overnight followed by dialysis overnight against 50 mM ammonium bicarbonate (pH 8). The protein was removed by ethanol precipitation. The released carbohydrates were desalted on a micro carbon column from Glygen Corp. (Columbia, Md.) essentially following the vendor's protocol, but the elution volume was reduced to 5 µl. A 1 µl aliquot of each glycan sample was mixed 1:1 (v:v) with matrix solution (α-cyano-4-hydroxycinnamic acid or 2,5-dihydroxybenzoic acid (Applied Biosystems® ), spotted on a MALDI target plate and allowed to air-dry. MALDI-Q-TOF tandem analysis was used to perform the analysis of intact glycoconjugates. All mass spectra were recorded on a QSTAR™ pulsar i mass spectrometer equipped with an o-MALDI source 2 (MDS Sciex, Concord, Ontario, Canada), which provides the mass (composition) of classes of carbohydrates. After the glycan profiling of both the MAbs, the possible glycosidic linkage in each glycan was investigated. High CID mass spectra were recorded on a 4700 Proteomics analyzer with a TOF/TOf™ optics (Applied Biosystems® , Forster City, Calif.). For high CID MSMS experiments, the collision energy was set at 1 kV. Inside the collision cell, the selected oligosaccharide ions were collided with argon at a pressure of $2 \times 10^{-6}$ Torr.

The carbohydrate composition and possible glycosidic linkages of eleven major glycans in chicken-derived 7F12 analyzed by MALDI TOF mass spectrometry are summarized in FIGS. 13A and 13B. The oligosaccharide structures were found to contain high-mannose type, complex type and hybrid type N-glycans. None of the structures contained fucosyl residues.

3. Monosaccharide Analysis by HPLC with HPAE-DAD

IgG samples (200 μg) were subjected to acid hydrolysis using either 2 N TFA (for estimating neutral sugars) or 6 N HCl (for estimating amino sugars) at 100° C. for 4 h. Samples were dried by vacuum centrifugation at ambient temperature and were reconstituted in 200 μl water prior to analysis by HPAE-PAD (Dionex™). Monosaccharides were separated using a CarboPac PA10 4×250 mm column with pre-column Amino Trap™ and Borate Trap™ (Dionex™). Procedures were followed according to Dionex™ Technical Note 53. Monosaccharide peak identity and relative abundance were determined using monosaccharide standards (Dionex™).

Monosaccharide analysis of chicken and CHO produced 7F12 is summarized in Table 1 below.

TABLE 1

Monosaccharide Analysis of chicken and CHO produced MAb 7F12

| Monosaccharide | CHO MAb pmol (% total) | Chicken MAb pmol (% total) |
| --- | --- | --- |
| Fucose | 692 (18) | 0 |
| Glucosamine | 1,536 (40) | 1,571 (52) |
| Galactose | 671 (17) | 43 (1) |
| Mannose | 940 (25) | 1,513 (47) |
| Total | 3,839 (100) | 3,127 (100) |

The monosaccharide analysis revealed a difference in carbohydrate composition and showed the presence of N-acetyl glusosamine residues, mannose residues, and very low content of galactose residues in 7F12 produced in chicken. No fucose residues were detected in the chicken produced 7F12, in contrast to the CHO expressed antibody preparation that contained fucosyl residues.

Exoglycosidase analysis of glycans by CE and mass spectrometry to identify the terminal sugar residues confirmed the absence of terminal sialic acid and fucose residues in MAb7F12 produced in chicken tubular gland cells.

In summary, the most striking differences in the N-linked oligosaccharide profiles were the presence of high mannose type N-glycans, the absence of fucose and the very low content of galactose residues in the antibody produced in the chicken.

Example 4

Functional Analysis of Chicken-Expressed Anti-PSMA Antibody

In this example, the functional properties of the chicken egg-expressed 7F12 anti-PSMA antibody were examined, including binding affinity, internalization, serum half life in vivo and antibody dependent cellular cytotoxicity (ADCC) activity.

1. Binding Affinity for PSMA

PSMA on LNCaP cells (ATCC® CRL-1740™) was used as antigen to assay for antibody binding by flow cytometry. Cells were grown in RPMI 1640 medium supplemented with 10% FBS, 10 mM HEPES, 2 mM L-glutamine, and 1 mM sodium pyruvate. The antigen binding property of 7F12 produced in chicken tubular gland cells was compared with that of 7F12 produced in CHO cells. 200,000 cells/well were incubated in duplicate for 30 minutes with 50 μl aliquots of antibody at various concentrations. Cells were washed twice before addition of goat anti-human IgG PE labeled antibody (Jackson ImmunoResearch) at 1:200 dilution, 50 μl /well for 30 minutes at 4° C. Cells were washed twice in PBS with 1% BSA and assayed by FACS. $EC_{50}$ values of MAb binding to PSMA on LNCaP cells were determined from binding curves utilizing GraphPad Prism 3.0™(GraphPad Software).

Both antibody preparations produced nearly identical binding curves to PSMA expressed on LNCaP cells with similar $EC_{50}$ values. The data demonstrated that while the chicken-derived and CHO-derived antibodies are glycosylated differently, they recognize and bind antigen equivalently.

2. Antibody Internalization

Binding of the 7F12 mAb to PSMA leads to internalization of the antibody. In one potential application, MAb could be conjugated with cytotoxins in order to target and destroy PSMA-expressing tumor cells. Internalization of antibody binding to PSMA on LNCaP cells was determined by incubating cells with MAb and Hum-Zap™ (Advanced Targeting Systems). HumZap™ is a goat anti-human IgG antibody conjugated to the ribosome inactivating protein, saporin. Cells are killed when the 7F12 MAb/Hum-Zap™ complex binds to PSMA on the cell surface and is internalized whereas antibody or Hum-Zap™ alone is not toxic to LNCaP cells. LNCaP cells (10,000/well) were incubated in triplicate, for 48 hours, at 37° C., in 150 μl of culture medium containing 300 ng Hum-Zap™, and 300 ng of 7F12 MAb, or control MAb. Cell proliferation and survival was determined with the CellTiter-Glo® Luminescent Cell Viability Assay (Promega). Internalization assays were also done by incubating dilutions of antibody in cell culture medium with 10,000 adherent LNCaP cells/well, for 2 hours at 4° C. Antibody solutions were gently removed and replaced with 150 μl of medium containing 200 ng of HumZap™. Cell viability was determined following 48 hours of incubation at 37° C. $EC_{50}$ values for antibody internalization were determined graphically with Prism 3.0™(GraphPad Software).

Both the chicken-expressed and the CHO-expressed antibody preparations internalized with a similar efficiency. When tested over a range of antibody concentrations, the $EC_{50}$ values for internalization of both the chicken-derived and CHO-derived 7F12 MAb were 0.49 nM.

3. In Vivo Half Life

The in vivo half-life of the chicken produced 7F12 MAb was analyzed in parallel with the CHO produced antibody in BALB/c mice by intravenous injection of radiolabeled antibodies. Ten μg of MAb protein were lightly iodinated (less than one I per antibody) with $^{125}I$ using the Iodobead method (Pierce). Six week-old female BALB/c mice (Taconic Farms, Germantown, N.Y.) were fed 0.1 mg/ml potassium iodide in their drinking water for one week prior to the experiment. Four mice per protein were injected intravenously into the tail vein with approximately 600,000 cpm of labeled MAb and whole body radioactivity was measured at selected times using a whole body gamma counter (Wm. B. Johnson NaI crystal detector with a Ludlum scaler). Half-life was calculated by exponential regression analysis of the residual radioactivity.

The 7F12 MAb produced by chicken tubular gland cells cleared with a half-life ($t_{1/2}$) of 102.4±0.9 hours, while 7F12 MAb produced by CHO cells cleared more slowly with a half-life of 207.5±18.3 hours.

4. ADCC Activity

LNCaP-C42B cells were tested in a modified $^{51}Cr$ ADCC assay. Human peripheral blood mononuclear cells were purified from heparinized whole blood by standard Ficoll-paque separation. The cells were resuspended (at 1×10$^6$ cells/ml) in RPMI1640 media containing 10% FBS and 10 U/ml of human IL-2 and incubated overnight at 37° C. The following day, the cells were collected and washed once in culture media and resuspended at 2×10$^7$ cells/ml. Two million target LNCaP-C42b cells are incubated with 200 µCi $^{51}$Cr in 1 ml total volume for 1 hour at 37° C. The target cells are washed once, resuspended in 1 ml of media, and incubated at 37° C. for an additional 30 minutes. After the final incubation, the target cells were washed once and brought to a final volume of 1×10$^5$ cells/ml. For the final ADCC assay, 100 µl of labeled LNCaP cells were incubated with 50 µl of effector cells and 50 µl of antibody. The final target to effector ratio of 1:100 was selected. In all studies, human IgG1 isotype control was run and compared to CHO-derived anti-PSMA 7F12 antibody. Other controls which were included were: a) target and effector cells but no antibody, b) target cells with no effector cells and c) target and effector cells in the presence of 3% Triton X-100. Following 4 hour incubation at 37° C., the supernatants were collected and counted on a gamma Counter (Cobra II auto-gamma from Packard Instruments) with a reading window of 240-400 keV. The counts per minute were plotted as a function of antibody concentration and the data was analyzed by non-linear regression, sigmoidal dose response (variable slope) using Prism™ software (San Diego, Calif.). The percent lysis was determined by the following equation:

%Lysis=(Sample *CPM*–No antibody *CPM*)/Triton*X CPM*–No antibody *CPM*)×100

We have found that it is important that both EC$_{50}$ values and % Lysis are monitored in all studies. For example, it is possible when comparing two antibodies to have a change in either the EC$_{50}$ or % lysis or both.

Figure 14A:
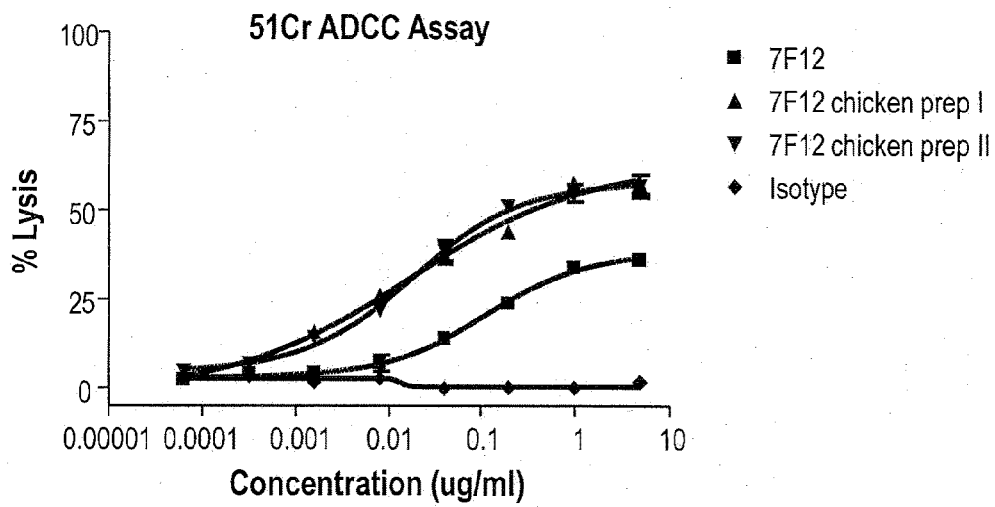
FIGS. 14A-14B are graphs showing the results of ADCC assays with CHO cell-expressed 7F12 ("7F12") and chicken-expressed 7F12, as compared to an isotype control The results are expressed as % lysis.
Figure 14B:
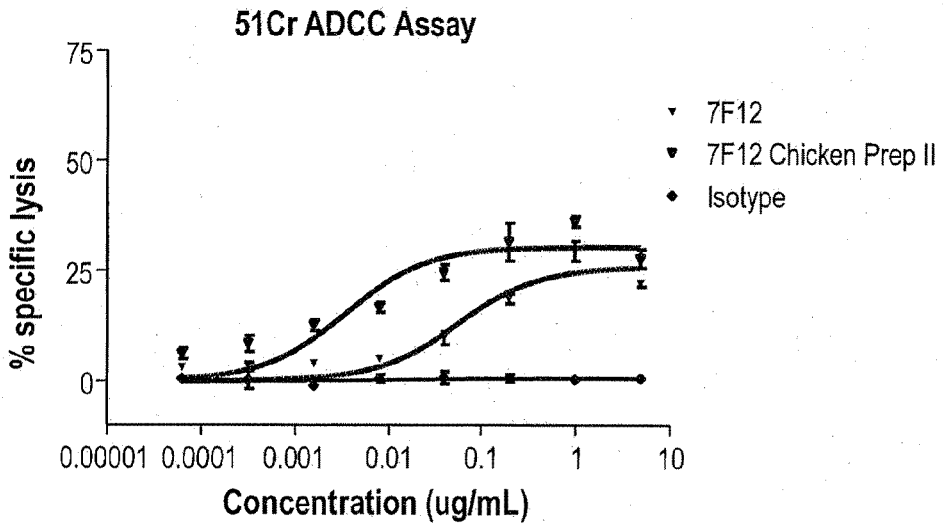

The results of two different ADCC experiments are shown in FIG. 14A (IL-2 stimulated effector cells) and in FIG. 14B (fresh human peripheral blood effector cells). FIG. 14A shows that CHO derived MAb induces dose dependent cell lysis which reaches a plateau at 38% lysis with an EC$_{50}$ of 0.11 µg/ml with IL-2 stimulated effector cells. In contrast, the chicken egg derived MAb was more potent and more efficatious. The maximum % lysis of the chicken egg derived MAb was 60% with two different preparations of the antibody. The enhanced potency over the CHO derived MAb was also demonstrated as the EC$_{50}$ of this material was 0.018 µg/ml. That is, the EC$_{50}$ for the chicken-expressed antibody was approximately six-fold lower than the EC$_{50}$ for the CHO-expressed antibody. Finally, as expected, isotype control antibody did not induce cell lysis. ADCC with unstimulated effector cells (fresh PBMCs) showed a greater difference in EC$_{50}$ values, but lower overall cell killing (FIG. 14B).

Figure 15:
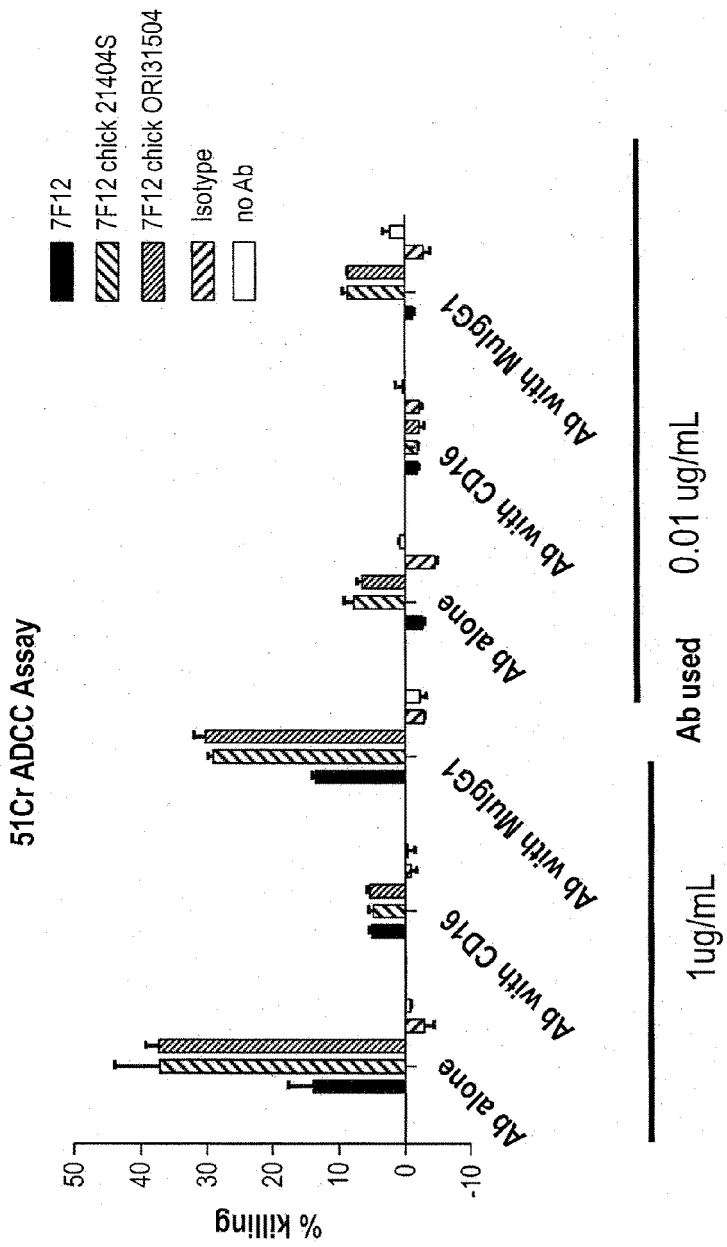
FIG. 15 is a bar graph showing the results of experiments in which ADCC activity of CHO cell-expressed 7F12 ("7F12") and chicken-expressed 7F12, as compared to an isotype control, was blocked by anti-CD16 antibody.

CD16 (FcγRIII) is a key receptor that mediates ADCC. The specificity of the ADCC response was shown by blocking the interaction of target and effector cells using a monoclonal antibody directed against CD16. Blockade of ADCC with anti-CD16 antibodies was conducted according to the ADCC assay described above, with the following modifications. The cells were incubated with either 1 µg/ml (a saturating dose) or 0.01 µg/ml (a sub-optimal dose) of 7F12 anti-PSMA antibodies (chicken or CHO expressed) in the absence or presence of 5 µg/ml of anti-CD16 antibody 3G8 or isotype control antibody. The results are shown in FIG. 15. One µg/ml of anti-PSMA antibody, in the absence of anti-CD16 antibody, induced approximately 15% and 38% lysis with CHO-derived and chicken-derived antibody, respectively. This % lysis was reduced to ~4% in the presence of anti-CD16 antibody while isotype control antibody had no effect.

Example 5

Preparation and Characterization of Defucosylated Anti-PSMA Antibody in FUT8 Negative Host Cells In this example, a fully human anti-PSMA monoclonal antibody was expressed in a cell line lacking a fucosyl transferase enzyme such that the cell line produces proteins lacking fucose in their carbohydrates. The defucosylated antibody was tested against a fucosylated anti-PSMA antibody (expressed in a different cell line that contains the fucosyl transferase enzyme) to determine structural and characteristic differences between the antibodies, using a variety of chemical analysis techniques, including capillary electrophoresis, comparison of amino acid sequence, mass differences by mass spectroscopy and charge variation by capillary isoelectric focusing.

The anti-PSMA fully human monoclonal antibody 2A10 was used. The amino acid and nucleotide sequences of the 2A10 heavy chain are shown in FIG. 5A and the amino acid and nucleotide sequences of the 2A10 light chain are shown in FIG. 5B. The 2A10 heavy and light chain variable sequences were subcloned into an expression vector. The 2A10 kappa variable region cDNA, including its signal sequence and an optimal Kozak sequence, was subcloned in frame with the human kappa constant region. The 2A10 heavy chain variable region cDNA, including its signal sequence and an optimal Kozak sequence, was subcloned in frame with the human γ1 heavy constant region. Both light and heavy chain expression were driven by the SR alpha promoter. This expression vector is described in further detail in PCT Application No. PCT/US2004/028954, the contents of which are expressly incorporated herein by reference.

The expression vector was transfected into the FUT8$^{-/-}$ host cell line Ms704 by DNA electroporation. The Ms704 FUT8$^{-/-}$ cell line was created by the targeted disruption of the FUT8 gene in CHO/DG44 cells using two replacement vectors, and is more fully described in U.S. Patent Publication 20040110704 by Yamane et al. and Yamane-Ohnuki et al. (2004) *Biotechnol Bioeng* 87:614-22. The Ms704 cells were adapted to growth in suspension culture in growth medium EX-CELL™ 325 PF CHO Medium (JRH #14335) supplemented with 100 µM hypoxanthine with 16 µM thymidine (Invitrogen™ #11067-030) and 6 mM L-glutamine (Invitrogen™ #25030-081). The vector DNA to be used for electroporation was ethanol precipitated and resuspended in water. 1.5 µg DNA was utilized for each of eight electroporations. The Ms704 cells were prepared for transfection by washing the cells in a sucrose-buffered solution (SBS) and resuspending the cells at 1×10$^7$ cells/ml SBS solution. 400 µl cells were mixed with construct DNA and electroporated utilizing settings at 250 volts, 275 microfaradays capacitance and 25 ohms resistance (BTX® Molecular Delivery Systems #630 electro cell manipulator). The cells were removed from the electroporation cuvettes and 20 ml growth medium was added. The cells were plated into a 96 well dish using 200 µl cells per well, approximately 4×10$^4$ cells/well. 2 days after the electroporation, 150 µl of medium was removed from each well and replaced with 150 µl selection medium, growth medium with 400 µg/ml G418 (Invitrogen #10131-035). Every three to seven days, 150 µl of selection medium per well was replaced with fresh selection medium.

CHO DG44 host cells (FUT 8+/+) were electroporated with the identical 2A10 construct using a similar procedure and CHO DG44 transfectants expressing recombinant 2A10 antibody containing fucosylated carbohydrate were established.

The highest producing Ms704 and CHO DG44 clones were expanded and recombinant 2A10 antibody was purified from cell culture supernatants by Protein A affinity chromatography.

Comparative analysis of N-linked oligosaccharides derived from the Ms704 and the CHO DG44 derived anti-PSMA monoclonal antibody samples was done by capillary electrophoresis laser induced fluorescence (cLIF) (Chen and Evangelista (1998) *Electrophoresis* 15:1892). The N-linked oligosaccharides of the purified antibody were released by adding the peptide N-glycanase (Prozyme™) and incubating overnight. The protein was ethanol precipitated, and the carbohydrate containing supernatant was transferred to a new tube and dried using a Speedvac®. The carbohydrates were resuspended and derivatized with 8-aminopyrene-1,3,6-trisulfonate (APTS) under mild reductive amination conditions in which desialylation and loss of fucose residues was minimized. The reaction adducts were analyzed by capillary electrophoresis with a laser-induced fluorescence detector (Beckman Coulter) (Ma and Nashabeh (1999) *Anal. Chem.* 71:5185). Differences in the oligosaccharide profile were observed between the antibody obtained from the Ms704 cell line as compared to the CHO DG44 cell line, consistent with an absence of fucose residues in the Ms704 derived anti-PSMA antibodies. Monosaccharide analysis using Dionex™ -HPLC anion exchange with pulsed amperometric detection confirmed that the Ms704-expressed antibody lacked expression of any fucose residues. The results are summarized below in Table 2.

TABLE 2

Monosaccharide Analysis of MAb 2A10 from FUT8−/− and FUT8+/+ Cells

| Monosaccharide | FUT8+/+ pmol (% total) | FUT8−/− pmol (% total) |
|---|---|---|
| Fucose | 159 (11) | 0 (0) |
| Glucosamine | 655 (46) | 645 (58) |
| Galactose | 52 (4) | 107 (10) |
| Mannose | 561 (39) | 358 (32) |
| Total | 1,427 (100) | 1,110 (100) |

Aside from the difference in oligosaccharides shown by capillary electrophoresis and monosaccharide analysis, the Ms704 and CHO DG44 derived anti-PSMA antibody protein samples were essentially identical. Analysis of N-terminal protein sequence revealed an identical N-terminal amino acid sequence. Mass spectroscopy of the light chain of the Ms704 and CHO DG44 derived anti-PSMA antibodies yielded masses of 23,552 and 23,548, respectively, which were within the error of the instrument. The two antibodies were also tested using a standard capillary isoelectric focusing kit assay (Beckman Coulter) and showed that the two antibody samples had essentially identical isoelectric points. These studies indicate that the protein component of the antibody samples derived from the Ms704 and the CHO DG44 cells are essentially identical with the exception of the defucosylation of the Ms704 derived antibodies. Carbohydrate analysis indicated that the defucosylated form of the antibody had more terminal galactose residues than the fucosylated form of the antibody.

Example 6

Assessment of ADCC Activity of Defucosylated Anti-PSMA Antibody Expressed in FUT8 Negative Host Cells The cytotoxic activity of Ms7040-derived (defucosylated) 2A10 antibody against LNCaP-C42B cells (obtained commercially from ViroMed Laboratories, Minnetonka, Minn.) was tested in a modified $^{51}$Cr ADCC assay. Human peripheral blood mononuclear cells were purified from heparinized whole blood by standard Ficoll-paque separation. The cells were resuspended (at $1\times10^6$ cells/ml) in RPMI1640 media containing 10% FBS and 10 U/ml of human IL-2 and incubated overnight at 37° C. The following day, the cells were collected and washed once in culture media and resuspended at $2\times10^7$ cells/ml. Two million target LNCaP-C42b cells are incubated with 200 µCi $^{51}$Cr in 1 ml total volume for 1 hour at 37° C. The target cells are washed once, resuspended in 1 ml of media, and incubated at 37° C. for an additional 30 minutes. After the final incubation, the target cells are washed once and brought to a final volume of $1\times10^5$ cells/ml. For the final ADCC assay, 100 µl of labeled LNCaP cells were incubated with 50 µl of effector cells and 50 µl of antibody. The final target to effector ratio of 1:100 was selected. In all studies, human IgG1 isotype control was run and compared to CHO DG44-derived (fucosylated) anti-PSMA 2A10 antibody. Other controls which were included were: a) target and effector cells but no antibody, b) target cells with no effector cells and c) target and effector cells in the presence of 3% Triton X-100. Following 4 hour incubation at 37° C., the supernatants were collected and counted on a gamma Counter (Cobra II auto-gamma from Packard Instruments) with a reading window of 240-400 keV. The counts per minute were plotted as a function of antibody concentration and the data was analyzed by non-linear regression, sigmoidal dose response (variable slope) using Prism™ software (San Diego, Calif.). The percent lysis was determined by the following equation:

%Lysis=(Sample *CPM*−No antibody *CPM*)/TritonX *CPM*−No antibody *CPM*)×100

Figure 16A:
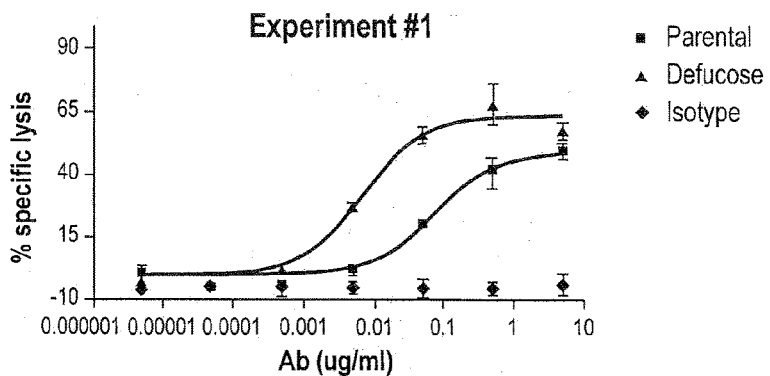
FIGS. 16A-16C are graphs showing the results of ADCC assays with defucosylated 2A10 mAb ("defucose") as compared to fucosylated 2A10 mAb ("parental") and an isotype control.
Figure 16B:
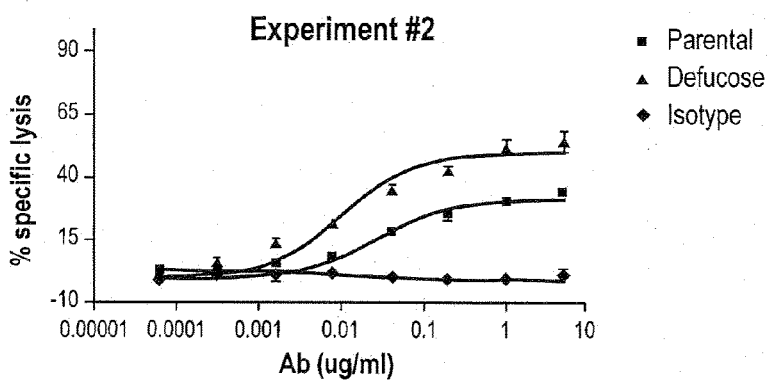

The results of three separate ADCC experiments are shown in FIGS. 16A, 16B (IL-2 stimulated effector cells) and 16C (fresh human peripheral blood effector cells). A cell cytotoxicity curve for the LnCaP cell line using varying concentrations of fuc-2A10 and defuc-2A10 was determined and $EC_{50}$ and % Lysis values were determined. The results from the three experiments corresponding to FIGS. 16A, 16B and 16C, respectively, are shown in Table 3 below:

TABLE 3

Cytotoxic Ability of Defucosylated Anti-PSMA mAb 2A10

| Experiment | $EC_{50}$ (µg/ml) Fucosylated | $EC_{50}$ (µg/ml) Defucosylated | $EC_{50}$ Ratio | % Lysis Fucosylated | % Lysis Defucosylated |
|---|---|---|---|---|---|
| Expt. #1 | 0.08 | 0.007 | 11.4 | 49% | 63% |
| Expt. #2 | 0.026 | 0.009 | 2.9 | 32% | 51% |
| Expt. #3 | 0.036 | 0.002 | 18.0 | n.d. | n.d. |

Figure 16C:
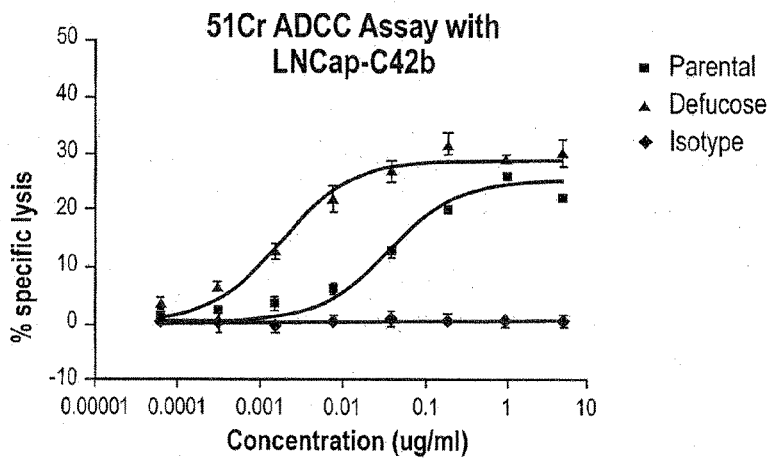

The enhanced potency of the Ms704-derived (i.e., defucosylated) 2A10 mAb, as compared to the CHO DG44-derived (i.e., fucosylated) 2A10b mAb is evident by the lower EC50 values and higher % lysis values for the defucosylated form of the antibody. For example, the EC50 values for the defucosylated form are approximately 3-fold to 18-fold lower for the defucosylated form. ADCC activity with unstimulated effector cells (fresh PBMCs), as compared to IL-2 stimulated effector cells, showed a greater difference in $EC_{50}$ values, but lower overall cell killing (FIG. 16C).

Figure 17:
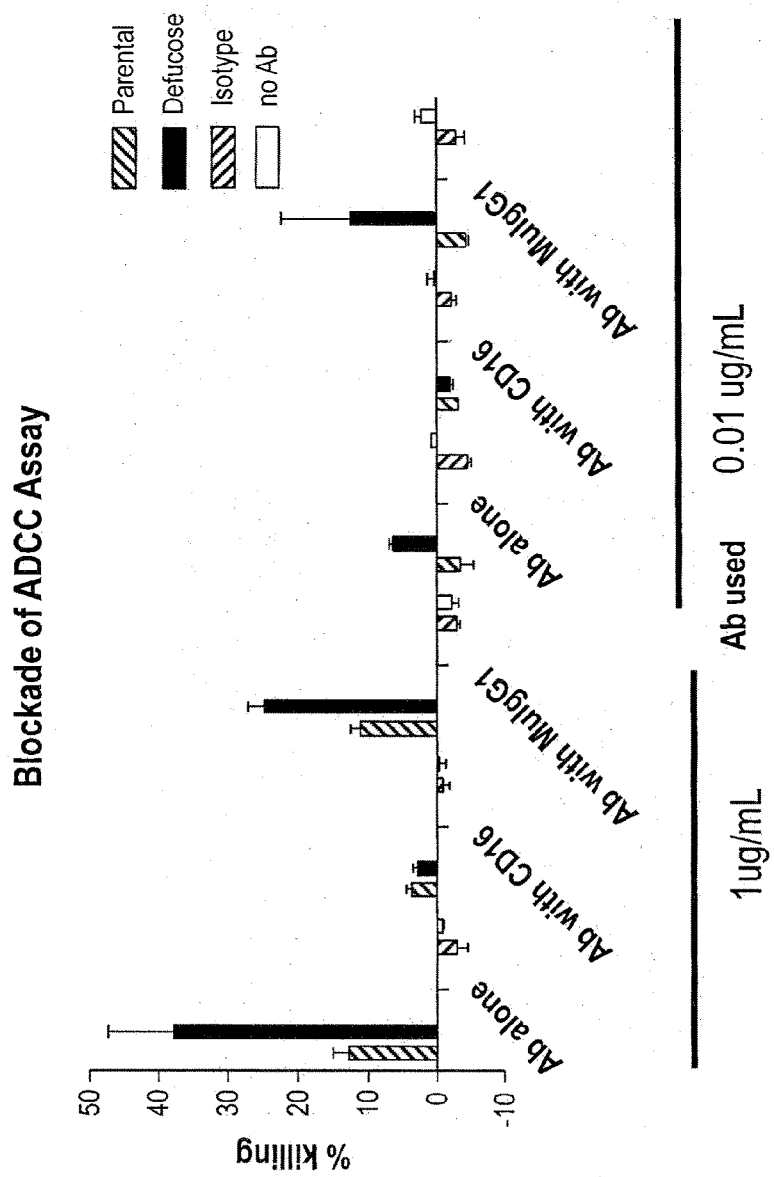
FIG. 17 is a bar graph of ADCC assay results for defucosylated 2A10 mAb ("defucose") as compared to fucosylated 2A10 mAb ("parental") and an isotype control or no antibody control, in which ADCC activity was blocked with an anti-CD16 antibody.

CD16 (FcγRIII) is a key receptor that mediates ADCC. The specificity of the ADCC response was shown by blocking the interaction of target and effector cells using a monoclonal antibody directed against CD16. Blockade of ADCC with anti-CD16 antibodies was conducted according to the ADCC assay described above, with the following modifications. The cells were incubated with either 1 μg/ml (a saturating dose) or 0.01 μg/ml (a sub-optimal dose) of 2A10 anti-PSMA antibodies (Ms704 or CHO DG44 expressed) in the absence or presence of 5 μg/ml of anti-CD16 antibody 3G8 or isotype control antibody. The results are shown in FIG. 17. One μg/ml of anti-PSMA antibody, in the absence of anti-CD16 antibody, induced approximately 12% and 37% lysis with fucosylated and defucosylated antibody, respectively. This % lysis was reduced to less than 5% in the presence of anti-CD16 antibody while isotype control antibody had essentially no effect.

Equivalents

Those skilled in the art will recognize, or be able to ascertain using no more than routine experimentation, many equivalents of the specific embodiments of the invention described herein. Such equivalents are intended to be encompassed by the following claims.

SUMMARY OF SEQUENCE LISTING

| SEQ ID NO: | SEQUENCE |
|---|---|
| 1 | VH a.a. 4A3 |
| 2 | VH a.a. 7F12 |
| 3 | VH a.a. 8C12 |
| 4 | VH a.a. 8A11 |
| 5 | VH a.a. 16F9 |
| 6 | VH a.a. 2A10 |
| 7 | VH a.a. 2C6 |
| 8 | VH a.a. 2F5 |
| 9 | VH a.a. 1C3 |
| 10 | Vk a.a. 4A3 |
| 11 | Vk a.a. 7F12 |
| 12 | Vk a.a. 8C12 |
| 13 | Vk a.a. 8A11 |
| 14 | Vk a.a. 16F9 |
| 15 | Vk a.a. 2A10 |
| 16 | Vk a.a. 2C6 |
| 17 | Vk a.a. 2F5 |
| 18 | Vk a.a. 1C3 |
| 19 | VH CDR1 a.a. 4A3 |
| 20 | VH CDR1 a.a. 7F12 |
| 21 | VH CDR1 a.a. 8C12 |
| 22 | VH CDR1 a.a. 8A11 |
| 23 | VH CDR1 a.a. 16F9 |
| 24 | VH CDR1 a.a. 2A10 |
| 25 | VH CDR1 a.a. 2C6 |
| 26 | VH CDR1 a.a. 2F5 |
| 27 | VH CDR1 a.a. 1C3 |
| 28 | VH CDR2 a.a. 4A3 |
| 29 | VH CDR2 a.a. 7F12 |
| 30 | VH CDR2 a.a. 8C12 |
| 31 | VH CDR2 a.a. 8A11 |
| 32 | VH CDR2 a.a. 16F9 |
| 33 | VH CDR2 a.a. 2A10 |
| 34 | VH CDR2 a.a. 2C6 |
| 35 | VH CDR2 a.a. 2F5 |
| 36 | VH CDR2 a.a. 1C3 |
| 37 | VH CDR3 a.a. 4A3 |
| 38 | VH CDR3 a.a. 7F12 |
| 39 | VH CDR3 a.a. 8C12 |
| 40 | VH CDR3 a.a. 8A11 |
| 41 | VH CDR3 a.a. 16F9 |
| 42 | VH CDR3 a.a. 2A10 |
| 43 | VH CDR3 a.a. 2C6 |
| 44 | VH CDR3 a.a. 2F5 |
| 45 | VH CDR3 a.a. 1C3 |
| 46 | Vk CDR1 a.a. 4A3 |
| 47 | Vk CDR1 a.a. 7F12 |
| 48 | Vk CDR1 a.a. 8C12 |
| 49 | Vk CDR1 a.a. 8A11 |
| 50 | Vk CDR1 a.a. 16F9 |
| 51 | Vk CDR1 a.a. 2A10 |
| 52 | Vk CDR1 a.a. 2C6 |
| 53 | Vk CDR1 a.a. 2F5 |
| 54 | Vk CDR1 a.a. 1C3 |
| 55 | Vk CDR2 a.a. 4A3 |
| 56 | Vk CDR2 a.a. 7F12 |
| 57 | Vk CDR2 a.a. 8C12 |
| 58 | Vk CDR2 a.a. 8A11 |
| 59 | Vk CDR2 a.a. 16F9 |
| 60 | Vk CDR2 a.a. 2A10 |
| 61 | Vk CDR2 a.a. 2C6 |
| 62 | Vk CDR2 a.a. 2F5 |
| 63 | Vk CDR2 a.a. 1C3 |
| 64 | Vk CDR3 a.a. 4A3 |
| 65 | Vk CDR3 a.a. 7F12 |
| 66 | Vk CDR3 a.a. 8C12 |
| 67 | Vk CDR3 a.a. 8A11 |
| 68 | Vk CDR3 a.a. 16F9 |
| 69 | Vk CDR3 a.a. 2A10 |
| 70 | Vk CDR3 a.a. 2C6 |
| 71 | Vk CDR3 a.a. 2F5 |
| 72 | Vk CDR3 a.a. 1C3 |
| 73 | VH 5-51 germline a.a. |
| 74 | Vk L6 germline a.a. |
| 75 | Vk O4/O14 germline a.a. |
| 76 | VH 3-30.3 germline a.a. |
| 77 | Vk L18 germline a.a. |
| 78 | VH n.t. 1C3 |
| 79 | VH n.t. 2A10 |
| 80 | VH n.t. 2C6 |
| 81 | VH n.t. 2F5 |
| 82 | Vk n.t. 1C3 |
| 83 | Vk n.t. 2A10 |
| 84 | Vk n.t. 2C6 |
| 85 | Vk n.t. 2F5 |
| 86 | JH6b germline a.a. |
| 87 | JK3 germline a.a. |
| 88 | JK4 germline a.a. |
| 89 | $(Gly_4\text{-}Ser)_3$ a.a. |

SEQUENCE LISTING

<160> NUMBER OF SEQ ID NOS: 89

<210> SEQ ID NO 1

-continued

```
<211> LENGTH: 119
<212> TYPE: PRT
<213> ORGANISM: Homo sapiens

<400> SEQUENCE: 1

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
                20                  25                  30

Trp Ile Gly Trp Ala Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ser Ala Ala Asn Ser Ser His Trp Tyr Phe Asp Leu Trp Gly Arg Gly
            100                 105                 110

Thr Leu Val Thr Val Ser Ser
        115

<210> SEQ ID NO 2
<211> LENGTH: 119
<212> TYPE: PRT
<213> ORGANISM: Homo sapiens

<400> SEQUENCE: 2

Ala Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Phe
                20                  25                  30

Trp Ile Gly Trp Ala Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Thr Ala Asn Ser Ser Phe Trp Asn Phe Asp Leu Trp Gly Arg Gly
            100                 105                 110

Thr Leu Val Thr Val Ser Ser
        115

<210> SEQ ID NO 3
<211> LENGTH: 119
<212> TYPE: PRT
<213> ORGANISM: Homo sapiens

<400> SEQUENCE: 3

Glu Val Gln Leu Val Gln Ser Gly Ala Glu Val Lys Thr Pro Gly Glu
 1               5                  10                  15

Ser Leu Lys Ile Ser Cys Lys Gly Ser Gly Tyr Thr Phe Thr Ser Tyr
                20                  25                  30

Trp Ile Gly Trp Val Arg Gln Met Pro Gly Lys Gly Pro Glu Trp Met
            35                  40                  45

Gly Ile Ile Tyr Pro Gly Asp Ser Asp Thr Arg Tyr Ser Pro Ser Phe
```

```
                50                  55                  60
Gln Gly Gln Val Thr Phe Ser Ala Asp Lys Ser Ile Ser Thr Ala Tyr
 65                  70                  75                  80

Leu Gln Trp Asn Ser Leu Lys Thr Ser Asp Thr Ala Met Tyr Tyr Cys
                 85                  90                  95

Ala Thr Ala Asn Pro Ser Tyr Trp Tyr Phe Asp Leu Trp Gly Arg Gly
                100                 105                 110

Thr Leu Val Thr Val Ser Ser
            115

<210> SEQ ID NO 4
<211> LENGTH: 113
<212> TYPE: PRT
<213> ORGANISM: Homo sapiens

<400> SEQUENCE: 4

Ser Gly Ala Glu Val Lys Thr Pro Gly Glu Ser Leu Lys Ile Ser Cys
  1               5                  10                  15

Lys Gly Ser Gly Tyr Thr Phe Thr Asn Tyr Trp Ile Gly Trp Val Arg
             20                  25                  30

Gln Met Pro Gly Lys Gly Pro Glu Trp Met Gly Ile Ile Tyr Pro Gly
         35                  40                  45

Asp Ser Asp Thr Arg Tyr Ser Pro Ser Phe Gln Gly Gln Val Thr Phe
     50                  55                  60

Ser Ala Asp Lys Ser Ile Ser Thr Ala Tyr Leu Gln Trp Ser Ser Leu
 65                  70                  75                  80

Lys Thr Ser Asp Thr Ala Met Tyr Tyr Cys Ala Thr Ala Asn Pro Ser
                 85                  90                  95

Tyr Trp Tyr Phe Asp Leu Trp Gly Arg Gly Thr Leu Val Thr Val Ser
                100                 105                 110

Ser

<210> SEQ ID NO 5
<211> LENGTH: 113
<212> TYPE: PRT
<213> ORGANISM: Homo sapiens

<400> SEQUENCE: 5

Ser Gly Ala Glu Leu Lys Lys Pro Gly Glu Ser Leu Lys Ile Ser Cys
  1               5                  10                  15

Lys Gly Ser Gly Tyr Ser Phe Thr Asn Tyr Trp Ile Gly Trp Ala Arg
             20                  25                  30

Gln Met Pro Gly Lys Gly Leu Glu Trp Met Gly Ile Ile Tyr Pro Gly
         35                  40                  45

Asp Ser Asp Thr Arg Tyr Ser Pro Ser Phe Gln Gly Gln Val Thr Ile
     50                  55                  60

Ser Ala Asp Lys Ser Val Ser Thr Ala Tyr Leu Gln Trp Asn Ser Leu
 65                  70                  75                  80

Lys Ala Ser Asp Thr Ala Met Tyr Tyr Cys Ala Thr Ala Asn Ser Ser
                 85                  90                  95

Phe Trp Asn Phe Asp Leu Trp Gly Arg Gly Thr Leu Val Thr Val Ser
                100                 105                 110

Ser

<210> SEQ ID NO 6
<211> LENGTH: 119
<212> TYPE: PRT
```

<213> ORGANISM: Homo sapiens

<400> SEQUENCE: 6

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Asn
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Thr Gly Phe Leu Trp Ser Ser Asp Leu Trp Gly Arg Gly
            100                 105                 110

Thr Leu Val Thr Val Ser Ser
        115

<210> SEQ ID NO 7
<211> LENGTH: 121
<212> TYPE: PRT
<213> ORGANISM: Homo sapiens

<400> SEQUENCE: 7

Glu Val Gln Leu Val Gln Ser Gly Ser Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Ser Pro Gly Tyr Thr Ser Ser Trp Thr Ser Phe Asp Tyr Trp Gly
            100                 105                 110

Gln Gly Thr Leu Val Thr Val Ser Ser
        115                 120

<210> SEQ ID NO 8
<211> LENGTH: 119
<212> TYPE: PRT
<213> ORGANISM: Homo sapiens

<400> SEQUENCE: 8

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Asn
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

-continued

Gln Gly Gln Val Thr Ile Ser Ala Asp Lys Ser Ile Ser Thr Ala Tyr
 65                  70                  75                  80

Leu Gln Trp Asn Ser Leu Lys Ala Ser Asp Thr Ala Met Tyr Tyr Cys
                 85                  90                  95

Ala Arg Gln Thr Gly Phe Leu Trp Ser Phe Asp Leu Trp Gly Arg Gly
            100                 105                 110

Thr Leu Val Thr Val Ser Ser
        115

<210> SEQ ID NO 9
<211> LENGTH: 124
<212> TYPE: PRT
<213> ORGANISM: Homo sapiens

<400> SEQUENCE: 9

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Asn Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Val Pro Trp Gly Ser Arg Tyr Tyr Tyr Tyr Gly Met Asp
            100                 105                 110

Val Trp Gly Gln Gly Thr Thr Val Thr Val Ser Ser
        115                 120

<210> SEQ ID NO 10
<211> LENGTH: 108
<212> TYPE: PRT
<213> ORGANISM: Homo sapiens

<400> SEQUENCE: 10

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
            20                  25                  30

Leu Ala Trp Phe Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Leu Met
                 85                  90                  95

Tyr Thr Phe Gly Gln Gly Thr Lys Leu Glu Ile Lys
            100                 105

<210> SEQ ID NO 11
<211> LENGTH: 108
<212> TYPE: PRT
<213> ORGANISM: Homo sapiens

<400> SEQUENCE: 11

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Leu Met
                85                  90                  95

Tyr Thr Phe Gly Gln Gly Thr Lys Leu Glu Ile Lys
               100                 105
```

<210> SEQ ID NO 12
<211> LENGTH: 108
<212> TYPE: PRT
<213> ORGANISM: Homo sapiens

<400> SEQUENCE: 12

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asp Trp Leu Met
                85                  90                  95

Tyr Thr Phe Gly Gln Gly Thr Lys Leu Glu Ile Lys
               100                 105
```

<210> SEQ ID NO 13
<211> LENGTH: 100
<212> TYPE: PRT
<213> ORGANISM: Homo sapiens

<400> SEQUENCE: 13

```
Pro Ser Ser Leu Ser Ala Ser Val Gly Asp Ser Val Thr Ile Thr Cys
 1               5                  10                  15

Arg Val Ser Gln Gly Ile Ser Ser Tyr Leu Asn Trp Tyr Arg Gln Lys
                20                  25                  30

Pro Gly Lys Val Pro Lys Leu Leu Ile Tyr Ser Ala Ser Asn Leu Gln
            35                  40                  45

Ser Gly Val Pro Ser Arg Phe Ser Gly Ser Gly Ser Gly Thr Asp Phe
 50                  55                  60

Thr Leu Thr Ile Asn Ser Leu Gln Pro Glu Asp Val Ala Thr Tyr Tyr
 65                  70                  75                  80

Gly Gln Arg Thr Tyr Asn Ala Pro Phe Thr Phe Gly Pro Gly Thr Lys
                85                  90                  95

Val Asp Ile Lys
               100
```

<210> SEQ ID NO 14
<211> LENGTH: 100
<212> TYPE: PRT
<213> ORGANISM: Homo sapiens

<400> SEQUENCE: 14

```
Pro Ser Ser Leu Ser Ala Ser Val Gly Asp Arg Val Thr Ile Thr Cys
 1               5                  10                  15

Arg Val Ser Gln Gly Ile Ser Ser Tyr Leu Asn Trp Tyr Arg Gln Lys
            20                  25                  30

Pro Gly Lys Val Pro Lys Leu Leu Met Tyr Ser Ala Ser Asn Leu Gln
        35                  40                  45

Ser Gly Val Pro Ser Arg Phe Ser Gly Ser Gly Ser Gly Thr Asp Phe
    50                  55                  60

Thr Leu Thr Ile Ser Ser Leu Gln Pro Glu Asp Val Ala Thr Tyr Tyr
65                  70                  75                  80

Gly Gln Arg Thr Tyr Asn Ala Pro Phe Thr Phe Gly Pro Gly Thr Lys
                85                  90                  95

Val Asp Ile Lys
            100
```

<210> SEQ ID NO 15
<211> LENGTH: 107
<212> TYPE: PRT
<213> ORGANISM: Homo sapiens

<400> SEQUENCE: 15

```
Ala Ile Gln Leu Thr Gln Ser Pro Ser Ser Leu Ser Ala Ser Val Gly
 1               5                  10                  15

Asp Arg Val Thr Ile Thr Cys Arg Ala Ser Gln Asp Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Tyr Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105
```

<210> SEQ ID NO 16
<211> LENGTH: 108
<212> TYPE: PRT
<213> ORGANISM: Homo sapiens

<400> SEQUENCE: 16

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80
```

```
Glu Asp Phe Ala Val Tyr Tyr Cys Gln Gln Arg Ser Asn Trp Pro Leu
                85                  90                  95
Phe Thr Phe Gly Pro Gly Thr Lys Val Asp Ile Lys
            100                 105

<210> SEQ ID NO 17
<211> LENGTH: 109
<212> TYPE: PRT
<213> ORGANISM: Homo sapiens

<400> SEQUENCE: 17

Ala Ile Gln Leu Thr Gln Ser Pro Ser Ser Leu Ser Ala Ser Val Gly
 1               5                  10                  15
Asp Arg Val Thr Ile Thr Cys Arg Ala Ser Gln Asp Ile Ser Ser Ala
            20                  25                  30
Leu Ala Trp Tyr Gln Gln Lys Pro Gly Lys Ala Pro Lys Leu Leu Ile
         35                  40                  45
Tyr Asp Ala Ser Ser Leu Glu Ser Gly Val Pro Ser Arg Phe Ser Gly
 50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Phe Asn Ser Tyr Pro Leu
                85                  90                  95
Thr Phe Gly Gly Gly Thr Lys Val Glu Ile Lys Ile Lys
            100                 105

<210> SEQ ID NO 18
<211> LENGTH: 107
<212> TYPE: PRT
<213> ORGANISM: Homo sapiens

<400> SEQUENCE: 18

Ala Ile Gln Leu Thr Gln Ser Pro Ser Ser Leu Ser Ala Ser Val Gly
 1               5                  10                  15
Asp Arg Val Thr Ile Thr Cys Arg Ala Ser Gln Gly Ile Ser Ser Ala
            20                  25                  30
Leu Ala Trp Tyr Gln Gln Lys Ser Gly Lys Ala Pro Lys Leu Leu Ile
         35                  40                  45
Phe Asp Ala Ser Ser Leu Glu Ser Gly Val Pro Ser Arg Phe Ser Gly
 50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Phe Asn Ser Tyr Pro Leu
                85                  90                  95
Thr Phe Gly Gly Gly Thr Lys Val Glu Ile Lys
            100                 105

<210> SEQ ID NO 19
<211> LENGTH: 5
<212> TYPE: PRT
<213> ORGANISM: Homo sapiens

<400> SEQUENCE: 19

Ser Tyr Trp Ile Gly
 1               5

<210> SEQ ID NO 20
<211> LENGTH: 5
<212> TYPE: PRT
```

-continued

<213> ORGANISM: Homo sapiens

<400> SEQUENCE: 20

Ser Phe Trp Ile Gly
1               5

<210> SEQ ID NO 21
<211> LENGTH: 5
<212> TYPE: PRT
<213> ORGANISM: Homo sapiens

<400> SEQUENCE: 21

Ser Tyr Trp Ile Gly
1               5

<210> SEQ ID NO 22
<211> LENGTH: 5
<212> TYPE: PRT
<213> ORGANISM: Homo sapiens

<400> SEQUENCE: 22

Asn Tyr Trp Ile Gly
1               5

<210> SEQ ID NO 23
<211> LENGTH: 5
<212> TYPE: PRT
<213> ORGANISM: Homo sapiens

<400> SEQUENCE: 23

Asn Tyr Trp Ile Gly
1               5

<210> SEQ ID NO 24
<211> LENGTH: 5
<212> TYPE: PRT
<213> ORGANISM: Homo sapiens

<400> SEQUENCE: 24

Ser Asn Trp Ile Gly
1               5

<210> SEQ ID NO 25
<211> LENGTH: 5
<212> TYPE: PRT
<213> ORGANISM: Homo sapiens

<400> SEQUENCE: 25

Asn Tyr Trp Ile Gly
1               5

<210> SEQ ID NO 26
<211> LENGTH: 5
<212> TYPE: PRT
<213> ORGANISM: Homo sapiens

<400> SEQUENCE: 26

Ser Asn Trp Ile Gly
1               5

<210> SEQ ID NO 27
<211> LENGTH: 5
<212> TYPE: PRT
<213> ORGANISM: Homo sapiens

<400> SEQUENCE: 27

```
Ser Tyr Ala Met His
  1               5
```

<210> SEQ ID NO 28
<211> LENGTH: 17
<212> TYPE: PRT
<213> ORGANISM: Homo sapiens

<400> SEQUENCE: 28

```
Ile Ile Tyr Pro Gly Asp Ser Asp Thr Arg Tyr Ser Pro Ser Phe Gln
  1               5                  10                  15

Gly
```

<210> SEQ ID NO 29
<211> LENGTH: 17
<212> TYPE: PRT
<213> ORGANISM: Homo sapiens

<400> SEQUENCE: 29

```
Ile Ile Tyr Pro Gly Asp Ser Asp Thr Arg Tyr Ser Pro Ser Phe Gln
  1               5                  10                  15

Gly
```

<210> SEQ ID NO 30
<211> LENGTH: 17
<212> TYPE: PRT
<213> ORGANISM: Homo sapiens

<400> SEQUENCE: 30

```
Ile Ile Tyr Pro Gly Asp Ser Asp Thr Arg Tyr Ser Pro Ser Phe Gln
  1               5                  10                  15

Gly
```

<210> SEQ ID NO 31
<211> LENGTH: 17
<212> TYPE: PRT
<213> ORGANISM: Homo sapiens

<400> SEQUENCE: 31

```
Ile Ile Tyr Pro Gly Asp Ser Asp Thr Arg Tyr Ser Pro Ser Phe Gln
  1               5                  10                  15

Gly
```

<210> SEQ ID NO 32
<211> LENGTH: 17
<212> TYPE: PRT
<213> ORGANISM: Homo sapiens

<400> SEQUENCE: 32

```
Ile Ile Tyr Pro Gly Asp Ser Asp Thr Arg Tyr Ser Pro Ser Phe Gln
  1               5                  10                  15

Gly
```

<210> SEQ ID NO 33
<211> LENGTH: 17
<212> TYPE: PRT
<213> ORGANISM: Homo sapiens

<400> SEQUENCE: 33

```
Ile Ile Tyr Pro Gly Asp Ser Asp Thr Arg Tyr Ser Pro Ser Phe Gln
  1               5                  10                  15
```

Gly

<210> SEQ ID NO 34
<211> LENGTH: 17
<212> TYPE: PRT
<213> ORGANISM: Homo sapiens

<400> SEQUENCE: 34

Ile Ile Tyr Pro Gly Asp Ser Asp Thr Arg Tyr Ser Pro Ser Phe Gln
 1               5                  10                  15

Gly

<210> SEQ ID NO 35
<211> LENGTH: 17
<212> TYPE: PRT
<213> ORGANISM: Homo sapiens

<400> SEQUENCE: 35

Ile Ile Tyr Pro Gly Asp Ser Asp Thr Arg Tyr Ser Pro Ser Phe Gln
 1               5                  10                  15

Gly

<210> SEQ ID NO 36
<211> LENGTH: 17
<212> TYPE: PRT
<213> ORGANISM: Homo sapiens

<400> SEQUENCE: 36

Val Ile Ser Tyr Asp Gly Asn Asn Lys Tyr Tyr Ala Asp Ser Val Lys
 1               5                  10                  15

Gly

<210> SEQ ID NO 37
<211> LENGTH: 10
<212> TYPE: PRT
<213> ORGANISM: Homo sapiens

<400> SEQUENCE: 37

Ala Asn Ser Ser His Trp Tyr Phe Asp Leu
 1               5                  10

<210> SEQ ID NO 38
<211> LENGTH: 10
<212> TYPE: PRT
<213> ORGANISM: Homo sapiens

<400> SEQUENCE: 38

Ala Asn Ser Ser Phe Trp Asn Phe Asp Leu
 1               5                  10

<210> SEQ ID NO 39
<211> LENGTH: 10
<212> TYPE: PRT
<213> ORGANISM: Homo sapiens

<400> SEQUENCE: 39

Ala Asn Pro Ser Tyr Trp Tyr Phe Asp Leu
 1               5                  10

<210> SEQ ID NO 40
<211> LENGTH: 10
<212> TYPE: PRT
<213> ORGANISM: Homo sapiens

```
<400> SEQUENCE: 40

Ala Asn Pro Ser Tyr Trp Tyr Phe Asp Leu
 1               5                  10

<210> SEQ ID NO 41
<211> LENGTH: 10
<212> TYPE: PRT
<213> ORGANISM: Homo sapiens

<400> SEQUENCE: 41

Ala Asn Ser Ser Phe Trp Asn Phe Asp Leu
 1               5                  10

<210> SEQ ID NO 42
<211> LENGTH: 10
<212> TYPE: PRT
<213> ORGANISM: Homo sapiens

<400> SEQUENCE: 42

Gln Thr Gly Phe Leu Trp Ser Ser Asp Leu
 1               5                  10

<210> SEQ ID NO 43
<211> LENGTH: 12
<212> TYPE: PRT
<213> ORGANISM: Homo sapiens

<400> SEQUENCE: 43

Pro Gly Tyr Thr Ser Ser Trp Thr Ser Phe Asp Tyr
 1               5                  10

<210> SEQ ID NO 44
<211> LENGTH: 10
<212> TYPE: PRT
<213> ORGANISM: Homo sapiens

<400> SEQUENCE: 44

Gln Thr Gly Phe Leu Trp Ser Phe Asp Leu
 1               5                  10

<210> SEQ ID NO 45
<211> LENGTH: 15
<212> TYPE: PRT
<213> ORGANISM: Homo sapiens

<400> SEQUENCE: 45

Ala Val Pro Trp Gly Ser Arg Tyr Tyr Tyr Gly Met Asp Val
 1               5                  10                  15

<210> SEQ ID NO 46
<211> LENGTH: 11
<212> TYPE: PRT
<213> ORGANISM: Homo sapiens

<400> SEQUENCE: 46

Arg Ala Ser Gln Ser Val Ser Ser Tyr Leu Ala
 1               5                  10

<210> SEQ ID NO 47
<211> LENGTH: 11
<212> TYPE: PRT
<213> ORGANISM: Homo sapiens

<400> SEQUENCE: 47

Arg Ala Ser Gln Ser Val Ser Ser Tyr Leu Ala
```

```
<210> SEQ ID NO 48
<211> LENGTH: 11
<212> TYPE: PRT
<213> ORGANISM: Homo sapiens

<400> SEQUENCE: 48

Arg Ala Ser Gln Ser Val Ser Ser Tyr Leu Ala
 1               5                  10

<210> SEQ ID NO 49
<211> LENGTH: 11
<212> TYPE: PRT
<213> ORGANISM: Homo sapiens

<400> SEQUENCE: 49

Thr Cys Arg Val Ser Gln Gly Ile Ser Ser Tyr
 1               5                  10

<210> SEQ ID NO 50
<211> LENGTH: 11
<212> TYPE: PRT
<213> ORGANISM: Homo sapiens

<400> SEQUENCE: 50

Thr Cys Arg Val Ser Gln Gly Ile Ser Ser Tyr
 1               5                  10

<210> SEQ ID NO 51
<211> LENGTH: 11
<212> TYPE: PRT
<213> ORGANISM: Homo sapiens

<400> SEQUENCE: 51

Arg Ala Ser Gln Asp Ile Ser Ser Ala Leu Ala
 1               5                  10

<210> SEQ ID NO 52
<211> LENGTH: 11
<212> TYPE: PRT
<213> ORGANISM: Homo sapiens

<400> SEQUENCE: 52

Arg Ala Ser Gln Ser Val Ser Ser Tyr Leu Ala
 1               5                  10

<210> SEQ ID NO 53
<211> LENGTH: 11
<212> TYPE: PRT
<213> ORGANISM: Homo sapiens

<400> SEQUENCE: 53

Arg Ala Ser Gln Asp Ile Ser Ser Ala Leu Ala
 1               5                  10

<210> SEQ ID NO 54
<211> LENGTH: 11
<212> TYPE: PRT
<213> ORGANISM: Homo sapiens

<400> SEQUENCE: 54

Arg Ala Ser Gln Gly Ile Ser Ser Ala Leu Ala
 1               5                  10
```

```
<210> SEQ ID NO 55
<211> LENGTH: 7
<212> TYPE: PRT
<213> ORGANISM: Homo sapiens

<400> SEQUENCE: 55

Asp Ala Ser Asn Arg Ala Thr
1               5

<210> SEQ ID NO 56
<211> LENGTH: 7
<212> TYPE: PRT
<213> ORGANISM: Homo sapiens

<400> SEQUENCE: 56

Asp Ala Ser Asn Arg Ala Thr
1               5

<210> SEQ ID NO 57
<211> LENGTH: 7
<212> TYPE: PRT
<213> ORGANISM: Homo sapiens

<400> SEQUENCE: 57

Asp Ala Ser Asn Arg Ala Thr
1               5

<210> SEQ ID NO 58
<211> LENGTH: 7
<212> TYPE: PRT
<213> ORGANISM: Homo sapiens

<400> SEQUENCE: 58

Ser Ala Ser Asn Leu Gln Ser
1               5

<210> SEQ ID NO 59
<211> LENGTH: 7
<212> TYPE: PRT
<213> ORGANISM: Homo sapiens

<400> SEQUENCE: 59

Ser Ala Ser Asn Leu Gln Ser
1               5

<210> SEQ ID NO 60
<211> LENGTH: 7
<212> TYPE: PRT
<213> ORGANISM: Homo sapiens

<400> SEQUENCE: 60

Asp Ala Ser Ser Leu Glu Ser
1               5

<210> SEQ ID NO 61
<211> LENGTH: 7
<212> TYPE: PRT
<213> ORGANISM: Homo sapiens

<400> SEQUENCE: 61

Asp Ala Ser Asn Arg Ala Thr
1               5

<210> SEQ ID NO 62
<211> LENGTH: 7
<212> TYPE: PRT
```

<213> ORGANISM: Homo sapiens

<400> SEQUENCE: 62

Asp Ala Ser Ser Leu Glu Ser
 1               5

<210> SEQ ID NO 63
<211> LENGTH: 7
<212> TYPE: PRT
<213> ORGANISM: Homo sapiens

<400> SEQUENCE: 63

Asp Ala Ser Ser Leu Glu Ser
 1               5

<210> SEQ ID NO 64
<211> LENGTH: 10
<212> TYPE: PRT
<213> ORGANISM: Homo sapiens

<400> SEQUENCE: 64

Gln Gln Arg Ser Asn Trp Leu Met Tyr Thr
 1               5                  10

<210> SEQ ID NO 65
<211> LENGTH: 10
<212> TYPE: PRT
<213> ORGANISM: Homo sapiens

<400> SEQUENCE: 65

Gln Gln Arg Ser Asn Trp Leu Met Tyr Thr
 1               5                  10

<210> SEQ ID NO 66
<211> LENGTH: 10
<212> TYPE: PRT
<213> ORGANISM: Homo sapiens

<400> SEQUENCE: 66

Gln Gln Arg Ser Asp Trp Leu Met Tyr Thr
 1               5                  10

<210> SEQ ID NO 67
<211> LENGTH: 9
<212> TYPE: PRT
<213> ORGANISM: Homo sapiens

<400> SEQUENCE: 67

Gln Arg Thr Tyr Asn Ala Pro Phe Thr
 1               5

<210> SEQ ID NO 68
<211> LENGTH: 9
<212> TYPE: PRT
<213> ORGANISM: Homo sapiens

<400> SEQUENCE: 68

Gln Arg Thr Tyr Asn Ala Pro Phe Thr
 1               5

<210> SEQ ID NO 69
<211> LENGTH: 9
<212> TYPE: PRT
<213> ORGANISM: Homo sapiens

<400> SEQUENCE: 69

```
Gln Gln Phe Asn Ser Tyr Pro Leu Thr
  1               5
```

<210> SEQ ID NO 70
<211> LENGTH: 10
<212> TYPE: PRT
<213> ORGANISM: Homo sapiens

<400> SEQUENCE: 70

```
Gln Gln Arg Ser Asn Trp Pro Leu Phe Thr
  1               5                  10
```

<210> SEQ ID NO 71
<211> LENGTH: 9
<212> TYPE: PRT
<213> ORGANISM: Homo sapiens

<400> SEQUENCE: 71

```
Gln Gln Phe Asn Ser Tyr Pro Leu Thr
  1               5
```

<210> SEQ ID NO 72
<211> LENGTH: 9
<212> TYPE: PRT
<213> ORGANISM: Homo sapiens

<400> SEQUENCE: 72

```
Gln Gln Phe Asn Ser Tyr Pro Leu Thr
  1               5
```

<210> SEQ ID NO 73
<211> LENGTH: 98
<212> TYPE: PRT
<213> ORGANISM: Homo sapiens

<400> SEQUENCE: 73

```
Glu Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Thr Ser Tyr
                 20                  25                  30

Trp Ile Gly Trp Val Arg Gln Met Pro Gly Lys Gly Leu Glu Trp Met
             35                  40                  45

Gly Ile Ile Tyr Pro Gly Asp Ser Asp Thr Arg Tyr Ser Pro Ser Phe
         50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg
```

<210> SEQ ID NO 74
<211> LENGTH: 94
<212> TYPE: PRT
<213> ORGANISM: Homo sapiens

<400> SEQUENCE: 74

```
Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
```

```
                35                  40                  45
Tyr Asp Ala Ser Asn Arg Ala Thr Gly Ile Pro Ala Arg Phe Ser Gly
         50                  55                  60
Ser Gly Ser Gly Thr Asp Phe Thr Leu Thr Ile Ser Ser Leu Glu Pro
 65                  70                  75                  80
Glu Asp Phe Ala Val Tyr Tyr Cys Gln Gln Arg Ser Asn Trp
                 85                  90
```

<210> SEQ ID NO 75
<211> LENGTH: 97
<212> TYPE: PRT
<213> ORGANISM: Homo sapiens

<400> SEQUENCE: 75

```
Asp Ile Gln Leu Thr Gln Ser Pro Ser Ser Leu Ser Ala Ser Val Gly
  1               5                  10                  15
Asp Arg Val Thr Ile Thr Cys Arg Val Ser Gln Gly Ile Ser Ser Tyr
                 20                  25                  30
Leu Asn Trp Tyr Arg Gln Lys Pro Gly Lys Val Pro Lys Leu Leu Ile
             35                  40                  45
Tyr Ser Ala Ser Asn Leu Gln Ser Gly Val Pro Ser Arg Phe Ser Gly
         50                  55                  60
Ser Gly Ser Gly Thr Asp Phe Thr Leu Thr Ile Ser Ser Leu Gln Pro
 65                  70                  75                  80
Glu Asp Val Ala Thr Tyr Tyr Gly Gln Arg Thr Tyr Asn Ala Pro Phe
                 85                  90                  95
Thr
```

<210> SEQ ID NO 76
<211> LENGTH: 98
<212> TYPE: PRT
<213> ORGANISM: Homo sapiens

<400> SEQUENCE: 76

```
Gln Val Gln Leu Val Glu Ser Gly Gly Gly Val Val Gln Pro Gly Arg
  1               5                  10                  15
Ser Leu Arg Leu Ser Cys Ala Ala Ser Gly Phe Thr Phe Ser Ser Tyr
                 20                  25                  30
Ala Met His Trp Val Arg Gln Ala Pro Gly Lys Gly Leu Glu Trp Val
             35                  40                  45
Ala Val Ile Ser Tyr Asp Gly Ser Asn Lys Tyr Tyr Ala Asp Ser Val
         50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg
```

<210> SEQ ID NO 77
<211> LENGTH: 95
<212> TYPE: PRT
<213> ORGANISM: Homo sapiens

<400> SEQUENCE: 77

```
Ala Ile Gln Leu Thr Gln Ser Pro Ser Ser Leu Ser Ala Ser Val Gly
  1               5                  10                  15
Asp Arg Val Thr Ile Thr Cys Arg Ala Ser Gln Gly Ile Ser Ser Ala
                 20                  25                  30
```

```
Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro
                 85                  90                  95

<210> SEQ ID NO 78
<211> LENGTH: 372
<212> TYPE: DNA
<213> ORGANISM: Homo sapiens
<220> FEATURE:
<221> NAME/KEY: CDS
<222> LOCATION: (1)..(372)

<400> SEQUENCE: 78 cag gtg caa ctg gtg gag tct ggg gga ggc gtg gtc cag cct ggg agg      48
Gln Val Gln Leu Val Glu Ser Gly Gly Gly Val Val Gln Pro Gly Arg
 1               5                  10                  15 tcc ctg aga ctc tcc tgt gca gcc tct gga ttc acc ttc agt agc tat      96
Ser Leu Arg Leu Ser Cys Ala Ala Ser Gly Phe Thr Phe Ser Ser Tyr
             20                  25                  30 gct atg cac tgg gtc cgc cag gct cca ggc aag ggg ctg gag tgg gtg     144
Ala Met His Trp Val Arg Gln Ala Pro Gly Lys Gly Leu Glu Trp Val
         35                  40                  45 gca gtt ata tca tat gat gga aac aat aaa tac tac gca gac tcc gtg     192
Ala Val Ile Ser Tyr Asp Gly Asn Asn Lys Tyr Tyr Ala Asp Ser Val
     50                  55                  60 aag ggc cga ttc acc atc tcc aga gac aat tcc aag aac acg ctg tat     240
Lys Gly Arg Phe Thr Ile Ser Arg Asp Asn Ser Lys Asn Thr Leu Tyr
 65                  70                  75                  80 ctg caa atg aac agc ctg aga gct gag gac acg gct gtg tat tac tgt     288
Leu Gln Met Asn Ser Leu Arg Ala Glu Asp Thr Ala Val Tyr Tyr Cys
                 85                  90                  95 gcg aga gcc gtc ccc tgg gga tcg agg tac tac tac tac ggt atg gac     336
Ala Arg Ala Val Pro Trp Gly Ser Arg Tyr Tyr Tyr Tyr Gly Met Asp
             100                 105                 110 gtc tgg ggc caa ggg acc acg gtc acc gtc tcc tca                     372
Val Trp Gly Gln Gly Thr Thr Val Thr Val Ser Ser
         115                 120

<210> SEQ ID NO 79
<211> LENGTH: 357
<212> TYPE: DNA
<213> ORGANISM: Homo sapiens
<220> FEATURE:
<221> NAME/KEY: CDS
<222> LOCATION: (1)..(357)

<400> SEQUENCE: 79 gag gtg cag ctg gtg cag tct gga gca gag gtg aaa aag ccc ggg gag      48
Glu Val Gln Leu Val Gln Ser Gly Ala Glu Val Lys Lys Pro Gly Glu
 1               5                  10                  15 tct ctg aag atc tcc tgt aag ggt tct gga tac agc ttt acc agt aac      96
Ser Leu Lys Ile Ser Cys Lys Gly Ser Gly Tyr Ser Phe Thr Ser Asn
             20                  25                  30 tgg atc ggc tgg gtg cgc cag atg ccc ggg aaa ggc ctg gag tgg atg     144
Trp Ile Gly Trp Val Arg Gln Met Pro Gly Lys Gly Leu Glu Trp Met
         35                  40                  45 ggg atc atc tat cct ggt gac tct gat acc aga tac agc ccg tcc ttc     192
```

```
Gly Ile Ile Tyr Pro Gly Asp Ser Asp Thr Arg Tyr Ser Pro Ser Phe
     50                  55                  60 caa ggc cag gtc acc atc tca gcc gac aag tcc atc agc acc gcc tac    240
Gln Gly Gln Val Thr Ile Ser Ala Asp Lys Ser Ile Ser Thr Ala Tyr
 65                  70                  75                  80 ctg cag tgg agc agc ctg aag gcc tcg gac acc gcc atg tat tac tgt    288
Leu Gln Trp Ser Ser Leu Lys Ala Ser Asp Thr Ala Met Tyr Tyr Cys
                 85                  90                  95 gcg agg caa act ggt ttc ctc tgg tcc tcc gat ctc tgg ggc cgt ggc    336
Ala Arg Gln Thr Gly Phe Leu Trp Ser Ser Asp Leu Trp Gly Arg Gly
            100                 105                 110 acc ctg gtc act gtc tcc tca                                        357
Thr Leu Val Thr Val Ser Ser
            115

<210> SEQ ID NO 80
<211> LENGTH: 363
<212> TYPE: DNA
<213> ORGANISM: Homo sapiens
<220> FEATURE:
<221> NAME/KEY: CDS
<222> LOCATION: (1)..(363)

<400> SEQUENCE: 80 gag gtg cag ctg gtg cag tct gga tca gag gtg aaa aag ccc ggg gag     48
Glu Val Gln Leu Val Gln Ser Gly Ser Glu Val Lys Lys Pro Gly Glu
  1               5                  10                  15 tct ctg aag atc tcc tgt aag ggt tct gga tac agc ttt acc aac tac     96
Ser Leu Lys Ile Ser Cys Lys Gly Ser Gly Tyr Ser Phe Thr Asn Tyr
                 20                  25                  30 tgg atc ggc tgg gtg cgc cag atg ccc ggg aaa ggc ctg gag tgg atg    144
Trp Ile Gly Trp Val Arg Gln Met Pro Gly Lys Gly Leu Glu Trp Met
             35                  40                  45 ggg atc atc tat cct ggt gac tct gat acc aga tac agc ccg tcc ttc    192
Gly Ile Ile Tyr Pro Gly Asp Ser Asp Thr Arg Tyr Ser Pro Ser Phe
     50                  55                  60 caa ggc cag gtc acc atc tca gcc gac aag tcc atc agc acc gcc tat    240
Gln Gly Gln Val Thr Ile Ser Ala Asp Lys Ser Ile Ser Thr Ala Tyr
 65                  70                  75                  80 ctg cag tgg agc agc ctg aag gcc tcg gac acc gcc atg tat tac tgt    288
Leu Gln Trp Ser Ser Leu Lys Ala Ser Asp Thr Ala Met Tyr Tyr Cys
                 85                  90                  95 gcg agt ccc ggg tat acc agc agt tgg act tct ttt gac tac tgg ggc    336
Ala Ser Pro Gly Tyr Thr Ser Ser Trp Thr Ser Phe Asp Tyr Trp Gly
            100                 105                 110 cag gga acc ctg gtc acc gtc tcc tca                                363
Gln Gly Thr Leu Val Thr Val Ser Ser
            115                 120

<210> SEQ ID NO 81
<211> LENGTH: 357
<212> TYPE: DNA
<213> ORGANISM: Homo sapiens
<220> FEATURE:
<221> NAME/KEY: CDS
<222> LOCATION: (1)..(357)

<400> SEQUENCE: 81 gag gtg cag ctg gtg cag tct gga gca gag gtg aaa aag ccc ggg gag     48
Glu Val Gln Leu Val Gln Ser Gly Ala Glu Val Lys Lys Pro Gly Glu
  1               5                  10                  15 tct ctg aag atc tcc tgt aag ggt tct gga tac agt ttt acc agc aac     96
Ser Leu Lys Ile Ser Cys Lys Gly Ser Gly Tyr Ser Phe Thr Ser Asn
                 20                  25                  30
```

```
tgg atc ggc tgg gtg cgc cag atg ccc ggg aaa ggc ctg gag tgg atg      144
Trp Ile Gly Trp Val Arg Gln Met Pro Gly Lys Gly Leu Glu Trp Met
        35                  40                  45 ggg atc atc tat cct ggt gac tct gat acc aga tac agc ccg tcc ttc      192
Gly Ile Ile Tyr Pro Gly Asp Ser Asp Thr Arg Tyr Ser Pro Ser Phe
 50                  55                  60 caa ggc cag gtc acc atc tca gcc gac aag tcc atc agc acc gcc tac      240
Gln Gly Gln Val Thr Ile Ser Ala Asp Lys Ser Ile Ser Thr Ala Tyr
 65                  70                  75                  80 ctg cag tgg aac agc ctg aag gcc tcg gac acc gcc atg tat tac tgt      288
Leu Gln Trp Asn Ser Leu Lys Ala Ser Asp Thr Ala Met Tyr Tyr Cys
            85                  90                  95 gcg aga caa act ggt ttc ctc tgg tcc ttc gat ctc tgg ggc cgt ggc      336
Ala Arg Gln Thr Gly Phe Leu Trp Ser Phe Asp Leu Trp Gly Arg Gly
           100                 105                 110 acc ctg gtc act gtc tcc tca                                          357
Thr Leu Val Thr Val Ser Ser
           115

<210> SEQ ID NO 82
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 82 gcc atc cag ttg acc cag tct cca tcc tcc ctg tct gca tct gta gga      48
Ala Ile Gln Leu Thr Gln Ser Pro Ser Ser Leu Ser Ala Ser Val Gly
 1               5                  10                  15 gac aga gtc acc atc act tgc cgg gca agt cag ggc att agc agt gct      96
Asp Arg Val Thr Ile Thr Cys Arg Ala Ser Gln Gly Ile Ser Ser Ala
            20                  25                  30 tta gcc tgg tat cag cag aaa tca ggg aaa gct cct aag ctc ctg atc     144
Leu Ala Trp Tyr Gln Gln Lys Ser Gly Lys Ala Pro Lys Leu Leu Ile
        35                  40                  45 ttt gat gcc tcc agt ttg gaa agt ggg gtc cca tca agg ttc agc ggc     192
Phe Asp Ala Ser Ser Leu Glu Ser Gly Val Pro Ser Arg Phe Ser Gly
 50                  55                  60 agt gga tct ggg aca gat ttc act ctc acc atc agc agc ctg cag cct     240
Ser Gly Ser Gly Thr Asp Phe Thr Leu Thr Ile Ser Ser Leu Gln Pro
 65                  70                  75                  80 gaa gat ttt gca act tat tac tgt caa cag ttt aac agt tat cct ctc     288
Glu Asp Phe Ala Thr Tyr Tyr Cys Gln Gln Phe Asn Ser Tyr Pro Leu
            85                  90                  95 act ttc ggc gga ggg acc aag gtg gag atc aaa                         321
Thr Phe Gly Gly Gly Thr Lys Val Glu Ile Lys
           100                 105

<210> SEQ ID NO 83
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 83 gcc atc cag ttg acc cag tct cca tcc tcc ctg tct gca tct gta gga      48
Ala Ile Gln Leu Thr Gln Ser Pro Ser Ser Leu Ser Ala Ser Val Gly
 1               5                  10                  15 gac aga gtc acc atc act tgc cgg gca agt cag gac att agc agt gct      96
Asp Arg Val Thr Ile Thr Cys Arg Ala Ser Gln Asp Ile Ser Ser Ala
```

```
                Asp Arg Val Thr Ile Thr Cys Arg Ala Ser Gln Asp Ile Ser Ser Ala
                             20                  25                  30 tta gcc tgg tat caa cag aaa cca ggg aaa gct cct aag ctc ctg atc        144
Leu Ala Trp Tyr Gln Gln Lys Pro Gly Lys Ala Pro Lys Leu Leu Ile
             35                  40                  45 tat gat gcc tcc agt ttg gaa agt ggg gtc cca tca agg ttc agc ggc        192
Tyr Asp Ala Ser Ser Leu Glu Ser Gly Val Pro Ser Arg Phe Ser Gly
 50                  55                  60 tat gga tct ggg aca gat ttc act ctc acc atc aac agc ctg cag cct        240
Tyr Gly Ser Gly Thr Asp Phe Thr Leu Thr Ile Asn Ser Leu Gln Pro
 65                  70                  75                  80 gaa gat ttt gca act tat tac tgt caa cag ttt aat agt tac ccg ctc        288
Glu Asp Phe Ala Thr Tyr Tyr Cys Gln Gln Phe Asn Ser Tyr Pro Leu
                 85                  90                  95 act ttc ggc gga ggg acc aag gtg gag atc aaa                            321
Thr Phe Gly Gly Gly Thr Lys Val Glu Ile Lys
            100                 105

<210> SEQ ID NO 84
<211> LENGTH: 324
<212> TYPE: DNA
<213> ORGANISM: Homo sapiens
<220> FEATURE:
<221> NAME/KEY: CDS
<222> LOCATION: (1)..(324)

<400> SEQUENCE: 84 gaa att gtg ttg aca cag tct cca gcc acc ctg tct ttg tct cca ggg         48
Glu Ile Val Leu Thr Gln Ser Pro Ala Thr Leu Ser Leu Ser Pro Gly
 1               5                  10                  15 gaa aga gcc acc ctc tcc tgc agg gcc agt cag agt gtt agc agc tac         96
Glu Arg Ala Thr Leu Ser Cys Arg Ala Ser Gln Ser Val Ser Ser Tyr
             20                  25                  30 tta gcc tgg tac caa cag aaa cct ggc cag gct ccc agg ctc ctc atc        144
Leu Ala Trp Tyr Gln Gln Lys Pro Gly Gln Ala Pro Arg Leu Leu Ile
             35                  40                  45 tat gat gca tcc aac agg gcc act ggc atc cca gcc agg ttc agt ggc        192
Tyr Asp Ala Ser Asn Arg Ala Thr Gly Ile Pro Ala Arg Phe Ser Gly
 50                  55                  60 agt ggg tct ggg aca gac ttc act ctc acc atc agc agc cta gag cct        240
Ser Gly Ser Gly Thr Asp Phe Thr Leu Thr Ile Ser Ser Leu Glu Pro
 65                  70                  75                  80 gaa gat ttt gca gtt tat tac tgt cag cag cgt agc aac tgg ccc cta        288
Glu Asp Phe Ala Val Tyr Tyr Cys Gln Gln Arg Ser Asn Trp Pro Leu
                 85                  90                  95 ttc act ttc ggc cct ggg acc aaa gtg gat atc aaa                        324
Phe Thr Phe Gly Pro Gly Thr Lys Val Asp Ile Lys
            100                 105

<210> SEQ ID NO 85
<211> LENGTH: 327
<212> TYPE: DNA
<213> ORGANISM: Homo sapiens
<220> FEATURE:
<221> NAME/KEY: CDS
<222> LOCATION: (1)..(327)

<400> SEQUENCE: 85 gcc atc cag ttg acc cag tct cca tcc tcc ctg tct gca tct gta gga         48
Ala Ile Gln Leu Thr Gln Ser Pro Ser Ser Leu Ser Ala Ser Val Gly
 1               5                  10                  15 gac aga gtc acc atc act tgc cgg gca agt cag gac att agc agt gct         96
Asp Arg Val Thr Ile Thr Cys Arg Ala Ser Gln Asp Ile Ser Ser Ala
             20                  25                  30
```

```
tta gcc tgg tat cag cag aaa ccg ggg aaa gct cct aag ctc ctg atc      144
Leu Ala Trp Tyr Gln Gln Lys Pro Gly Lys Ala Pro Lys Leu Leu Ile
        35                  40                  45 tat gat gcc tcc agt ttg gaa agt ggg gtc cca tca agg ttc agc ggc      192
Tyr Asp Ala Ser Ser Leu Glu Ser Gly Val Pro Ser Arg Phe Ser Gly
    50                  55                  60 agt gga tct ggg aca gat ttc act ctc acc atc agc agc ctg cag cct      240
Ser Gly Ser Gly Thr Asp Phe Thr Leu Thr Ile Ser Ser Leu Gln Pro
65                  70                  75                  80 gaa gat ttt gca act tat tac tgt caa cag ttt aat agt tac ccg ctc      288
Glu Asp Phe Ala Thr Tyr Tyr Cys Gln Gln Phe Asn Ser Tyr Pro Leu
                85                  90                  95 act ttc ggc gga ggg acc aag gtg gag atc aaa atc aaa                  327
Thr Phe Gly Gly Gly Thr Lys Val Glu Ile Lys Ile Lys
            100                 105
```

<210> SEQ ID NO 86
<211> LENGTH: 20
<212> TYPE: PRT
<213> ORGANISM: Homo sapiens

<400> SEQUENCE: 86

```
Tyr Tyr Tyr Tyr Tyr Gly Met Asp Val Trp Gly Gln Gly Thr Thr Val
 1               5                  10                  15

Thr Val Ser Ser
            20
```

<210> SEQ ID NO 87
<211> LENGTH: 12
<212> TYPE: PRT
<213> ORGANISM: Homo sapiens

<400> SEQUENCE: 87

```
Phe Thr Phe Gly Pro Gly Thr Lys Val Asp Ile Lys
 1               5                  10
```

<210> SEQ ID NO 88
<211> LENGTH: 12
<212> TYPE: PRT
<213> ORGANISM: Homo sapiens

<400> SEQUENCE: 88

```
Leu Thr Phe Gly Gly Gly Thr Lys Val Glu Ile Lys
 1               5                  10
```

<210> SEQ ID NO 89
<211> LENGTH: 15
<212> TYPE: PRT
<213> ORGANISM: Artificial Sequence
<220> FEATURE:
<223> OTHER INFORMATION: Description of Artificial Sequence: Synthetic
      Gly-Ser linker

<400> SEQUENCE: 89

```
Gly Gly Gly Gly Ser Gly Gly Gly Ser Gly Gly Gly Gly Ser
 1               5                  10                  15
```

We claim:

1. An isolated antibody that binds human prostate specific membrane antigen (PSMA) comprising a heavy chain variable region CDR1 comprising SEQ ID NO: 24, a heavy chain variable region CDR2 comprising SEQ ID NO: 33, and a heavy chain variable region CDR3 comprising SEQ ID NO: 42, a light chain variable region CDR1 comprising SEQ ID NO: 51, a light chain variable region CDR2 comprising SEQ ID NO: 60, and a light chain variable region CDR3 comprising SEQ ID NO: 69, wherein the antibody is linked to a therapeutic agent.

2. An isolated antibody that binds human prostate specific membrane antigen (PSMA) comprising heavy and light chain variable regions, wherein the light chain variable region comprises the amino acid sequence of SEQ ID NO: 15 set forth in SEQ ID NOs: 6 and 15, respectively, wherein the antibody is linked to a therapeutic agent.

3. The isolated antibody of claim 1 or 2, wherein the therapeutic agent is a cytotoxin, drug, or radioactive isotope.

4. The antibody of claim 1 or 2, which lacks fucose residues.

5. The antibody of claim 1 or 2, which is a monoclonal antibody.

6. The antibody of claim 1 or 2, which is a human, humanized or chimeric antibody.

7. An isolated full length antibody that binds to prostate specific membrane antigen (PSMA) comprising heavy and light chain variable regions set forth in SEQ ID NOs: 6 and 15, respectively.

8. The antibody of claim 3, wherein the cytotoxin is selected from the group consisting of antimetabolites, alkylating agents, anthracyclines, antibiotics, and anti-mitotic agents.

9. The antibody of claim 3, wherein the cytotoxin is selected from the group consisting of duocarmycins, calicheamicins, maytansines, and auristatins.

10. The antibody of claim 3, wherein the cytotoxin is selected from the group consisting of paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin.

11. The antibody of claim 8, wherein the antimetabolite is selected from the group consisting of methotrexate, 6-mercaptopurine, 6-thioguanine, cytarabine, and 5-fluorouracil decarbazine.

12. The antibody of claim 8, wherein the alkalating agent is selected from the group consisting of mechlorethamine, thioepa chlorambucil, melphalan, carmustine (BSNU), lomustine (CCNU), cyclothosphamide, busulfan, dibromomannitol, streptozotocin, mitomycin C, and cis- dichlorodiamine platinum (II) (DDP) cisplatin.

13. The antibody of claim 8, wherein the anthracycline is daunorubicin or doxorubicin.

14. The antibody of claim 8, wherein the antibiotic is selected from the group consisting of dactinomycin, bleomycin, mithramycin, and anthramycin.

15. The antibody of claim 8, wherein the anti-mitotic agent is vincristine or vinblastine.

16. The antibody of claim 3, wherein the drug is selected from the group consisting of an enzymatically active toxin or cytotoxic fragment thereof and a proinflammatory cytokine.

17. The antibody of claim 16, wherein the enzymatically active toxin is selected from the group consisting of abrin, ricin A, pseudomonas exotoxin, and diphtheria toxin.

18. The antibody of claim 16, wherein the proinflammatory cytokine is tumor necrosis factor or interferon gamma.

19. The antibody of claim 3, wherein the drug is selected from the group consisting of lymphokines, interleukin-1, interleukin-2, interleukin-6, granulocyte macrophage colony stimulating factor, and granulocyte colony stimulating factor.

20. A composition comprising the antibody of claim 1 and a carrier.

21. A composition comprising the antibody of claim 2 and a carrier.

22. A composition comprising the antibody of claim 7 and a carrier.

* * * * *

UNITED STATES PATENT AND TRADEMARK OFFICE
CERTIFICATE OF CORRECTION

PATENT NO. : 8,461,308 B2  
APPLICATION NO. : 12/903853  
DATED : June 11, 2013  
INVENTOR(S) : Josephine M. Cardarelli et al.

Page 1 of 1

It is certified that error appears in the above-identified patent and that said Letters Patent is hereby corrected as shown below:

In the claims, line 65 of column 102 to line 3 of column 103:

Please replace existing claim 2:

"An isolated antibody that binds human prostate specific membrane antigen (PSMA) comprising heavy and light chain variable regions, wherein the light chain variable region comprises the amino acid sequence of SEQ ID NO: 15 set forth in SEQ ID NOs: 6 and 15, respectively, wherein the antibody is linked to a therapeutic agent."

with the following:

-- An isolated antibody that binds human prostate specific membrane antigen (PSMA) comprising heavy and light chain variable regions set forth in SEQ ID NOs: 6 and 15, respectively, wherein the antibody is linked to a therapeutic agent. --.

Signed and Sealed this  
Sixteenth Day of July, 2013

Teresa Stanek Rea  
*Acting Director of the United States Patent and Trademark Office*